United States Patent
Oehlenschlaeger et al.

(10) Patent No.: US 10,954,478 B2
(45) Date of Patent: Mar. 23, 2021

(54) DETERGENT COMPOSITIONS AND USES THEREOF

(71) Applicant: NOVOZYMES A/S, Bagsvaerd (DK)

(72) Inventors: Christian B. Oehlenschlaeger, Valby (DK); Dorotea R. Segura, Rungsted (DK); Rebecca M. Vejborg, Allerød (DK); Henrik M. Geertz-Hansen, Copenhagen (DK); Lilian E. T. Baltsen, Bagsvaerd (DK); Jesper Salomon, Holte (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/093,706

(22) PCT Filed: Apr. 28, 2017

(86) PCT No.: PCT/EP2017/060252
§ 371 (c)(1),
(2) Date: Oct. 15, 2018

(87) PCT Pub. No.: WO2017/186937
PCT Pub. Date: Nov. 2, 2017

(65) Prior Publication Data
US 2019/0127663 A1    May 2, 2019

(30) Foreign Application Priority Data
Apr. 29, 2016  (DK) .................. PA 2016 00261

(51) Int. Cl.
*C12N 9/24*   (2006.01)
*C11D 3/386*  (2006.01)
(Continued)

(52) U.S. Cl.
CPC ........ *C11D 3/38636* (2013.01); *C11D 3/0005* (2013.01); *C11D 3/3951* (2013.01);
(Continued)

(58) Field of Classification Search
None
See application file for complete search history.

(56) References Cited

U.S. PATENT DOCUMENTS 6,465,410 B1  10/2002 Bettiol
6,468,955 B1  10/2002 Smets
(Continued)

FOREIGN PATENT DOCUMENTS

AU         6559390 A    5/1991
WO         98/50512 A1  11/1998
(Continued)

OTHER PUBLICATIONS

Andrew, 2016, Uniprot accession No. A0A0Q5CMZ8.
(Continued)

*Primary Examiner* — Richard C Ekstrom
(74) *Attorney, Agent, or Firm* — Elias Lambiris

(57) ABSTRACT

The present invention relates to polypeptides having hexosaminidase activity, and polynucleotides encoding the polypeptides. The invention also relates to nucleic acid constructs, vectors, and host cells comprising the polynucleotides as well as methods of producing and using the polypeptides.

20 Claims, 3 Drawing Sheets
Specification includes a Sequence Listing.

(51) Int. Cl.
*C11D 11/00* (2006.01)
*C11D 3/00* (2006.01)
*C11D 3/395* (2006.01)

(52) U.S. Cl.
CPC ........ *C11D 3/3953* (2013.01); *C11D 11/0017* (2013.01); *C11D 11/0023* (2013.01); *C12N 9/2402* (2013.01); *C12Y 302/01052* (2013.01)

(56) References Cited

U.S. PATENT DOCUMENTS

| | | | |
|---|---|---|---|
| 8,399,235 | B2 | 3/2013 | Frank |
| 8,821,862 | B2 | 9/2014 | Madhyastha |
| 2009/0155215 | A1 | 6/2009 | Collins |
| 2011/0196319 | A1 | 8/2011 | Arscott, II |
| 2012/0258089 | A1 | 10/2012 | Madhyastha |
| 2019/0127663 | A1* | 5/2019 | Oehlenschlaeger . C12N 9/2402 |
| 2019/0161707 | A1* | 5/2019 | Vejborg ............ C11D 3/38636 |
| 2019/0169547 | A1 | 6/2019 | Ooehlenschlaeger et al. |

FOREIGN PATENT DOCUMENTS

| | | |
|---|---|---|
| WO | 99/57157 A1 | 11/1999 |
| WO | 2008/043175 A1 | 4/2008 |
| WO | 2009/121183 A1 | 10/2009 |
| WO | 2012/129515 A1 | 9/2012 |
| WO | 2015/196299 A1 | 12/2015 |

OTHER PUBLICATIONS

Andrew, 2016, Uniprot accession No. A0A0Q5KJC4.
Anonymous, 2013, NCBI No. WP_005560708.
Anonymous, 2013, NCBI No. WP_017886882.1.
Anonymous, 2013, NCBI No. WP_018652103.
Anonymous, 2015, NCBI No. WP_051596815.1.
Durkin et al, 2012, EBI Accession No. J4TU99.
Gillaspy et al, 2014, EBI Accession No. X2JMQ1.
Jackson et al, 2011, EBI Accession No. P86956.
Joubert et al, 2012, EBI Accession No. H2A0L6.
Kaplan et al, 2003, J Bacteriol 185(16), 4693-4698.
Kaplan et al, 2004, EBI Accession No. Q6GYA5.
Kaplan et al, 2009, International journal of artificial organs 32(9), 545-554.
Keeling et al, 2013, Uniprot accession No. U4URB2.
Krishnamurthi et al, 2008, Int Sys Evol Microbiol 58, 2287-2291.
Liu et al, 2010, Int Sys Evol Microbiol 60, 2940-2945.
MacInnes et al, 2012, EBI Accession No. K0G581.
MacInnes et al, 2015, EBI Accession No. A0A0A7MHS5.
McKinlay et al, 2016, Uniprot accession No. A6VMN2.
Ramasubbu et al, 2005, J Mol Biol 349(3), 475-486.
Tews et al, 1998, EBI Accession No. Q54468.
Wang et al, 2014, Uniprot accession No. A0A075LPR4.
Ward et al, 2016, Uniprot accession No. D7N318.
Weinstock et al, 2015, Uniprot accession No. E4HHI5.
Zhan et al, 2015, Uniprot accession No. D9PAB0.

* cited by examiner

Figure 1

```
SEQ ID NO 20 Curtobacterium oceanosedimentum                        ARRASATDLQRAGIDLLNYNSYYLYEVPTDLDPADSEYTV
SEQ ID NO 33 Curtobacterium flaccumfaciens pv. flaccumfaciens       ARRASAVDLQQAGIDQLNYNSYYLYEVPTDLDPADSDYTV
SEQ ID NO 34 Curtobacterium luteum                                  ARRASAVDLQQAGIDQLNYNSYYLYEVPTDLDPADSDYTV
SEQ ID NO 35 Curtobacterium oceanosedimentum                        BRRACANDLYAAGIDLLNYNSYYLYEVPTDLDAADSEYTV
SEQ ID NO 36 Curtobacterium sp. Leaf154 DSM 102595                  ARRASAVDLQQAGIDMLNYNSYYLYEVPTDLPADSEYTV SEQ ID NO 20 Curtobacterium oceanosedimentum                        ADLRECWSLRAWDGDSCARLAAPMSGAAVAIWGEDLDGAP
SEQ ID NO 33 Curtobacterium flaccumfaciens pv. flaccumfaciens       ADLRENWSLRAWDGDSGSLLAAPMSGAAVAIWGEDLEDPP
SEQ ID NO 34 Curtobacterium luteum                                  ADLRENWSLRAWDGDSGSLLAAPMSGAAVAIWGEDLEDPP
SEQ ID NO 35 Curtobacterium oceanosedimentum                        ADLRENWSLRTWDGDSCARLACPTSGAAVAIWGEDLEAPP
SEQ ID NO 36 Curtobacterium sp. Leaf154 DSM 102595                  ADLRENWSLRTWDGDSGSLLAAPMSGAAVAIWGEDLEDPP SEQ ID NO 20 Curtobacterium oceanosedimentum                        SEALLRWSAPHVTAMIETAAS
SEQ ID NO 33 Curtobacterium flaccumfaciens pv. flaccumfaciens       SDALLRWSAPHVTAMIETAAS
SEQ ID NO 34 Curtobacterium luteum                                  SDALLRWSAPHVTAMIETAAS
SEQ ID NO 35 Curtobacterium oceanosedimentum                        SDALLRWSAPHVLAMIETAGS
SEQ ID NO 36 Curtobacterium sp. Leaf154 DSM 102595                  SDALLRWSAPHVTAMIETAAS
```

Figure 1 continued

Phylogenetic tree of ARAY clade

- SEQ ID NO 34 Curtobacterium luteum
- SEQ ID NO 33 Curtobacterium flaccumfaciens pv flaccumfaciens
- P54WM1 Curtobacterium sp Leaf154
- SEQ ID NO 36 Curtobacterium sp Leaf154 DSM 102595
- A0A1S2HTP0 Curtobacterium sp MCBA15
- A0A1S2HHD6 Curtobacterium sp MCBA15
- A0A0Q5CMZ8 Frondihabitans sp Leaf304
- A0A1D8YJ44 Curtobacterium sp BH 2 1 1
- SEQ ID NO 35 Curtobacterium oceanosedimentum
- A0A175RJL1 Curtobacterium luteum
- SEQ ID NO 20 Curtobacterium oceanosedimentum

SEQUENCE LISTING

<160> NUMBER OF SEQ ID NOS: 46

<210> SEQ ID NO 1
<211> LENGTH: 351
<212> TYPE: PRT
<213> ORGANISM: Actinobacillus pleuropneumoniae

<400> SEQUENCE: 1

```
Met Asp Leu Pro Lys Lys Glu Ser Gly Leu Thr Leu Asp Ile Ala Arg
1               5                   10                  15

Arg Phe Tyr Thr Val Asp Thr Ile Lys Gln Phe Ile Asp Thr Ile His
            20                  25                  30

Gln Ala Gly Gly Thr Phe Leu His Leu His Phe Ser Asp His Glu Asn
        35                  40                  45

Tyr Ala Leu Glu Ser Ser Tyr Leu Glu Gln Arg Glu Glu Asn Ala Thr
    50                  55                  60

Glu Lys Asn Gly Thr Tyr Phe Asn Pro Lys Thr Asn Lys Pro Phe Leu
65                  70                  75                  80

Thr Tyr Lys Gln Leu Asn Glu Ile Ile Tyr Tyr Ala Lys Glu Arg Asn
                85                  90                  95

Ile Glu Ile Val Pro Glu Val Asp Ser Pro Asn His Met Thr Ala Ile
            100                 105                 110

Phe Asp Leu Leu Thr Leu Lys His Gly Lys Glu Tyr Val Lys Gly Leu
        115                 120                 125

Lys Ser Pro Tyr Ile Ala Glu Glu Ile Asp Ile Asn Asn Pro Glu Ala
    130                 135                 140

Val Glu Val Ile Lys Thr Leu Ile Gly Glu Val Ile Tyr Ile Phe Gly
145                 150                 155                 160

His Ser Ser Arg His Phe His Ile Gly Gly Asp Glu Phe Ser Tyr Ala
                165                 170                 175

Val Glu Asn Asn His Glu Phe Ile Arg Tyr Val Asn Thr Leu Asn Asp
            180                 185                 190

Phe Ile Asn Ser Lys Gly Leu Ile Thr Arg Val Trp Asn Asp Gly Leu
        195                 200                 205

Ile Lys Asn Asn Leu Ser Glu Leu Asn Lys Asn Ile Glu Ile Thr Tyr
    210                 215                 220

Trp Ser Tyr Asp Gly Asp Ala Gln Ala Lys Glu Asp Ile Gln Tyr Arg
225                 230                 235                 240

Arg Glu Ile Arg Ala Asp Leu Pro Glu Leu Leu Ala Asn Gly Phe Lys
                245                 250                 255

Val Leu Asn Tyr Asn Ser Tyr Tyr Leu Tyr Phe Val Pro Lys Ser Gly
            260                 265                 270

Ser Asn Ile His Asn Asp Gly Lys Tyr Ala Ala Glu Asp Val Leu Asn
        275                 280                 285

Asn Trp Thr Leu Gly Lys Trp Asp Gly Lys Asn Ser Ser Asn His Val
    290                 295                 300

Gln Asn Thr Gln Asn Ile Ile Gly Ser Ser Leu Ser Ile Trp Gly Glu
305                 310                 315                 320
```

```
Arg Ser Ser Ala Leu Asn Glu Gln Thr Ile Gln Gln Ala Ser Lys Asn
                325                 330                 335

Leu Leu Lys Ala Val Ile Gln Lys Thr Asn Asp Pro Lys Ser His
            340                 345                 350

<210> SEQ ID NO 2
<211> LENGTH: 359
<212> TYPE: PRT
<213> ORGANISM: Aggregatibacter actinomycetemcomitans

<400> SEQUENCE: 2

Cys Val Lys Gly Asn Ser Ile Tyr Pro Gln Lys Thr Ser Thr Lys Gln
1               5                   10                  15

Thr Gly Leu Met Leu Asp Ile Ala Arg His Phe Tyr Ser Pro Glu Val
                20                  25                  30

Ile Lys Ser Phe Ile Asp Thr Ile Ser Leu Ser Gly Gly Asn Phe Leu
            35                  40                  45

His Leu His Phe Ser Asp His Glu Asn Tyr Ala Ile Glu Ser His Leu
        50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Val Lys Tyr Leu Gln Gly Leu Lys Ser Arg Gln Val Asp
130                 135                 140

Asp Glu Ile Asp Ile Thr Asn Ala Asp Ser Ile Thr Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Asn Thr Phe Glu
210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
```

His Lys Thr Asn Gly Asp Glu
            355

<210> SEQ ID NO 3
<211> LENGTH: 367
<212> TYPE: PRT
<213> ORGANISM: Actinobacillus succinogenes

<400> SEQUENCE: 3

Asp Glu Asn Asp Thr Ala Ile Leu Gln Leu Gln Gln Thr Phe Arg Ser
1               5                   10                  15

Ala Glu Leu Ser Gln Asn Lys Glu Thr Gly Leu Ala Leu Asp Ile Ala
            20                  25                  30

Arg His Phe Tyr Pro Val Glu Val Ile Lys Ala Phe Ile Asp Thr Ile
        35                  40                  45

His Asn Ala Gly Gly Thr Phe Leu His Leu His Phe Ser Asp His Glu
    50                  55                  60

Asn Tyr Ala Leu Glu Ser Thr Val Leu Asn Gln Arg Ala Glu Asn Ala
65                  70                  75                  80

Thr Arg Asp Lys Tyr Gly Val Tyr Ile Asn Pro Lys Thr His Lys Pro
                85                  90                  95

Phe Leu Ser Tyr Ala Gln Leu Lys Asp Ile Thr Asp Tyr Ala Lys Asn
            100                 105                 110

Lys Asn Val Glu Leu Val Pro Glu Leu Asp Ser Pro Asn His Met Thr
        115                 120                 125

Ala Ile Phe Asp Leu Leu Glu Lys Glu Arg Gly Lys Pro Tyr Thr Gln
    130                 135                 140

Gln Leu Arg Ser Lys Trp Thr Asp Glu Glu Ile Asp Ile Thr Asn Pro
145                 150                 155                 160

Asp Ser Ile Ala Phe Ile Lys Ser Leu Ile Ala Glu Val Ile Glu Ile
                165                 170                 175

Phe Gly Asp Ser Ser Arg His Phe His Ile Gly Gly Asp Glu Phe Gly
            180                 185                 190

Tyr Gly Thr Asp Asn Asn His Glu Phe Ile Thr Tyr Val Asn Thr Leu
        195                 200                 205

Ala Glu Phe Leu Gln Gln Lys Gly Leu Lys Thr Arg Ile Trp Asn Asp
    210                 215                 220

Gly Leu Ile Lys Ala Thr Ile His Gln Leu Asn Pro Asp Ile Gln Ile
225                 230                 235                 240

Thr Tyr Trp Ser Tyr Asp Gly Asn Pro Gln Asp Glu Gln Glu Glu Arg
                245                 250                 255

Arg Arg Arg Glu Ile Arg Met Ser Met Pro Glu Leu Ile Ala Gln Gly
            260                 265                 270

Phe Ala Val Leu Asn Tyr Asn Ala Tyr Tyr Leu Tyr Phe Thr Pro Gln
        275                 280                 285

Glu Asp Ala Thr Thr Ser His Asp Ser Asn Phe Ala Thr Arg Asp Val
    290                 295                 300

Leu Lys Asn Trp Asp Leu Thr Ile Trp Asp Gly Gln Asn Ser Gln Asn
305                 310                 315                 320

Lys Ile Arg Asp Arg His Lys Ile Met Gly Ser Ala Leu Ser Ile Trp
                325                 330                 335

Gly Glu Lys Ala Gly Ser Leu Arg Ser Asp Ser Ile Gln Lys Tyr Thr
            340                 345                 350

```
Ala Pro Leu Thr Ala Ile Ile Tyr Lys Ser Lys Ile Thr Gly
        355                 360                 365

<210> SEQ ID NO 4
<211> LENGTH: 349
<212> TYPE: PRT
<213> ORGANISM: Neisseria wadsworthii

<400> SEQUENCE: 4

Gln Ser Val Ala Pro Lys Gln Gly Gly Leu Met Leu Asp Thr Ala Arg
1               5                   10                  15

His Phe Tyr Pro Thr Asn Val Ile Lys Asp Phe Ile Asp Thr Ile Ala
            20                  25                  30

Lys Ser Gly Gly Asn Phe Leu His Leu His Phe Ser Asp His Glu Asn
        35                  40                  45

Tyr Ala Leu Glu Ser His Ile Leu Asn Gln Arg Ala Ala Asp Ala Thr
    50                  55                  60

Arg Asn Ala Asp Gly Val Tyr Ile Asn Pro Val Thr Gly Lys Pro Phe
65                  70                  75                  80

Leu Ser Phe Glu Gln Leu Glu Ile Lys Ala Tyr Ala Lys Ser Lys
                85                  90                  95

Asn Ile Glu Leu Ile Pro Glu Val Asp Ser Pro Asn His Met Thr Thr
            100                 105                 110

Ile Phe Thr Leu Leu Glu Ala His Arg Gly Lys Asp Phe Val Asn Lys
        115                 120                 125

Ile Lys Ser Lys Tyr Ser Asp Glu Glu Ile Asn Ile Thr Asn Pro Glu
    130                 135                 140

Ser Ile Ala Phe Met Lys Ser Leu Ile Gly Glu Val Ala Asp Ala Phe
145                 150                 155                 160

Gly Asp Ser Ser Arg His Phe His Ile Gly Gly Asp Glu Phe Gly Tyr
                165                 170                 175

Ser Val Asp Ser Asn His Glu Phe Ile Ala Tyr Ala Asn Asp Leu Ser
            180                 185                 190

Ala Phe Leu Lys Gln Lys Gly Leu Thr Thr Arg Ile Trp Asn Asp Gly
        195                 200                 205

Ile Ile Lys Ala Thr Val Asp Lys Leu Asn Pro Glu Ile Gln Val Thr
    210                 215                 220

Tyr Trp Ser Tyr Asp Gly Asp Val Gln Asn Lys Gln Ala Ser Gln Glu
225                 230                 235                 240

Arg Arg Arg Ile Arg Thr Ser Met Pro Asp Leu Ile Glu Lys Gly Phe
                245                 250                 255

Ser Val Leu Asn Tyr Asn Ser Tyr Tyr Leu Tyr Val Asn Pro Lys Gln
            260                 265                 270

Glu Trp Gly Thr Ser Tyr Asn Ser Asp Phe Ala Thr Arg Asp Ile Ile
        275                 280                 285

Asn Arg Trp Asn Leu Gly Val Trp Asp Gly Glu Asn Gln Asn Ala
    290                 295                 300

Val Lys Asn Thr Asp Lys Ile Met Gly Ala Ala Leu Ala Ile Trp Gly
305                 310                 315                 320

Glu Asn Ala Gly Ser Met Ser Lys Thr Ile Gln Lys Tyr Thr Ala
                325                 330                 335

Gly Leu Leu Glu Ser Ile Ile Arg Lys Thr His Ala Glu
        340                 345

<210> SEQ ID NO 5
```

<211> LENGTH: 352
<212> TYPE: PRT
<213> ORGANISM: Actinobacillus capsulatus

<400> SEQUENCE: 5

Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Leu Glu Ala Asn Ala
    50                  55                  60

Ile Val Lys Asp Gly Thr Tyr Tyr Asn Pro Thr Thr Asn Lys Pro Phe
65                  70                  75                  80

Leu Thr Tyr Lys Gln Ile Asn Asp Ile Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Ser Lys Asp Tyr Val Lys Arg
        115                 120                 125

Leu Lys Ser Lys Met Asn Asp Glu Glu Ile Asp Ile Thr Asn Leu Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Thr Tyr Val Asn Thr Leu Asn
            180                 185                 190

Gln Phe Ile Asn Asn Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Glu Ser Gln Asp Ile Ala Glu
225                 230                 235                 240

Arg Arg Lys Ile Arg Val Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys His Ala Thr Glu Asp Val Leu
        275                 280                 285

Lys Asn Trp Lys Leu Gly Leu Trp Asp Gly Gln Asn Lys Glu Asn Ile
    290                 295                 300

Val Glu Asn Thr Lys Asn Ile Ile Gly Ser Ser Leu Ser Ile Trp Gly
305                 310                 315                 320

Glu His Ser Gly Ser Leu Ser Ser Ala Val Ile Glu Glu Ser Thr Gln
                325                 330                 335

Glu Leu Leu Lys Ala Val Ile Gln Lys Thr Asn Asp Pro Lys Ser His
            340                 345                 350

<210> SEQ ID NO 6
<211> LENGTH: 324
<212> TYPE: PRT
<213> ORGANISM: Terribacillus goriensis

<400> SEQUENCE: 6

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
            20                  25                  30

Gly Asp Tyr Leu Gln Leu His Phe Ser Asp Asn Glu Arg Tyr Ala Ile
            35                  40                  45

Ala Ser Glu Phe Leu Gly Gln Asn Gly Glu Asn Pro Asn Ser Thr Tyr
50                  55                  60

Leu Thr Lys Lys Glu Leu Leu Ser Leu Ile Ala Tyr Ser Asn Asp Arg
65                  70                  75                  80

Asp Ile Met Val Ile Pro Asp Ile Asp Leu Pro Ala His Ser Arg Gly
                85                  90                  95

Trp Leu Asn Ile Met Lys Glu Lys Asp Ser Gly Leu Tyr Thr Asp Ile
                100                 105                 110

Val Thr Asp Tyr Ser Glu Asp Thr Leu Asp Tyr His Asn Asn Ala Val
            115                 120                 125

Ala Leu Tyr Thr Ala Asn Gln Leu Leu Asp Glu Val Leu Asp Leu Phe
            130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
                165                 170                 175

Asn Gln Ile Ala Glu Thr Ala Lys Ala Ser Asn Tyr Lys Pro Gln Met
                180                 185                 190

Trp Asn Asp Ser Ile Thr Pro Glu Gly Ile Gln Asn Leu Asp Arg Ser
                195                 200                 205

Phe Ser Ile Leu Tyr Trp Lys Gln Ser Thr Leu Ser Asn Gly Ala Gln
210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
            245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
            275                 280                 285

Asn Val Lys Gly Ser Ser Leu Val Phe Trp Gly Glu His Ala Asn Asp
            290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 7
<211> LENGTH: 324
<212> TYPE: PRT
<213> ORGANISM: Terribacillus saccharophilus

<400> SEQUENCE: 7

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
            35                  40                  45

Ala Ser Glu Phe Leu Gly Gln Asn Ser Glu Asn Pro Asn Ser Ala Tyr
            50                  55                  60

Leu Thr Lys Lys Glu Leu Leu Ser Leu Ile Ala Tyr Ser Asn Asp Arg
 65                  70                  75                  80

Asn Ile Met Val Ile Pro Asp Ile Asp Leu Pro Ala His Ser Lys Gly
                85                  90                  95

Trp Leu Asn Ile Met Lys Glu Lys Asp Ser Gly Leu Tyr Thr Asp Ile
                100                 105                 110

Val Thr Asp Tyr Ser Glu Asp Thr Leu Asp Tyr His Asn Asn Ala Val
            115                 120                 125

Ala Leu Tyr Thr Ala Asn Gln Leu Leu Asp Glu Val Leu Asp Leu Phe
            130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
                180                 185                 190

Trp Asn Asp Ser Ile Thr Pro Glu Gly Ile Gln Asn Leu Asp Arg Ser
            195                 200                 205

Phe Ser Ile Leu Tyr Trp Lys Gln Ser Thr Leu Ser Asn Gly Ala Gln
            210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
                260                 265                 270

Asn Lys Phe Phe Tyr Ile Ser Asp Tyr Tyr Lys Gln Val Asp Thr Pro
            275                 280                 285

Asn Val Lys Gly Ser Ser Leu Val Phe Trp Gly Glu His Ala Asn Asp
            290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 8
<211> LENGTH: 325
<212> TYPE: PRT
<213> ORGANISM: Curtobacterium oceanosedimentum

<400> SEQUENCE: 8

Glu Thr Gly Val Met Leu Asp Val Ala Arg Ala Tyr Tyr Pro Val Ser
 1                5                  10                  15

Leu Ile Glu Gln Tyr Val Asp Leu Leu Ala Glu His Gly Gly Gly Phe
            20                  25                  30

Leu His Leu His Leu Thr Asp Asp Gln Asn Val Gly Ile Glu Ser Ala
            35                  40                  45

Val Leu Gly Gln Thr Pro Ala Asn Ala Val Leu Arg Asn Gly Val Tyr
 50                  55                  60

Thr Ser Arg Val Thr Gly Arg Pro Phe Leu Ser Ala Ala Gln Ala Arg
 65                  70                  75                  80

Ala Ile Ser Ala Tyr Ala Ala Lys Arg Gly Ile Ala Ile Val Pro Glu
                85                  90                  95

```
Val Asp Ser Pro Gly His Met Ala Ala Ala Phe Ala Leu Leu Glu Ala
            100                 105                 110

Arg His Gly Ala Thr Trp Val Asp Arg Ile Arg Ser Gly Glu Ser Glu
            115                 120                 125

Leu Asp Thr Ser Val Pro Glu Ser Ala Thr Leu Ala Ala Glu Leu Leu
            130                 135                 140

Arg Glu Val Thr Gln Thr Phe Pro Ser Ser Arg Thr Val His Ile Gly
145                 150                 155                 160

Gly Asp Glu Trp Gly Ala Asp Val Ser Ala Asp Glu Arg Val Gly Trp
                165                 170                 175

Met Asn Ala Met Ala Ala Ile Gly Asp Arg Glu Val Trp Ala Trp
            180                 185                 190

Asn Asp Gly Ile Asp Arg Ala Ser Val Gly Arg Leu Asp Pro Arg Ile
            195                 200                 205

His Val Thr Tyr Trp Ser Phe Asp Gly Asp Thr Glu Asp Ala Ala Glu
            210                 215                 220

Arg Arg Glu Arg Arg Ala Arg Arg Ala Ser Ala Thr Asp Leu Gln Arg
225                 230                 235                 240

Ala Gly Ile Asp Leu Leu Asn Tyr Asn Ser Tyr Tyr Leu Tyr Glu Val
                245                 250                 255

Pro Thr Asp Leu Asp Pro Ala Asp Ser Glu Tyr Thr Val Ala Asp Leu
            260                 265                 270

Arg Glu His Trp Ser Leu Arg Ala Trp Asp Gly Asp Ser Gly Ala Arg
            275                 280                 285

Leu Ala Ala Pro Met Ser Gly Ala Ala Val Ala Ile Trp Gly Glu Asp
            290                 295                 300

Leu Asp Gly Ala Pro Ser Glu Ala Leu Leu Arg Trp Ser Ala Pro His
305                 310                 315                 320

Val Thr Ala Met Ile
                325

<210> SEQ ID NO 9
<211> LENGTH: 378
<212> TYPE: PRT
<213> ORGANISM: Actinobacillus capsulatus

<400> SEQUENCE: 9

Met Lys Lys Ile Ile Ser Leu Leu Thr Leu Ile Phe Ile Gly Leu Leu
1               5                   10                  15

Ser Ser Cys Ser Ser Ser Thr Val Asn Ala Met Asn His Ser Gln Ile
            20                  25                  30

Lys Glu Ala Gly Leu Thr Leu Asp Ile Ala Arg Arg Phe Tyr Pro Val
            35                  40                  45

Glu Thr Ile Lys Gln Phe Ile Asp Thr Ile His His Ala Gly Gly Thr
50                  55                  60

Phe Leu His Leu His Phe Ser Asp His Glu Asn Tyr Ala Leu Glu Ser
65                  70                  75                  80

Thr Tyr Leu Asp Gln Leu Glu Ala Asn Ala Ile Val Lys Asp Gly Thr
                85                  90                  95

Tyr Tyr Asn Pro Thr Thr Asn Lys Pro Phe Leu Thr Tyr Lys Gln Ile
            100                 105                 110

Asn Asp Ile Ile Tyr Tyr Ala Lys Ser Lys Asn Ile Glu Leu Val Pro
            115                 120                 125

Glu Val Asp Thr Pro Asn His Met Thr Ala Ile Phe Arg Leu Leu Glu
```

```
                    130                 135                 140
Ala Lys His Ser Lys Asp Tyr Val Lys Arg Leu Lys Ser Lys Met Asn
145                 150                 155                 160

Asp Glu Glu Ile Asp Ile Thr Asn Leu Glu Ser Ile Glu Val Ile Lys
                    165                 170                 175

Thr Leu Ile Ala Glu Val Ile Tyr Ile Phe Gly His Ala Ser Glu His
                180                 185                 190

Phe His Ile Gly Gly Asp Glu Phe Gly Tyr Ser Val Glu Thr Asn His
            195                 200                 205

Glu Phe Ile Thr Tyr Val Asn Thr Leu Asn Gln Phe Ile Asn Asn Lys
        210                 215                 220

Gly Lys Ile Thr Arg Ile Trp Asn Asp Gly Leu Ile Lys Asn Asn Leu
225                 230                 235                 240

Asn Gln Leu Asn Lys Asn Val Glu Ile Thr Tyr Trp Ser Tyr Asp Gly
                245                 250                 255

Asp Ala Gln Glu Ser Gln Asp Ile Ala Glu Arg Arg Lys Ile Arg Val
                260                 265                 270

Asn Leu Pro Glu Leu Leu Glu Asn Gly Phe Lys Val Leu Asn Tyr Asn
            275                 280                 285

Ser Tyr Tyr Leu Tyr Phe Val Pro Lys Gly Asn Ala Asn Ile Thr His
        290                 295                 300

Asp Ser Lys His Ala Thr Glu Asp Val Leu Lys Asn Trp Lys Leu Gly
305                 310                 315                 320

Leu Trp Asp Gly Gln Asn Lys Glu Asn Ile Val Glu Asn Thr Lys Asn
                325                 330                 335

Ile Ile Gly Ser Ser Leu Ser Ile Trp Gly Glu His Ser Gly Ser Leu
                340                 345                 350

Ser Ser Ala Val Ile Glu Glu Ser Thr Gln Glu Leu Leu Lys Ala Val
            355                 360                 365

Ile Gln Lys Thr Asn Asp Pro Lys Ser His
        370                 375

<210> SEQ ID NO 10
<211> LENGTH: 349
<212> TYPE: PRT
<213> ORGANISM: Terribacillus goriensis

<400> SEQUENCE: 10

Met Leu Ile Lys Phe Leu Ser Ile Thr Thr Val Ser Ile Leu Leu Phe
1               5                   10                  15

Leu Thr Met Ser Asn Thr Ala Gln Ala Gln Asp Gln Glu Lys Gly Ile
                20                  25                  30

Thr Ile Asp Ile Ser Arg Lys Tyr Tyr Ser Ile Glu Thr Leu Lys Ser
            35                  40                  45

Ile Ile Asp Glu Ile Ser Ala Asn Gly Gly Asp Tyr Leu Gln Leu His
        50                  55                  60

Phe Ser Asp Asn Glu Arg Tyr Ala Ile Ala Ser Glu Phe Leu Gly Gln
65                  70                  75                  80

Asn Gly Glu Asn Pro Asn Ser Thr Tyr Leu Thr Lys Lys Glu Leu Leu
                85                  90                  95

Ser Leu Ile Ala Tyr Ser Asn Asp Arg Asp Ile Met Val Ile Pro Asp
            100                 105                 110

Ile Asp Leu Pro Ala His Ser Arg Gly Trp Leu Asn Ile Met Lys Glu
        115                 120                 125
```

-continued

```
Lys Asp Ser Gly Leu Tyr Thr Asp Ile Val Thr Asp Tyr Ser Glu Asp
        130                 135                 140
Thr Leu Asp Tyr His Asn Asn Ala Val Ala Leu Tyr Thr Ala Asn Gln
145                 150                 155                 160
Leu Leu Asp Glu Val Leu Asp Leu Phe Tyr Gln Pro Lys Phe Ala Gly
                165                 170                 175
Lys Gln Arg Ile Val Leu Gly Gly Asp Glu Val Pro Gly Ser Gly Val
            180                 185                 190
His Gln Thr Asp Phe Ile Arg Phe Met Asn Gln Ile Ala Glu Thr Ala
        195                 200                 205
Lys Ala Ser Asn Tyr Lys Pro Gln Met Trp Asn Asp Ser Ile Thr Pro
210                 215                 220
Glu Gly Ile Gln Asn Leu Asp Arg Ser Phe Ser Ile Leu Tyr Trp Lys
225                 230                 235                 240
Gln Ser Thr Leu Ser Asn Gly Ala Gln Gly Leu Asp Val Gln Asp Phe
                245                 250                 255
Glu Glu Asn Gly Leu Ser Val Tyr Asn Tyr Asn Ala Tyr Ser Leu Tyr
            260                 265                 270
Phe Leu Pro Ala Thr Arg Phe Thr Gln Glu Asp Ile Thr Glu Gln Ile
        275                 280                 285
Asp Tyr Met Lys Trp Ala Tyr Ala Tyr Asn Lys Phe Phe Tyr Ile Ser
290                 295                 300
Asp Tyr Tyr Lys Gln Val Asp Thr Ser Asn Val Lys Gly Ser Ser Leu
305                 310                 315                 320
Val Phe Trp Gly Glu His Ala Asn Asp Leu Ser Gln Glu Gly Leu Leu
                325                 330                 335
Lys Gln Glu Lys Pro Leu Ile Gln Asn Phe Leu Gly Leu
            340                 345

<210> SEQ ID NO 11
<211> LENGTH: 365
<212> TYPE: PRT
<213> ORGANISM: Terribacillus saccharophilus

<400> SEQUENCE: 11

Met Val Ser Arg Thr Met Leu Phe Ile Lys Arg Glu Lys Gly Lys Thr
1               5                   10                  15
Val Leu Ile Lys Phe Leu Ser Ile Thr Thr Val Ser Ile Leu Leu Phe
            20                  25                  30
Leu Thr Met Ala Asn Thr Ala Gln Ala Gln Asp Gln Glu Lys Gly Ile
        35                  40                  45
Thr Ile Asp Ile Ser Arg Lys Tyr Tyr Ser Ile Lys Thr Leu Lys Ala
    50                  55                  60
Ile Val Asp Glu Ile Ser Ala Asn Gly Gly Asp Tyr Leu Gln Leu His
65                  70                  75                  80
Phe Ser Asp Asn Glu Ser Tyr Ala Ile Ala Ser Glu Phe Leu Gly Gln
                85                  90                  95
Asn Ser Glu Asn Pro Asn Ser Ala Tyr Leu Thr Lys Lys Glu Leu Leu
            100                 105                 110
Ser Leu Ile Ala Tyr Ser Asn Asp Arg Asn Ile Met Val Ile Pro Asp
        115                 120                 125
Ile Asp Leu Pro Ala His Ser Lys Gly Trp Leu Asn Ile Met Lys Glu
    130                 135                 140
Lys Asp Ser Gly Leu Tyr Thr Asp Ile Val Thr Asp Tyr Ser Glu Asp
145                 150                 155                 160
```

```
Thr Leu Asp Tyr His Asn Asn Ala Val Ala Leu Tyr Thr Ala Asn Gln
            165                 170                 175

Leu Leu Asp Glu Val Leu Asp Leu Phe Tyr Gln Pro Lys Phe Ala Gly
            180                 185                 190

Lys Gln Arg Ile Val Leu Gly Gly Asp Glu Val Pro Gly Ser Gly Ala
            195                 200                 205

His Gln Thr Asp Phe Ile Arg Phe Met Asn Gln Ile Ala Lys Thr Ala
            210                 215                 220

Lys Ala Ser Asn Tyr Glu Pro Gln Met Trp Asn Asp Ser Ile Thr Pro
225                 230                 235                 240

Glu Gly Ile Gln Asn Leu Asp Arg Ser Phe Ser Ile Leu Tyr Trp Lys
            245                 250                 255

Gln Ser Thr Leu Ser Asn Gly Ala Gln Ser Leu Asp Val Gln Asp Phe
            260                 265                 270

Glu Glu Asn Gly Leu Ser Val Tyr Asn Tyr Asn Ala Tyr Ser Leu Tyr
            275                 280                 285

Phe Leu Pro Ser Thr Arg Phe Thr Gln Glu Asp Ile Thr Glu Gln Ile
            290                 295                 300

Asp Tyr Met Lys Trp Ala Tyr Ala Tyr Asn Lys Phe Phe Tyr Ile Ser
305                 310                 315                 320

Asp Tyr Tyr Lys Gln Val Asp Thr Pro Asn Val Lys Gly Ser Ser Leu
            325                 330                 335

Val Phe Trp Gly Glu His Ala Asn Asp Leu Ser Gln Glu Gly Leu Leu
            340                 345                 350

Lys Gln Glu Lys Pro Leu Ile Gln Asn Phe Leu Gly Leu
            355                 360                 365

<210> SEQ ID NO 12
<211> LENGTH: 485
<212> TYPE: PRT
<213> ORGANISM: Curtobacterium oceanosedimentum

<400> SEQUENCE: 12

Met Ile Ala Gly Ala Val Val Val Thr Ala Ala Ala Val Leu Val
1               5                   10                  15

Gly Val Gly Ala Val Ala Gly Pro Ala Asp Arg Asn Thr Ser Ala Ala
            20                  25                  30

Glu Ala Ala Val Thr Ser Ile Ala Pro Arg Ala Thr Ile Thr Gly Val
            35                  40                  45

Ala Ala Ile Ser Ala Ala Thr Ser Ser Arg Thr Thr Val Arg Thr Thr
        50                  55                  60

Leu Thr Leu Glu Asn Arg Ser Gly Glu Arg Glu Ser Ala Ala Asp Ala
65                  70                  75                  80

Trp Leu Tyr Leu Ala Gly Gly Ala Arg Tyr Ala Leu Gly His Ala
            85                  90                  95

Pro Val Arg Ala Leu Ala Ala Gly Ala Arg Ala Thr Val Arg Thr Thr
            100                 105                 110

Leu Arg Val Pro Ser Arg Ala Pro Ala Gly Lys Tyr Ala Val Leu Ala
            115                 120                 125

Cys Ala Gly Pro Tyr Ser Lys Gln Ala Cys Arg Thr Ser Gly Thr Thr
            130                 135                 140

Val Thr Val Gly Thr Ala Ala Arg Ala Arg Pro Glu Thr Gly Val Met
145                 150                 155                 160

Leu Asp Val Ala Arg Ala Tyr Tyr Pro Val Ser Leu Ile Glu Gln Tyr
```

```
                165                 170                 175
Val Asp Leu Leu Ala Glu His Gly Gly Gly Phe Leu His Leu His Leu
            180                 185                 190

Thr Asp Asp Gln Asn Val Gly Ile Glu Ser Ala Val Leu Gly Gln Thr
            195                 200                 205

Pro Ala Asn Ala Val Leu Arg Asn Gly Val Tyr Thr Ser Arg Val Thr
210                 215                 220

Gly Arg Pro Phe Leu Ser Ala Gln Ala Arg Ala Ile Ser Ala Tyr
225                 230                 235                 240

Ala Ala Lys Arg Gly Ile Ala Ile Val Pro Glu Val Asp Ser Pro Gly
                245                 250                 255

His Met Ala Ala Ala Phe Ala Leu Leu Glu Ala Arg His Gly Ala Thr
            260                 265                 270

Trp Val Asp Arg Ile Arg Ser Gly Glu Ser Glu Leu Asp Thr Ser Val
            275                 280                 285

Pro Glu Ser Ala Thr Leu Ala Ala Glu Leu Leu Arg Glu Val Thr Gln
            290                 295                 300

Thr Phe Pro Ser Ser Arg Thr Val His Ile Gly Gly Asp Glu Trp Gly
305                 310                 315                 320

Ala Asp Val Ser Ala Asp Glu Arg Val Gly Trp Met Asn Ala Met Ala
                325                 330                 335

Ala Ala Ile Gly Asp Arg Glu Val Trp Ala Trp Asn Asp Gly Ile Asp
            340                 345                 350

Arg Ala Ser Val Gly Arg Leu Asp Pro Arg Ile His Val Thr Tyr Trp
            355                 360                 365

Ser Phe Asp Gly Asp Thr Glu Asp Ala Ala Glu Arg Glu Arg Arg
370                 375                 380

Ala Arg Arg Ala Ser Ala Thr Asp Leu Gln Arg Ala Gly Ile Asp Leu
385                 390                 395                 400

Leu Asn Tyr Asn Ser Tyr Tyr Leu Tyr Glu Val Pro Thr Asp Leu Asp
                405                 410                 415

Pro Ala Asp Ser Glu Tyr Thr Val Ala Asp Leu Arg Glu His Trp Ser
            420                 425                 430

Leu Arg Ala Trp Asp Gly Asp Ser Gly Ala Arg Leu Ala Ala Pro Met
            435                 440                 445

Ser Gly Ala Ala Val Ala Ile Trp Gly Glu Asp Leu Asp Gly Ala Pro
            450                 455                 460

Ser Glu Ala Leu Leu Arg Trp Ser Ala Pro His Val Thr Ala Met Ile
465                 470                 475                 480

Glu Thr Ala Ala Ser
            485

<210> SEQ ID NO 13
<211> LENGTH: 1134
<212> TYPE: DNA
<213> ORGANISM: Actinobacillus capsulatus

<400> SEQUENCE: 13
atgaagaaga tcatctctct tcttacgctt atcttcatcg gccttctttc ttcttgctca        60
tcatctacag taaacgcgat gaaccactct caaatcaagg aagctggcct tactttagac      120
attgctcgtc gcttctaccc agttgagaca atcaagcaat tcatcgacac tatccaccat      180
gctggtggca cattccttca ccttcacttc tcagaccacg agaactacgc gcttgagtct      240
acgtaccttg accaacttga ggcgaacgcg atcgttaagg acggcacata ctacaaccca      300
```

```
acgacaaaca agcctttcct tacttacaag caaatcaacg acatcatcta ctacgcgaag    360
tctaagaaca tcgagcttgt acctgaggta gacacaccga accacatgac agcgatcttc    420
cgccttcttg aggcgaagca cagcaaggac tacgtaaagc gccttaagtc aaagatgaac    480
gacgaggaga tcgacatcac taaccttgag tctatcgagg ttatcaagac tcttatcgct    540
gaggttatct acatcttcgg ccacgcgagc gagcacttcc acattggtgg cgacgagttc    600
ggctactcag ttgagacgaa ccacgagttc atcacttacg ttaacacgct taaccagttc    660
atcaacaaca agggcaagat cacgcgcatc tggaacgacg gccttatcaa gaacaacctt    720
aaccaactta acaagaacgt tgagatcacg tactggtctt acgacggcga cgcgcaagag    780
tcacaagaca tcgcggaacg tcgcaagatc cgcgtaaacc ttcctgagct tcttgagaac    840
ggcttcaagg ttcttaacta caactcttac tacctttact tcgtacctaa gggcaacgcg    900
aacatcacgc acgactctaa gcacgcgact gaggacgttc ttaagaactg gaagcttggc    960
ctttgggacg gccaaaacaa ggagaacatc gttgagaaca cgaagaacat catcggctca   1020
tctctttcta tctggggtga gcactctggc tcactttcat ctgcggttat cgaggagtct   1080
acgcaagagc ttcttaaggc ggttatccaa aagacaaacg acccaaagtc tcac         1134

<210> SEQ ID NO 14
<211> LENGTH: 1047
<212> TYPE: DNA
<213> ORGANISM: Terribacillus goriensis

<400> SEQUENCE: 14
atgcttatca agttcctttc tatcacgaca gtttcaatcc ttcttttcct tacgatgtct    60
aacactgcgc aagcgcaaga ccaagagaag ggcatcacaa tcgacatctc tcgcaagtac   120
tactctatcg agacacttaa gtctatcatc gacgagatct cagcgaatgg tggcgactac   180
cttcaacttc atttctctga caacgagcgc tacgcgatcg cgtcagagtt ccttggccaa   240
aacggcgaga acccaaactc tacttacctt acaaagaagg agcttctttc tcttatcgcg   300
tactctaacg accgcgacat catggtaatc ccagacatcg accttccagc gcattctcgt   360
ggctggctta acatcatgaa ggagaaggac tcaggccttt acactgacat cgtaacggac   420
tactctgagg acacacttga ctaccataac aacgctgtag cgctttacac agcaaaccaa   480
cttcttgacg aggtacttga cctttctac caaccgaagt tgctggcaa gcagcgcatc   540 gtacttggtg gcgacgaggt tcctggctct ggcgtacacc agactgactt catccgcttc   600
atgaaccaaa tcgcggagac tgcgaaggct tctaactaca agccacaaat gtggaacgac   660
tctatcacac tgagggcat ccaaaacctt gaccgctcat tctctatcct ttactggaag   720
caatctacac ttagcaatgg tgcgcaaggc cttgacgtac aagacttcga ggagaacggc   780
cttagcgttt acaactacaa tgcgtactca ctttacttcc ttcctgcgac acgcttcact   840
caagaggaca tcactgagca aatcgactac atgaagtggg cgtatgcgta caacaagttc   900
ttctacatct ctgactacta caagcaagta gacacaagca acgttaaggg ctcttctctt   960
gtattctggg gtgagcatgc gaacgacctt agccaagagg gccttcttaa gcaagagaag  1020
ccacttatcc aaaacttcct tggcctt                                     1047

<210> SEQ ID NO 15
<211> LENGTH: 1095
<212> TYPE: DNA
<213> ORGANISM: Terribacillus saccharophilus
```

<400> SEQUENCE: 15

```
atggtatctc gcacgatgct tttcatcaag cgcgagaagg gcaagacggt tcttatcaag    60
ttcctttcta tcacgacagt atctatcctt cttttcctta cgatggcgaa cactgcgcaa   120
gcgcaagacc aagagaaggg catcacaatc gacatctctc gcaagtacta cagcatcaag   180
acgcttaagg cgatcgttga cgagatctca gcgaatggtg gcgactacct tcaacttcac   240
ttctctgaca acgagagcta cgcgatcgcg tctgagttcc ttggccaaaa ctctgagaac   300
ccaaactctg cgtaccttac aaagaaggag cttctttcac ttatcgcgta ctctaacgac   360
cgcaacatca tggttatccc ggacatcgac cttcctgcgc actcaaaggg ctggcttaac   420
atcatgaagg agaaggactc tggcctttac acagacatcg taactgacta ctcagaagac   480
actcttgact accacaacaa cgcggttgcg ctttacacgg cgaaccaact tcttgacgag   540
gttcttgacc ttttctacca acctaagttt gctggcaagc aacgcatcgt tcttggtggc   600
gacgaggttc ctggctctgg tgcgcaccaa actgacttca tccgcttcat gaaccagatc   660
gcgaagacag cgaaggcgtc taactacgag ccacaaatgt ggaacgacag catcactcct   720
gagggcatcc aaaaccttga ccgctctttc tctatccttt actggaagca atcaacgctt   780
tcaaatggtg cgcaatctct tgacgtacaa gacttcgagg agaacggcct ttcagtttac   840
aactacaacg cttacagcct ttacttcctt cctagcactc gcttcacgca agaggacatc   900
acggagcaaa tcgactacat gaagtgggcg tatgcgtaca acaagttctt ctacatctct   960
gactactaca gcaagtagac acaccaaac gtaaagggct catctcttgt attctggggt  1020
gagcacgcga acgaccttc tcaagagggc cttcttaagc aagagaagcc acttatccaa  1080
aacttccttg gcctt                                                    1095
```

<210> SEQ ID NO 16
<211> LENGTH: 1455
<212> TYPE: DNA
<213> ORGANISM: Curtobacterium oceanosedimentum

<400> SEQUENCE: 16

```
atgatcgctg gtgcggtagt tgtagttaca gcggctgctg ttcttgttgg cgttggtgct    60
gttgctggcc ctgcagaccg caatacttct gctgcggaag ctgcggtaac gtcaatcgct   120
ccgcgtgcaa ctattacagg agttgcagca atctctgctg ctactagctc acgtacaaca   180
gttcgcacta cttaacatt agaaaaccgt tctggtgagc gtgaatctgc agctgatgct   240
tggctttatc ttgcaggagg cggagctcgt tatgctcttg gtcatgctcc tgttcgcgca   300
cttgcagctg gagctcgtgc tacagttcgc acaacacttc gcgttccatc acgtgcgcct   360
gctggcaaat acgctgttct tgcttgtgcc ggaccatact ctaaacaagc atgtcgcact   420
agcggtacta ctgttacagt tggcactgcg gctcgtgctc gccctgagac gggagttatg   480
ttagatgttg ctcgtgcgta ttacccggtt agccttatcg aacagtacgt tgatttgctt   540
gcagaacatg gtggtggctt tttgcattta catcttactg acgaccaaaa tgttggtatt   600
gaatctgcgg tacttggcca aacacctgct aacgctgtac ttcgtaatgg cgtatacact   660
tctcgtgtta ctggtcgtcc tttcttatct gctgcgcaag ctcgtgctat tagcgcttat   720
gctgctaaac gtggtattgc gatcgttcct gaggttgatt ctccaggaca catggctgca   780
gcttttgcac ttttagaggc acgccatggt gctacatggg ttgatcgtat ccgttctggt   840
gagtcagaat tagacacttc tgttccggaa tcagctacgt tagcggcaga attgcttcgt   900
gaagtaactc agactttccc aagctctcgt actgttcaca ttggtggtga cgaatgggga   960
```

```
gcagacgttt ctgctgacga gcgcgttggt tggatgaacg ctatggctgc tgctatcggt    1020
gaccgtgaag tttgggcatg gaacgacggc atcgatcgcg ctagcgtagg tcgtttagat    1080
ccacgtattc atgtaactta ttggtcattc gacggtgaca ctgaagatgc agcggaacgt    1140
cgtgagcgtc gcgcacgccg tgcatctgcc acagatcttc aacgtgctgg aattgacctt    1200
cttaactaca acagctatta cttatacgaa gtacctactg acttagaccc tgcggattct    1260
gagtatacag ttgcagatct tcgtgaacac tggagccttc gtgcatggga cggagactct    1320
ggagctcgct tagcagctcc tatgagcggt gctgcagttg cgatctgggg tgaggacctt    1380
gatggcgctc catctgaagc attgttgcgt tggtcagcac cacacgttac tgcaatgatc    1440
gagactgctg catca                                                    1455
```

<210> SEQ ID NO 17
<211> LENGTH: 352
<212> TYPE: PRT
<213> ORGANISM: Actinobacillus capsulatus

<400> SEQUENCE: 17

```
Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Leu Glu Ala Asn Ala
    50                  55                  60

Ile Val Lys Asp Gly Thr Tyr Tyr Asn Pro Thr Thr Asn Lys Pro Phe
65                  70                  75                  80

Leu Thr Tyr Lys Gln Ile Asn Asp Ile Ile Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Ser Lys Asp Tyr Val Lys Arg
        115                 120                 125

Leu Lys Ser Lys Met Asn Asp Glu Glu Ile Asp Ile Thr Asn Leu Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Thr Tyr Val Asn Thr Leu Asn
            180                 185                 190

Gln Phe Ile Asn Asn Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Glu Ser Gln Asp Ile Ala Glu
225                 230                 235                 240

Arg Arg Lys Ile Arg Val Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys His Ala Thr Glu Asp Val Leu
```

```
                275                 280                 285
Lys Asn Trp Lys Leu Gly Leu Trp Asp Gly Gln Asn Lys Glu Asn Ile
            290                 295                 300
Val Glu Asn Thr Lys Asn Ile Ile Gly Ser Ser Leu Ser Ile Trp Gly
305                 310                 315                 320
Glu His Ser Gly Ser Leu Ser Ser Ala Val Ile Glu Glu Ser Thr Gln
                325                 330                 335
Glu Leu Leu Lys Ala Val Ile Gln Lys Thr Asn Asp Pro Lys Ser His
            340                 345                 350
```

<210> SEQ ID NO 18
<211> LENGTH: 324
<212> TYPE: PRT
<213> ORGANISM: Terribacillus goriensis

<400> SEQUENCE: 18

```
Gln Asp Gln Glu Lys Gly Ile Thr Ile Asp Ile Ser Arg Lys Tyr Tyr
1               5                   10                  15
Ser Ile Glu Thr Leu Lys Ser Ile Ile Asp Glu Ile Ser Ala Asn Gly
                20                  25                  30
Gly Asp Tyr Leu Gln Leu His Phe Ser Asp Asn Glu Arg Tyr Ala Ile
            35                  40                  45
Ala Ser Glu Phe Leu Gly Gln Asn Gly Glu Asn Pro Asn Ser Thr Tyr
        50                  55                  60
Leu Thr Lys Lys Glu Leu Leu Ser Leu Ile Ala Tyr Ser Asn Asp Arg
65                  70                  75                  80
Asp Ile Met Val Ile Pro Asp Ile Asp Leu Pro Ala His Ser Arg Gly
                85                  90                  95
Trp Leu Asn Ile Met Lys Glu Lys Asp Ser Gly Leu Tyr Thr Asp Ile
            100                 105                 110
Val Thr Asp Tyr Ser Glu Asp Thr Leu Asp Tyr His Asn Asn Ala Val
        115                 120                 125
Ala Leu Tyr Thr Ala Asn Gln Leu Leu Asp Glu Val Leu Asp Leu Phe
130                 135                 140
Tyr Gln Pro Lys Phe Ala Gly Lys Gln Arg Ile Val Leu Gly Gly Asp
145                 150                 155                 160
Glu Val Pro Gly Ser Gly Val His Gln Thr Asp Phe Ile Arg Phe Met
                165                 170                 175
Asn Gln Ile Ala Glu Thr Ala Lys Ala Ser Asn Tyr Lys Pro Gln Met
            180                 185                 190
Trp Asn Asp Ser Ile Thr Pro Glu Gly Ile Gln Asn Leu Asp Arg Ser
        195                 200                 205
Phe Ser Ile Leu Tyr Trp Lys Gln Ser Thr Leu Ser Asn Gly Ala Gln
210                 215                 220
Gly Leu Asp Val Gln Asp Phe Glu Glu Asn Gly Leu Ser Val Tyr Asn
225                 230                 235                 240
Tyr Asn Ala Tyr Ser Leu Tyr Phe Leu Pro Ala Thr Arg Phe Thr Gln
                245                 250                 255
Glu Asp Ile Thr Glu Gln Ile Asp Tyr Met Lys Trp Ala Tyr Ala Tyr
            260                 265                 270
Asn Lys Phe Phe Tyr Ile Ser Asp Tyr Tyr Lys Gln Val Asp Thr Ser
        275                 280                 285
Asn Val Lys Gly Ser Ser Leu Val Phe Trp Gly Glu His Ala Asn Asp
290                 295                 300
```

Leu Ser Gln Glu Gly Leu Leu Lys Gln Glu Lys Pro Leu Ile Gln Asn
305                 310                 315                 320

Phe Leu Gly Leu

<210> SEQ ID NO 19
<211> LENGTH: 324
<212> TYPE: PRT
<213> ORGANISM: Terribacillus saccharophilus

<400> SEQUENCE: 19

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Ala Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Tyr Ala Tyr
            260                 265                 270

Asn Lys Phe Phe Tyr Ile Ser Asp Tyr Tyr Lys Gln Val Asp Thr Pro
        275                 280                 285

Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 20
<211> LENGTH: 461
<212> TYPE: PRT

<213> ORGANISM: Curtobacterium oceanosedimentum

<400> SEQUENCE: 20

| | | | | | | | | | | | | | | |
|---|---|---|---|---|---|---|---|---|---|---|---|---|---|---|
| Ala | Asp | Arg | Asn | Thr | Ser | Ala | Ala | Glu | Ala | Ala | Val | Thr | Ser | Ile | Ala |
| 1 | | | | 5 | | | | | 10 | | | | | 15 | |
| Pro | Arg | Ala | Thr | Ile | Thr | Gly | Val | Ala | Ala | Ile | Ser | Ala | Ala | Thr | Ser |
| | | | 20 | | | | | 25 | | | | | 30 | | |
| Ser | Arg | Thr | Thr | Val | Arg | Thr | Thr | Leu | Thr | Leu | Glu | Asn | Arg | Ser | Gly |
| | | 35 | | | | | 40 | | | | | 45 | | | |
| Glu | Arg | Glu | Ser | Ala | Ala | Asp | Ala | Trp | Leu | Tyr | Leu | Ala | Gly | Gly | Gly |
| | 50 | | | | | 55 | | | | | 60 | | | | |
| Ala | Arg | Tyr | Ala | Leu | Gly | His | Ala | Pro | Val | Arg | Ala | Leu | Ala | Ala | Gly |
| 65 | | | | | 70 | | | | | 75 | | | | | 80 |
| Ala | Arg | Ala | Thr | Val | Arg | Thr | Thr | Leu | Arg | Val | Pro | Ser | Arg | Ala | Pro |
| | | | | 85 | | | | | 90 | | | | | 95 | |
| Ala | Gly | Lys | Tyr | Ala | Val | Leu | Ala | Cys | Ala | Gly | Pro | Tyr | Ser | Lys | Gln |
| | | | 100 | | | | | 105 | | | | | 110 | | |
| Ala | Cys | Arg | Thr | Ser | Gly | Thr | Thr | Val | Thr | Val | Gly | Thr | Ala | Ala | Arg |
| | | 115 | | | | | 120 | | | | | 125 | | | |
| Ala | Arg | Pro | Glu | Thr | Gly | Val | Met | Leu | Asp | Val | Ala | Arg | Ala | Tyr | Tyr |
| | 130 | | | | | 135 | | | | | 140 | | | | |
| Pro | Val | Ser | Leu | Ile | Glu | Gln | Tyr | Val | Asp | Leu | Leu | Ala | Glu | His | Gly |
| 145 | | | | | 150 | | | | | 155 | | | | | 160 |
| Gly | Gly | Phe | Leu | His | Leu | His | Leu | Thr | Asp | Asp | Gln | Asn | Val | Gly | Ile |
| | | | | 165 | | | | | 170 | | | | | 175 | |
| Glu | Ser | Ala | Val | Leu | Gly | Gln | Thr | Pro | Ala | Asn | Ala | Val | Leu | Arg | Asn |
| | | | 180 | | | | | 185 | | | | | 190 | | |
| Gly | Val | Tyr | Thr | Ser | Arg | Val | Thr | Gly | Arg | Pro | Phe | Leu | Ser | Ala | Ala |
| | | 195 | | | | | 200 | | | | | 205 | | | |
| Gln | Ala | Arg | Ala | Ile | Ser | Ala | Tyr | Ala | Ala | Lys | Arg | Gly | Ile | Ala | Ile |
| | 210 | | | | | 215 | | | | | 220 | | | | |
| Val | Pro | Glu | Val | Asp | Ser | Pro | Gly | His | Met | Ala | Ala | Phe | Ala | Leu |
| 225 | | | | | 230 | | | | | 235 | | | | | 240 |
| Leu | Glu | Ala | Arg | His | Gly | Ala | Thr | Trp | Val | Asp | Arg | Ile | Arg | Ser | Gly |
| | | | | 245 | | | | | 250 | | | | | 255 | |
| Glu | Ser | Glu | Leu | Asp | Thr | Ser | Val | Pro | Glu | Ser | Ala | Thr | Leu | Ala | Ala |
| | | | 260 | | | | | 265 | | | | | 270 | | |
| Glu | Leu | Leu | Arg | Glu | Val | Thr | Gln | Thr | Phe | Pro | Ser | Ser | Arg | Thr | Val |
| | | 275 | | | | | 280 | | | | | 285 | | | |
| His | Ile | Gly | Gly | Asp | Glu | Trp | Gly | Ala | Asp | Val | Ser | Ala | Asp | Glu | Arg |
| | 290 | | | | | 295 | | | | | 300 | | | | |
| Val | Gly | Trp | Met | Asn | Ala | Met | Ala | Ala | Ile | Gly | Asp | Arg | Glu | Val |
| 305 | | | | | 310 | | | | | 315 | | | | | 320 |
| Trp | Ala | Trp | Asn | Asp | Gly | Ile | Asp | Arg | Ala | Ser | Val | Gly | Arg | Leu | Asp |
| | | | | 325 | | | | | 330 | | | | | 335 | |
| Pro | Arg | Ile | His | Val | Thr | Tyr | Trp | Ser | Phe | Asp | Gly | Asp | Thr | Glu | Asp |
| | | | 340 | | | | | 345 | | | | | 350 | | |
| Ala | Ala | Glu | Arg | Arg | Glu | Arg | Arg | Ala | Arg | Arg | Ala | Ser | Ala | Thr | Asp |
| | | 355 | | | | | 360 | | | | | 365 | | | |
| Leu | Gln | Arg | Ala | Gly | Ile | Asp | Leu | Leu | Asn | Tyr | Asn | Ser | Tyr | Tyr | Leu |
| | 370 | | | | | 375 | | | | | 380 | | | | |
| Tyr | Glu | Val | Pro | Thr | Asp | Leu | Asp | Pro | Ala | Asp | Ser | Glu | Tyr | Thr | Val |
| 385 | | | | | 390 | | | | | 395 | | | | | 400 |

```
Ala Asp Leu Arg Glu His Trp Ser Leu Arg Ala Trp Asp Gly Asp Ser
            405                 410                 415

Gly Ala Arg Leu Ala Ala Pro Met Ser Gly Ala Ala Val Ala Ile Trp
        420                 425                 430

Gly Glu Asp Leu Asp Gly Ala Pro Ser Glu Ala Leu Leu Arg Trp Ser
    435                 440                 445

Ala Pro His Val Thr Ala Met Ile Glu Thr Ala Ala Ser
450                 455                 460

<210> SEQ ID NO 21
<211> LENGTH: 9
<212> TYPE: PRT
<213> ORGANISM: Artificial
<220> FEATURE:
<223> OTHER INFORMATION: Polypeptide motif I in some hexosaminidases of
      the invention
<220> FEATURE:
<221> NAME/KEY: misc_feature
<222> LOCATION: (1)..(1)
<223> OTHER INFORMATION: Xaa = I (Ile) or V (Val)
<220> FEATURE:
<221> NAME/KEY: misc_feature
<222> LOCATION: (3)..(3)
<223> OTHER INFORMATION: Xaa = E (Glu) or D (Asp)
<220> FEATURE:
<221> NAME/KEY: misc_feature
<222> LOCATION: (4)..(4)
<223> OTHER INFORMATION: Xaa = L (Leu) or V (Val) or I (Ile)
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa = A (Ala) or N (Asn)

<400> SEQUENCE: 21

Xaa Pro Xaa Xaa Asp Xaa Pro Xaa His
1               5

<210> SEQ ID NO 22
<211> LENGTH: 8
<212> TYPE: PRT
<213> ORGANISM: Artificial
<220> FEATURE:
<223> OTHER INFORMATION: Polypeptide motif II in some hexosaminidases of
      the invention
<220> FEATURE:
<221> NAME/KEY: MISC_FEATURE
<222> LOCATION: (4)..(4)
<223> OTHER INFORMATION: Xaa = A(Ala) or S (Ser)
<220> FEATURE:
<221> NAME/KEY: MISC_FEATURE
<222> LOCATION: (6)..(6)
<223> OTHER INFORMATION: Xaa = S (Ser) or Y (Tyr)

<400> SEQUENCE: 22

Asn Tyr Asn Xaa Tyr Xaa Leu Tyr
1               5

<210> SEQ ID NO 23
<211> LENGTH: 27
<212> TYPE: PRT
<213> ORGANISM: Bacillus clausii

<400> SEQUENCE: 23

Met Lys Lys Pro Leu Gly Lys Ile Val Ala Ser Thr Ala Leu Leu Ile
1               5                   10                  15
```

```
Ser Val Ala Phe Ser Ser Ile Ala Ser Ala
            20              25

<210> SEQ ID NO 24
<211> LENGTH: 8
<212> TYPE: PRT
<213> ORGANISM: Artificial
<220> FEATURE:
<223> OTHER INFORMATION: His-Tag

<400> SEQUENCE: 24

His His His His His His Pro Arg
1               5

<210> SEQ ID NO 25
<211> LENGTH: 486
<212> TYPE: PRT
<213> ORGANISM: Curtobacterium flaccumfaciens

<400> SEQUENCE: 25

Met Val Arg Gln Gln Gly Asn Val Gly Pro Gly Ser Ser Ala Arg Arg
1               5                   10                  15

Thr Leu Ala Val Gly Leu Ala Ile Ala Leu Ser Ala Ala Ala Leu Val
            20                  25                  30

Gly Ile Arg Ala Thr Ala Gly Ser Ala Asp Thr Ala Val Ser Ala Val
        35                  40                  45

Thr Val Thr Lys Val Thr Ala Ser Thr Thr Gly Thr Val Val Arg Thr
50                  55                  60

Thr Leu Lys Val Glu Asn Thr Ala Pro Val Arg Lys Pro Ala Ser Ser
65                  70                  75                  80

Val Trp Leu Tyr Leu Ser Ala Gly Thr Glu Lys Tyr Thr Leu Gly Arg
                85                  90                  95

Val Ala Val Lys Ala Leu Ala Ala Gly Ser Ser Thr Ser Val Thr Ala
            100                 105                 110

Val Arg Gly Thr Pro Ser Arg Ala Ala Ala Gly Lys Tyr Ser Val Leu
        115                 120                 125

Ala Cys Ala Gly Ala Tyr Ser Ala Lys Gln Cys Arg Thr Ser Thr Ala
130                 135                 140

Thr Val Thr Thr Lys Pro Thr Lys Arg Ala Arg Pro Glu Thr Gly Val
145                 150                 155                 160

Met Leu Asp Val Ala Arg Ala Tyr Tyr Pro Val Ala Leu Ile Lys Arg
                165                 170                 175

Tyr Ile Asp Leu Leu Ala Asp Asp Gly Gly Arg Phe Leu His Leu His
            180                 185                 190

Leu Thr Asp Asp Gln Asn Val Gly Ile Glu Ser Thr Val Leu Gly Gln
        195                 200                 205

Thr Pro Ala Asn Ala Asp Leu Asp His Gly Val Tyr Thr Ser Arg Val
210                 215                 220

Thr His Arg Pro Phe Leu Ser Ala Ala Gln Ala Arg Thr Ile Ser Ala
225                 230                 235                 240

Tyr Gly Ala Glu Arg Gly Val Ala Ile Val Pro Glu Ile Asp Thr Pro
                245                 250                 255

Gly His Met Ala Ala Phe Ala Leu Leu Glu Ala Gln His Gly Thr
            260                 265                 270

Lys Trp Val Asp Arg Ile Arg Ser Gly Glu Asn Glu Leu Asp Thr Ser
        275                 280                 285

Ala Pro Glu Ser Leu Ala Leu Ala Lys Lys Leu Tyr Ala Glu Val Gln
```

```
                    290                 295                 300
Arg Thr Phe Pro Ser Ser Arg Thr Val His Ile Gly Gly Asp Glu Trp
305                 310                 315                 320

Gly Asp Asp Val Thr Ala Ala Gln Arg Val Thr Trp Met Asn Ala Met
                325                 330                 335

Ala Ala Ala Leu Asp Asp Arg Glu Val Trp Ala Trp Asn Asp Gly Ile
            340                 345                 350

Asp Arg Val Ala Val Gly Arg Leu Asp Pro Arg Ile His Val Thr Tyr
        355                 360                 365

Trp Ser Phe Asp Gly Asp Thr Glu Asp Ala Ala Glu Arg Arg Glu Arg
    370                 375                 380

Arg Ala Arg Ala Ser Ala Val Asp Leu Gln Gln Ala Gly Ile Asp
385                 390                 395                 400

Gln Leu Asn Tyr Asn Ser Tyr Tyr Leu Tyr Glu Val Pro Thr Asp Leu
                405                 410                 415

Asp Pro Ala Asp Ser Asp Tyr Thr Val Ala Asp Leu Arg Glu Asn Trp
            420                 425                 430

Ser Leu Arg Ala Trp Asp Gly Asp Ser Gly Leu Leu Ala Ala Pro
        435                 440                 445

Met Ser Gly Ala Ala Val Ala Ile Trp Gly Glu Asp Leu Glu Asp Pro
    450                 455                 460

Pro Ser Asp Ala Leu Leu Arg Trp Ser Ala Pro His Val Thr Ala Met
465                 470                 475                 480

Ile Glu Thr Ala Ala Ser
                485

<210> SEQ ID NO 26
<211> LENGTH: 486
<212> TYPE: PRT
<213> ORGANISM: Curtobacterium luteum

<400> SEQUENCE: 26

Met Val Arg Gln Gln Gly Asn Val Gly Pro Gly Ser Ser Ala Arg Arg
1               5                   10                  15

Thr Leu Ala Val Gly Leu Ala Ile Ala Leu Ser Ala Ala Ala Leu Val
            20                  25                  30

Gly Ile Arg Ala Thr Ala Gly Ser Ala Asp Thr Ala Val Ser Ala Val
        35                  40                  45

Thr Val Thr Lys Val Thr Ala Ser Thr Thr Gly Thr Ala Val Arg Thr
    50                  55                  60

Thr Leu Lys Val Glu Asn Thr Ala Pro Val Arg Lys Pro Ala Ser Ser
65                  70                  75                  80

Val Trp Leu Tyr Leu Ser Ala Gly Thr Glu Lys Tyr Thr Leu Gly Arg
                85                  90                  95

Val Ala Val Lys Ala Leu Ser Ala Gly Ser Ser Thr Ser Val Thr Ala
            100                 105                 110

Val Arg Gly Thr Pro Ser Arg Ala Ala Ala Gly Lys Tyr Trp Val Leu
        115                 120                 125

Ala Cys Ala Gly Ala Tyr Ser Ala Lys Gln Cys Arg Thr Ser Thr Ala
    130                 135                 140

Thr Val Thr Thr Lys Pro Thr Lys Arg Ala Arg Pro Glu Thr Gly Val
145                 150                 155                 160

Met Leu Asp Val Ala Arg Ala Tyr Tyr Pro Val Ala Leu Ile Lys Arg
                165                 170                 175
```

```
Tyr Ile Asp Leu Leu Ala Asp Asp Gly Gly Arg Phe Leu His Leu His
            180                 185                 190

Leu Thr Asp Asp Gln Asn Val Gly Ile Glu Ser Thr Val Leu Gly Gln
        195                 200                 205

Thr Pro Ala Asn Ala Asp Leu Asp His Gly Val Tyr Thr Ser Arg Val
    210                 215                 220

Thr His Arg Pro Phe Leu Ser Ala Ala Gln Ala Arg Thr Ile Ser Glu
225                 230                 235                 240

Tyr Gly Ala Glu Arg Gly Val Thr Ile Val Pro Glu Ile Asp Thr Pro
                245                 250                 255

Gly His Met Ala Ala Ala Phe Ala Leu Leu Glu Ala Gln His Gly Thr
            260                 265                 270

Lys Trp Val Asp Arg Ile Arg Ser Gly Glu Asn Glu Leu Asp Thr Ser
        275                 280                 285

Ala Pro Glu Ser Leu Val Leu Ala Lys Lys Leu Tyr Ala Glu Val Gln
    290                 295                 300

Arg Thr Phe Pro Ser Ser Arg Thr Val His Ile Gly Gly Asp Glu Trp
305                 310                 315                 320

Gly Asp Asp Val Thr Ala Ala His Arg Val Ala Trp Met Asn Glu Met
                325                 330                 335

Ala Ala Thr Leu Gly Asn Arg Glu Val Trp Ala Trp Asn Asp Gly Ile
            340                 345                 350

Asp Arg Val Ala Val Gly Arg Leu Asp Pro Arg Ile His Val Thr Tyr
        355                 360                 365

Trp Ser Phe Asp Gly Asp Thr Glu Asp Ala Ala Glu Arg Arg Glu Arg
    370                 375                 380

Arg Ala Arg Arg Ala Ser Ala Val Asp Leu Gln Gln Ala Gly Ile Asp
385                 390                 395                 400

Gln Leu Asn Tyr Asn Ser Tyr Tyr Leu Tyr Glu Val Pro Thr Asp Leu
                405                 410                 415

Asp Pro Ala Asp Ser Asp Tyr Thr Val Ala Asp Leu Arg Glu Asn Trp
            420                 425                 430

Ser Leu Arg Ala Trp Asp Gly Asp Ser Gly Ser Leu Leu Ala Ala Pro
        435                 440                 445

Met Ser Gly Ala Ala Val Ala Ile Trp Gly Glu Asp Leu Glu Asp Pro
    450                 455                 460

Pro Ser Asp Ala Leu Leu Arg Trp Ser Ala Pro His Val Thr Ala Met
465                 470                 475                 480

Ile Glu Thr Ala Ala Ser
                485

<210> SEQ ID NO 27
<211> LENGTH: 481
<212> TYPE: PRT
<213> ORGANISM: Curtobacterium oceanosedimentum

<400> SEQUENCE: 27

Met Lys Arg Ser Ile Ala Val Gly Leu Val Ile Ala Met Ser Ala Ala
1               5                   10                  15

Val Val Ile Gly Ala Asp Ala Ile Gly Gly Ser Ala Gly Thr Ala Asp
            20                  25                  30

Ala Ser Gly Ala Pro Arg Leu Val Val Thr Lys Val Thr Ala Ser Ser
        35                  40                  45

Thr Thr Thr Ser Thr Arg Thr Val Arg Thr Thr Leu Thr Val Lys
    50                  55                  60
```

```
Asn Thr Ser Val Ala Arg Lys Pro Ala Asp Ala Trp Leu Ser Leu
 65                  70                  75                  80

Thr Ala Gly Ser Lys Arg Tyr Thr Leu Gly His Val Ser Val Gln Ser
             85                  90                  95

Leu Ala Ala Gly Ala Ser Ala Thr Ile His Ala Thr His Thr Ala Pro
            100                 105                 110

Pro Arg Ala Pro Ala Gly Lys Tyr Ala Val Leu Ala Cys Thr Gly Ala
            115                 120                 125

Phe Ser Leu Ser Lys Cys Gly Thr Ser Ala Thr Thr Val Thr Thr Ala
            130                 135                 140

Arg Ala Thr Arg Ala Arg Pro Asp Thr Gly Val Met Leu Asp Val Ala
145                 150                 155                 160

Arg Ala Tyr Tyr Pro Val Ala Leu Ile Glu Gln Tyr Ile Ala Leu Leu
                165                 170                 175

Ala Asp His Gly Gly Arg Phe Leu His Leu His Leu Thr Asp Asp Gln
            180                 185                 190

Asn Val Gly Ile Glu Ser Glu Val Leu Gly Gln Thr Leu Ala Asn Ala
            195                 200                 205

Asp Leu Arg Asp Gly Val Tyr Thr Ser Arg Ile Thr Gly Arg Pro Phe
210                 215                 220

Leu Ser Ala Ala Gln Ala Arg Glu Ile Ser Arg Tyr Ala Ala Gln Arg
225                 230                 235                 240

Gly Ile Ala Ile Ile Pro Glu Ile Asp Thr Pro Gly His Met Ala Ala
                245                 250                 255

Ala Phe Ala Leu Leu Glu Ala Gly His Gly Lys Gln Trp Val Asp Arg
            260                 265                 270

Ile Arg Ser Gly Glu Ser Glu Leu Asp Thr Ser Ala Pro Gly Ser Ser
            275                 280                 285

Ala Leu Ala Ala Arg Leu Leu Gln Glu Val Thr Arg Thr Phe Pro Ser
290                 295                 300

Ser Arg Thr Val His Ile Gly Gly Asp Glu Trp Gly Asp Asp Val Thr
305                 310                 315                 320

Ala Asp Glu Arg Val Gln Trp Leu Asn Thr Met Ala Ala Ala Val Gly
                325                 330                 335

Asn Arg Ala Val Trp Ala Trp Asn Asp Gly Ile Asp Arg Ala Ala Ile
            340                 345                 350

Gly Arg Leu Asp Pro Arg Ile His Val Thr Tyr Trp Ser Phe Asp Gly
            355                 360                 365

Asp Thr Glu Asp Ala Thr Glu Arg Arg Glu Arg Glu Arg Arg Ala
370                 375                 380

Gly Ala Asn Asp Leu Tyr Ala Ala Gly Ile Asp Leu Leu Asn Tyr Asn
385                 390                 395                 400

Ser Tyr Tyr Leu Tyr Glu Val Pro Thr Asp Leu Asp Ala Ala Asp Ser
                405                 410                 415

Glu Tyr Thr Val Ala Asp Leu Arg Glu Asn Trp Ser Leu Arg Thr Trp
            420                 425                 430

Asp Gly Asp Ser Gly Ala Arg Leu Ala Gly Pro Thr Ser Gly Ala Ala
            435                 440                 445

Val Ala Ile Trp Gly Glu Asp Leu Glu Ala Pro Pro Ser Asp Ala Leu
            450                 455                 460

Leu Arg Trp Ser Ala Pro His Val Leu Ala Met Ile Glu Thr Ala Gly
465                 470                 475                 480
```

Ser

<210> SEQ ID NO 28
<211> LENGTH: 475
<212> TYPE: PRT
<213> ORGANISM: Curtobacterium sp.

<400> SEQUENCE: 28

```
Met Val Ala Ala Gly Leu Ala Ile Ala Val Ser Ala Ala Ala Leu Ile
1               5                   10                  15

Gly Ile Asp Val Ile Ala Gly Ser Ala Ala Gly Ser Thr Thr Ser Thr
            20                  25                  30

Val Thr Val Thr Gln Val Thr Ala Thr Thr Ala Ser Ser Thr Gly
        35                  40                  45

Thr Ala Val Arg Thr Thr Leu Lys Ile Lys Asn Thr Ala Ala Val Arg
    50                  55                  60

Lys Pro Ala Ser Ser Ala Trp Leu Tyr Leu Ser Ala Gly Thr Lys Lys
65                  70                  75                  80

Tyr Thr Leu Gly Arg Val Ala Val Lys Ala Leu Ala Ala Gly Ser Ser
                85                  90                  95

Thr Ser Val Thr Ala Val Arg Gly Thr Pro Ser Arg Ala Thr Ala Gly
            100                 105                 110

Glu Tyr Ser Val Leu Ala Cys Ala Gly Ala Tyr Ser Ala Lys Gln Cys
        115                 120                 125

Arg Thr Ser Thr Ala Thr Val Thr Thr Lys Pro Thr Lys Arg Ala Arg
    130                 135                 140

Pro Glu Thr Gly Val Met Leu Asp Val Ala Arg Ala Tyr Tyr Pro Val
145                 150                 155                 160

Ala Leu Ile Lys Arg Tyr Ile Asp Leu Leu Ala Asp Asp Gly Gly Arg
                165                 170                 175

Phe Leu His Leu His Leu Thr Asp Asp Gln Asn Val Gly Ile Glu Ser
            180                 185                 190

Thr Val Leu Gly Gln Thr Leu Ala Asn Ala Asp Leu Asp Glu Gly Val
        195                 200                 205

Tyr Thr Ser Arg Val Thr Arg Arg Pro Phe Leu Ser Ala Ala Gln Ala
    210                 215                 220

Arg Thr Ile Ser Asp Tyr Ala Ala Arg Arg Gly Val Ala Ile Val Pro
225                 230                 235                 240

Glu Ile Asp Thr Pro Gly His Met Thr Ala Ala Phe Asp Leu Leu Glu
                245                 250                 255

Ala Gln His Gly Thr Lys Trp Val Asp Arg Ile Arg Ser Gly Glu Asn
            260                 265                 270

Glu Leu Asp Thr Ser Thr Pro Gly Ser Leu Ala Leu Ala Lys Lys Leu
        275                 280                 285

Tyr Ala Glu Val Gln Arg Thr Phe Pro Ala Ser Arg Thr Val His Ile
    290                 295                 300

Gly Gly Asp Glu Trp Gly Asp Asp Val Ser Ala Ala Glu Arg Val Ala
305                 310                 315                 320

Trp Met Asn Ala Met Ala Ala Ala Leu Gly Asn Arg Glu Val Trp Ala
                325                 330                 335

Trp Asn Asp Gly Ile Asp Arg Val Ala Val Gly Arg Leu Asp Pro Arg
            340                 345                 350

Ile His Val Thr Tyr Trp Ser Phe Asp Gly Asp Thr Glu Asp Ala Ala
        355                 360                 365
```

```
Glu Arg Arg Glu Arg Arg Ala Arg Arg Ala Ser Ala Val Asp Leu Gln
370                 375                 380

Gln Ala Gly Ile Asp Met Leu Asn Tyr Asn Ser Tyr Tyr Leu Tyr Glu
385                 390                 395                 400

Val Pro Thr Asp Leu Asp Pro Ala Asp Ser Glu Tyr Thr Val Ala Asp
                405                 410                 415

Leu Arg Glu Asn Trp Ser Leu Arg Thr Trp Asp Gly Asp Ser Gly Ser
                420                 425                 430

Leu Leu Ala Ala Pro Met Ser Gly Ala Ala Val Ala Ile Trp Gly Glu
                435                 440                 445

Asp Leu Glu Asp Pro Pro Ser Asp Ala Leu Leu Arg Trp Ser Ala Pro
450                 455                 460

His Val Thr Ala Met Ile Glu Thr Ala Ala Ser
465                 470                 475

<210> SEQ ID NO 29
<211> LENGTH: 1461
<212> TYPE: DNA
<213> ORGANISM: Curtobacterium flaccumfaciens

<400> SEQUENCE: 29
gtggtgcgtc agcaggggaa cgtgggtccc ggatcgtctg ccagacgcac gcttgcggtc     60
ggtctggcga tcgccctgtc ggccgcagct ctggtcggca tccgtgcaac ggcaggatca    120
gcggacaccg cagtctcggc ggtgacggtc acgaaggtca ccgcgtccac caccggcacc    180
gttgtgcgca ccaccctgaa ggtcgagaac accgccccgg tgcggaagcc ggcctcctcc    240
gtgtggctgt acctgtccgc cggcaccgag aagtacacgc tcggccgggt cgcggtgaag    300
gcactcgccg ctggttcgag cacctcggtc accgcagtcc gcgggacacc ttcccgtgcc    360
gcagccggca agtactcggt cctcgcctgc gccggtgcgt actccgcgaa gcagtgccgc    420
acgtcgacgg cgaccgtcac caccaagccc acgaagcgcg cgcgtccgga gacgggcgtg    480
atgctcgacg tcgctcgcgc ctactacccc gtggcgttga tcaagcggta catcgacctc    540
ctcgccgacg acggcgggcg cttcctgcac ctgcacctca ccgatgacca gaacgtcggg    600
atcgagagca cggtcctcgg ccagaccccc gcgaacgcgg atctcgacca cggcgtctac    660
accagccgcg tgacccatcg tccgttcctg agcgccgcgc aggcacgcac gatctccgcg    720
tacggggccg agcgaggcgt cgcgatcgtg ccggagatcg acaccccggg acacatggcc    780
gccgcgttcg ccctgctcga ggcgcagcac ggcacgaagt gggtcgaccg catccgttcg    840
ggcgagaacg agctcgacac gtcggcgccc gagagtctcg ccctggcgaa gaagctgtac    900
gcagaggtgc agcggacctt ccctccagc cgaaccgtgc acatcggcgg tgatgaatgg    960
ggcgacgacg tcaccgccgc ccaacgcgtc acctggatga cgcgatggc ggccgcgctc   1020 gacgaccgcg aggtgtgggc ctggaacgac gggatcgatc gggtcgcggt cgggcgactc   1080
gatccgcgca tccacgtcac gtactggagc ttcgacggcg acaccgagga cgcagcagaa   1140
cggcgcgaac gccgagcgcg gcgggcgagt gcggtcgacc tgcagcaggc cgggatcgac   1200
cagctcaact acaactcgta ctacctctac gaggtgccga ccgacctcga cccggccgac   1260
agcgattaca cggtcgccga tctccgcgag aactggtcgc tccgggcgtg ggacggcgac   1320
tccggttcgc ttctcgcggc tccgatgtcg ggcgccgccg tcgcgatctg ggtgaggac   1380 ctcgaagacc cgccatccga cgcgctcctg cggtggagcg caccgcacgt gacggcgatg   1440
atcgagaccg cagcctcctg a                                            1461
```

<210> SEQ ID NO 30
<211> LENGTH: 1461
<212> TYPE: DNA
<213> ORGANISM: Curtobacterium luteum

<400> SEQUENCE: 30

| | | | | | |
|---|---|---|---|---|---|
| gtggtgcgtc | agcaggggaa | cgtgggtccc | ggatcgtctg | ccagacgcac | gcttgcggtc | 60 |
| ggtctggcga | tcgccctgtc | ggccgcagct | ctggtcggca | tccgtgcaac | ggcaggatca | 120 |
| gcggacaccg | cagtctcggc | ggtgacggtc | acgaaggtca | ccgcgtccac | caccggcacc | 180 |
| gctgtgcgca | caaccctgaa | ggtcgagaac | accgccccgg | tgcggaagcc | ggcctcctcc | 240 |
| gtgtggctgt | acctgtccgc | cggcaccgag | aagtacacgc | tcggccgggt | cgcggtgaag | 300 |
| gcgctgtcgg | ctggttcgag | cacctcggtc | accgcagtcc | gcgggacacc | ttcccgtgcc | 360 |
| gcagccggca | agtactgggt | cctcgcctgc | gccggtgcgt | actccgcgaa | gcagtgccgc | 420 |
| acgtcgacgg | cgaccgtcac | caccaagccc | acgaagcgcg | cgcgtccgga | cgggcgtg   | 480 |
| atgctcgacg | tcgctcgcgc | ctactacccc | gtggcgttga | tcaagcggta | catcgacctc | 540 |
| ctcgccgacg | acggcgggcg | cttcctgcac | ctgcacctca | ccgatgacca | gaacgtcggg | 600 |
| atcgagagca | cggtcctcgg | ccagactccc | gcgaacgcgc | atctcgacca | cggcgtctac | 660 |
| accagccgcg | tgacccatcg | cccgttcctg | agtgccgcgc | aggcacgcac | gatctccgag | 720 |
| tacggggcgg | agcgaggcgt | cacgatcgtg | ccggagatcg | acactcccgg | acacatggcc | 780 |
| gccgcgttcg | ccctgctcga | ggcgcagcac | ggcacgaagt | gggtcgaccg | catccgttcg | 840 |
| ggcgagaacg | agctcgacac | gtcggcgccc | gagagtctcg | tgctggcgaa | gaagctgtac | 900 |
| gcagaggtgc | agcggaccct | cccttccagc | cgaaccgtgc | acatcggcgg | cgacgaatgg | 960 |
| ggcgacgacg | tcaccgccgc | acatcgcgtc | gcctggatga | acgagatggc | ggccacgctc | 1020 |
| ggcaaccgcg | aggtctgggc | ctggaacgac | gggatcgatc | gggttgcggt | cgggcgactc | 1080 |
| gatccgcgca | tccacgtcac | gtactggagc | ttcgacggcg | acaccgagga | cgcagcagaa | 1140 |
| cggcgcgaac | gccgagcgcg | gcgggcgagt | gcggtcgacc | tgcagcaggc | cgggatcgac | 1200 |
| cagctcaact | acaactcgta | ctacctctac | gaggtgccga | ccgacctcga | cccggccgac | 1260 |
| agcgattaca | cggtcgccga | tctccgcgag | aactggtcgc | tccgggcgtg | gacggcgac  | 1320 |
| tccggttcgc | ttctcgcggc | tccgatgtcg | ggcgccgccg | tcgcgatctg | gggtgaggac | 1380 |
| ctcgaagacc | cgccatccga | cgcgctcctg | cggtggagcg | caccgcacgt | gacggcgatg | 1440 |
| atcgagaccg | cagcctcctg | a | | | | 1461 |

<210> SEQ ID NO 31
<211> LENGTH: 1446
<212> TYPE: DNA
<213> ORGANISM: Curtobacterium oceanosedimentum

<400> SEQUENCE: 31

| | | | | | |
|---|---|---|---|---|---|
| gtgaagcgca | gcatcgccgt | cggcctggtg | atcgcgatgt | cggcggcagt | cgtgatcgga | 60 |
| gcggacgcga | tcggcggatc | ggcgggcact | gctgatgcgt | ccggagctcc | gcggctggtg | 120 |
| gtcaccaagg | tcaccgcgag | cagcaccacc | acgtcgacac | gcaccacggt | gcgcacgacg | 180 |
| ctgacggtca | agaacaccct | cggtggcgcg | aagccggcgg | ccgacgcatg | gctctcccctg | 240 |
| acggccggga | gcaagcggta | caccctcgga | cacgtctcgg | tgcagtcact | cgctgccggt | 300 |
| gcgagcgcga | cgatccacgc | gacgcacacc | gcgcctcctc | gtgcgccggc | cgggaagtac | 360 |
| gcggtcctcg | cgtgcacggg | agccttctcc | ctgtcgaagt | gcggcaccct | ggccacgacc | 420 |

```
gtcaccaccg cccgtgcgac ccgggcacgt cccgacaccg gcgtgatgct cgacgtggct      480
cgtgcctact acccggtggc gctgatcgag cagtacatcg cgctcctcgc tgatcacggt      540
ggtcgcttcc tgcacctcca cctcaccgac gaccagaacg tgggcatcga gagcgaggtc      600
ctcggccaga ccctcgcgaa cgccgatctc cgggacggtc tctacacgag tcggatcacc      660
ggtcggccgt tcctcagcgc ggcgcaggca cgggagatct cccggtacgc gcgcaacga       720 ggcatcgcga tcattcccga gatcgacacc cccggtcaca tggctgcggc gttcgctctc      780
ctcgaggccg acacggcaa gcagtgggtg accggatcc gttcgggcga gagcgaactc        840
gacacgtcgg cgcccggcag ctccgcgctg gcggcacgac tcctgcagga ggtcacgcgg      900
accttcccgt cgagccgcac cgtccacatc ggcggcgacg agtggggcga cgacgtcacc      960
gccgacgaac gcgtccagtg gttgaacacg atggcggccg ccgtcggcaa ccgtgcggtg     1020
tgggcgtgga acgacgggat cgaccgggct gcgatcgggc gactggatcc gcgtatccac     1080
gtcacctact ggagcttcga cggtgacacc gaggacgcga cggaacgccg cgagcgccgc     1140
gagcgacggg cgggtgcgaa cgacctgtac gcggccggga tcgacctgct gaactacaac     1200
tcgtactacc tgtacgaggt gccgacggac ctcgatgcgg ccgacagcga gtacaccgtc     1260
gccgatctcc gcgagaactg gtcgctccgg acctgggacg gggactcggg cgcacgtctg     1320
gcgggtccga cgtcggggc ggccgtcgcg atcggggcg aggacctcga agcgccaccg        1380
tccgacgcgc tcctgcgctg gagcgcccca cacgtgctcg cgatgatcga gaccgccggc     1440
tcgtag                                                               1446
```

<210> SEQ ID NO 32
<211> LENGTH: 1428
<212> TYPE: DNA
<213> ORGANISM: Curtobacterium sp.

<400> SEQUENCE: 32

```
atggtcgcag ccggtctggc gatcgcggtg tctgcggcag ccctgatcgg catcgatgtg       60
atcgccgggt cagctgccgg gtcgaccacc tcgacggtga cggtcaccca ggtcaccgcg      120
acgaccaccg ccagctccac cggcaccgcc gttcgcacca ccctcaagat caagaacact      180
gccgccgtgc ggaagccggc ttcctccgct tggctgtacc tgtccgccgg cacgaagaag      240
tacacactcg gccgggtcgc ggtgaaggca ctcgccgctg gttcgagcac gtccgtcacc      300
gcagtccgcg ggacgccctc ccgtgccacg gccggcgagt actcggtcct cgcctgcgcc      360
ggtgcgtact cggcgaagca gtgccgcacg tcgaccgcga ccgtcaccac caagccgacg      420
aagcgcgcgc gtccggagac gggcgtgatg ctcgacgtcg ctcgcgccta ctaccccgtg      480
gcgctgatca gcggtacat cgacctgctc gccgacgacg gtgggcgctt cctgcacctg       540
cacctcaccg atgaccagaa cgtcgggatc gagagcacgg tgctcggcca gaccctcgcc      600
aacgctgatc tcgacgaagg cgtgtacacg agcgtgtga cccgtcgtcc gttcctgagc       660
gccgcgcagg cacgcaccat ctccgactac gcagcgaggc ggggtgtcgc gatcgtgccc      720
gagatcgaca ctccgggcca catgactgcg gcattcgacc tgctcgaggc gcagcacggc      780
acgaagtggg tcgaccgcat ccgttcgggc gagaacgaac tcgacacgtc gacgcccggg      840
agcctcgcgc tggcgaagaa gctgtacgca gaggtgcagc ggaccttccc cgccagccga      900
accgtgcaca tcgcggtga tgagtgggc gacgacgtct cggccgccga acgggtcgcg         960
tggatgaacg cgatggcggc cgctctcggc aaccgcgagg tctgggcctg gaacgacggg     1020
```

```
atcgatcggg tcgcggtcgg gcgactggac ccgcgcatcc acgtcacgta ctggagcttc    1080
gacggcgaca ccgaggacgc agccgagcgg cgcgaacggc gagcgcgacg ggcgagtgcg    1140
gtcgacctgc agcaggccgg gatcgacatg ctcaactaca actcgtacta cctgtacgag    1200
gtaccgaccg acctcgaccc ggccgacagc gagtacaccg tcgccgatct ccgcgagaac    1260
tggtcactcc ggacgtggga cggcgactcc ggttcgctgc tcgcggctcc gatgtcgggc    1320
gccgccgtcg cgatctgggg tgaggacctc gaagacccgc catctgacgc gctcctgcgg    1380
tggagcgcac cgcacgtgac ggcgatgatc gagaccgcag cctcctga                1428
```

<210> SEQ ID NO 33
<211> LENGTH: 445
<212> TYPE: PRT
<213> ORGANISM: Curtobacterium flaccumfaciens

<400> SEQUENCE: 33

```
Asp Thr Ala Val Ser Ala Val Thr Val Thr Lys Val Thr Ala Ser Thr
1               5                   10                  15

Thr Gly Thr Val Val Arg Thr Thr Leu Lys Val Glu Asn Thr Ala Pro
            20                  25                  30

Val Arg Lys Pro Ala Ser Ser Val Trp Leu Tyr Leu Ser Ala Gly Thr
        35                  40                  45

Glu Lys Tyr Thr Leu Gly Arg Val Ala Val Lys Ala Leu Ala Ala Gly
    50                  55                  60

Ser Ser Thr Ser Val Thr Ala Val Arg Gly Thr Pro Ser Arg Ala Ala
65                  70                  75                  80

Ala Gly Lys Tyr Ser Val Leu Ala Cys Ala Gly Ala Tyr Ser Ala Lys
                85                  90                  95

Gln Cys Arg Thr Ser Thr Ala Thr Val Thr Thr Lys Pro Thr Lys Arg
            100                 105                 110

Ala Arg Pro Glu Thr Gly Val Met Leu Asp Val Ala Arg Ala Tyr Tyr
        115                 120                 125

Pro Val Ala Leu Ile Lys Arg Tyr Ile Asp Leu Leu Ala Asp Asp Gly
    130                 135                 140

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
            180                 185                 190

Gln Ala Arg Thr Ile Ser Ala Tyr Gly Ala Glu Arg Gly Val Ala Ile
        195                 200                 205

Val Pro Glu Ile Asp Thr Pro Gly His Met Ala Ala Ala Phe Ala Leu
    210                 215                 220

Leu Glu Ala Gln His Gly Thr Lys Trp Val Asp Arg Ile Arg Ser Gly
225                 230                 235                 240

Glu Asn Glu Leu Asp Thr Ser Ala Pro Glu Ser Leu Ala Leu Ala Lys
                245                 250                 255

Lys Leu Tyr Ala Glu Val Gln Arg Thr Phe Pro Ser Ser Arg Thr Val
            260                 265                 270

His Ile Gly Gly Asp Glu Trp Gly Asp Val Thr Ala Ala Gln Arg
        275                 280                 285

Val Thr Trp Met Asn Ala Met Ala Ala Ala Leu Asp Asp Arg Glu Val
    290                 295                 300
```

```
Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
            325                 330                 335

Ala Ala Glu Arg Arg Glu Arg Ala Arg Arg Ala Ser Ala Val Asp
            340                 345                 350

Leu Gln Gln Ala Gly Ile Asp Gln Leu Asn Tyr Asn Ser Tyr Tyr Leu
            355                 360                 365

Tyr Glu Val Pro Thr Asp Leu Asp Pro Ala Asp Ser Asp Tyr Thr Val
            370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Val Ala Ile Trp
                405                 410                 415

Gly Glu Asp Leu Glu Asp Pro Ser Asp Ala Leu Leu Arg Trp Ser
            420                 425                 430

Ala Pro His Val Thr Ala Met Ile Glu Thr Ala Ala Ser
            435                 440                 445

<210> SEQ ID NO 34
<211> LENGTH: 445
<212> TYPE: PRT
<213> ORGANISM: Curtobacterium luteum

<400> SEQUENCE: 34

Asp Thr Ala Val Ser Ala Val Thr Val Thr Lys Val Thr Ala Ser Thr
1               5                   10                  15

Thr Gly Thr Ala Val Arg Thr Thr Leu Lys Val Glu Asn Thr Ala Pro
                20                  25                  30

Val Arg Lys Pro Ala Ser Ser Val Trp Leu Tyr Leu Ser Ala Gly Thr
            35                  40                  45

Glu Lys Tyr Thr Leu Gly Arg Val Ala Val Lys Ala Leu Ser Ala Gly
        50                  55                  60

Ser Ser Thr Ser Val Thr Ala Val Arg Gly Thr Pro Ser Arg Ala Ala
65                  70                  75                  80

Ala Gly Lys Tyr Trp Val Leu Ala Cys Ala Gly Ala Tyr Ser Ala Lys
                85                  90                  95

Gln Cys Arg Thr Ser Thr Ala Thr Val Thr Thr Lys Pro Thr Lys Arg
            100                 105                 110

Ala Arg Pro Glu Thr Gly Val Met Leu Asp Val Ala Arg Ala Tyr Tyr
        115                 120                 125

Pro Val Ala Leu Ile Lys Arg Tyr Ile Asp Leu Leu Ala Asp Asp Gly
    130                 135                 140

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
            180                 185                 190

Gln Ala Arg Thr Ile Ser Glu Tyr Gly Ala Glu Arg Gly Val Thr Ile
        195                 200                 205

Val Pro Glu Ile Asp Thr Pro Gly His Met Ala Ala Ala Phe Ala Leu
    210                 215                 220

Leu Glu Ala Gln His Gly Thr Lys Trp Val Asp Arg Ile Arg Ser Gly
225                 230                 235                 240
```

```
Glu Asn Glu Leu Asp Thr Ser Ala Pro Glu Ser Leu Val Leu Ala Lys
                245                 250                 255

Lys Leu Tyr Ala Glu Val Gln Arg Thr Phe Pro Ser Ser Arg Thr Val
            260                 265                 270

His Ile Gly Gly Asp Glu Trp Gly Asp Val Thr Ala Ala His Arg
        275                 280                 285

Val Ala Trp Met Asn Glu Met Ala Ala Thr Leu Gly Asn Arg Glu Val
    290                 295                 300

Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
                325                 330                 335

Ala Ala Glu Arg Arg Glu Arg Arg Ala Arg Arg Ala Ser Ala Val Asp
            340                 345                 350

Leu Gln Gln Ala Gly Ile Asp Gln Leu Asn Tyr Asn Ser Tyr Tyr Leu
        355                 360                 365

Tyr Glu Val Pro Thr Asp Leu Asp Pro Ala Asp Ser Asp Tyr Thr Val
    370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Ala Val Ala Ile Trp
                405                 410                 415

Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
        435                 440                 445

<210> SEQ ID NO 35
<211> LENGTH: 458
<212> TYPE: PRT
<213> ORGANISM: Curtobacterium oceanosedimentum

<400> SEQUENCE: 35

Ile Gly Gly Ser Ala Gly Thr Ala Asp Ala Ser Gly Ala Pro Arg Leu
1               5                   10                  15

Val Val Thr Lys Val Thr Ala Ser Ser Thr Thr Ser Thr Arg Thr
            20                  25                  30

Thr Val Arg Thr Thr Leu Thr Val Lys Asn Thr Ser Val Ala Arg Lys
        35                  40                  45

Pro Ala Ala Asp Ala Trp Leu Ser Leu Thr Ala Gly Ser Lys Arg Tyr
    50                  55                  60

Thr Leu Gly His Val Ser Val Gln Ser Leu Ala Ala Gly Ala Ser Ala
65                  70                  75                  80

Thr Ile His Ala Thr His Thr Ala Pro Pro Arg Ala Pro Ala Gly Lys
                85                  90                  95

Tyr Ala Val Leu Ala Cys Thr Gly Ala Phe Ser Leu Ser Lys Cys Gly
            100                 105                 110

Thr Ser Ala Thr Thr Val Thr Thr Ala Arg Ala Thr Arg Ala Arg Pro
        115                 120                 125

Asp Thr Gly Val Met Leu Asp Val Ala Arg Ala Tyr Tyr Pro Val Ala
    130                 135                 140

Leu Ile Glu Gln Tyr Ile Ala Leu Leu Ala Asp His Gly Gly Arg Phe
145                 150                 155                 160

Leu His Leu His Leu Thr Asp Asp Gln Asn Val Gly Ile Glu Ser Glu
```

```
            165                 170                 175
Val Leu Gly Gln Thr Leu Ala Asn Ala Asp Leu Arg Asp Gly Val Tyr
            180                 185                 190

Thr Ser Arg Ile Thr Gly Arg Pro Phe Leu Ser Ala Gln Ala Arg
        195                 200                 205

Glu Ile Ser Arg Tyr Ala Ala Gln Arg Gly Ile Ala Ile Ile Pro Glu
        210                 215                 220

Ile Asp Thr Pro Gly His Met Ala Ala Phe Ala Leu Leu Glu Ala
225                 230                 235                 240

Gly His Gly Lys Gln Trp Val Asp Arg Ile Arg Ser Gly Ser Glu
                245                 250                 255

Leu Asp Thr Ser Ala Pro Gly Ser Ser Ala Leu Ala Ala Arg Leu Leu
                260                 265                 270

Gln Glu Val Thr Arg Thr Phe Pro Ser Ser Arg Thr Val His Ile Gly
                275                 280                 285

Gly Asp Glu Trp Gly Asp Asp Val Thr Ala Asp Glu Arg Val Gln Trp
                290                 295                 300

Leu Asn Thr Met Ala Ala Val Gly Asn Arg Ala Val Trp Ala Trp
305                 310                 315                 320

Asn Asp Gly Ile Asp Arg Ala Ala Ile Gly Arg Leu Asp Pro Arg Ile
                325                 330                 335

His Val Thr Tyr Trp Ser Phe Asp Gly Asp Thr Glu Asp Ala Thr Glu
                340                 345                 350

Arg Arg Glu Arg Arg Glu Arg Ala Gly Ala Asn Asp Leu Tyr Ala
                355                 360                 365

Ala Gly Ile Asp Leu Leu Asn Tyr Asn Ser Tyr Tyr Leu Tyr Glu Val
                370                 375                 380

Pro Thr Asp Leu Asp Ala Ala Asp Ser Glu Tyr Thr Val Ala Asp Leu
385                 390                 395                 400

Arg Glu Asn Trp Ser Leu Arg Thr Trp Asp Gly Asp Ser Gly Ala Arg
                405                 410                 415

Leu Ala Gly Pro Thr Ser Gly Ala Ala Val Ala Ile Trp Gly Glu Asp
                420                 425                 430

Leu Glu Ala Pro Pro Ser Asp Ala Leu Leu Arg Trp Ser Ala Pro His
                435                 440                 445

Val Leu Ala Met Ile Glu Thr Ala Gly Ser
                450                 455

<210> SEQ ID NO 36
<211> LENGTH: 450
<212> TYPE: PRT
<213> ORGANISM: Curtobacterium sp.

<400> SEQUENCE: 36

Ala Gly Ser Thr Thr Ser Thr Val Thr Val Thr Gln Val Thr Ala Thr
1               5                   10                  15

Thr Thr Ala Ser Ser Thr Gly Thr Ala Val Arg Thr Thr Leu Lys Ile
                20                  25                  30

Lys Asn Thr Ala Ala Val Arg Lys Pro Ala Ser Ser Ala Trp Leu Tyr
                35                  40                  45

Leu Ser Ala Gly Thr Lys Lys Tyr Thr Leu Gly Arg Val Ala Val Lys
            50                  55                  60

Ala Leu Ala Ala Gly Ser Ser Thr Ser Val Thr Ala Val Arg Gly Thr
65              70                  75                  80
```

Pro Ser Arg Ala Thr Ala Gly Glu Tyr Ser Val Leu Ala Cys Ala Gly
                85                  90                  95

Ala Tyr Ser Ala Lys Gln Cys Arg Thr Ser Thr Ala Thr Val Thr Thr
            100                 105                 110

Lys Pro Thr Lys Arg Ala Arg Pro Glu Thr Gly Val Met Leu Asp Val
        115                 120                 125

Ala Arg Ala Tyr Tyr Pro Val Ala Leu Ile Lys Arg Tyr Ile Asp Leu
    130                 135                 140

Leu Ala Asp Asp Gly Gly Arg Phe Leu His Leu His Leu Thr Asp Asp
145                 150                 155                 160

Gln Asn Val Gly Ile Glu Ser Thr Val Leu Gly Gln Thr Leu Ala Asn
                165                 170                 175

Ala Asp Leu Asp Glu Gly Val Tyr Thr Ser Arg Val Thr Arg Arg Pro
            180                 185                 190

Phe Leu Ser Ala Ala Gln Ala Arg Thr Ile Ser Asp Tyr Ala Ala Arg
        195                 200                 205

Arg Gly Val Ala Ile Val Pro Glu Ile Asp Thr Pro Gly His Met Thr
    210                 215                 220

Ala Ala Phe Asp Leu Leu Glu Ala Gln His Gly Thr Lys Trp Val Asp
225                 230                 235                 240

Arg Ile Arg Ser Gly Glu Asn Glu Leu Asp Thr Ser Thr Pro Gly Ser
                245                 250                 255

Leu Ala Leu Ala Lys Lys Leu Tyr Ala Glu Val Gln Arg Thr Phe Pro
            260                 265                 270

Ala Ser Arg Thr Val His Ile Gly Gly Asp Glu Trp Gly Asp Asp Val
        275                 280                 285

Ser Ala Ala Glu Arg Val Ala Trp Met Asn Ala Met Ala Ala Ala Leu
290                 295                 300

Gly Asn Arg Glu Val Trp Ala Trp Asn Asp Gly Ile Asp Arg Val Ala
305                 310                 315                 320

Val Gly Arg Leu Asp Pro Arg Ile His Val Thr Tyr Trp Ser Phe Asp
                325                 330                 335

Gly Asp Thr Glu Asp Ala Ala Glu Arg Arg Glu Arg Ala Arg Arg
            340                 345                 350

Ala Ser Ala Val Asp Leu Gln Gln Ala Gly Ile Asp Met Leu Asn Tyr
        355                 360                 365

Asn Ser Tyr Tyr Leu Tyr Glu Val Pro Thr Asp Leu Asp Pro Ala Asp
    370                 375                 380

Ser Glu Tyr Thr Val Ala Asp Leu Arg Glu Asn Trp Ser Leu Arg Thr
385                 390                 395                 400

Trp Asp Gly Asp Ser Gly Ser Leu Leu Ala Ala Pro Met Ser Gly Ala
                405                 410                 415

Ala Val Ala Ile Trp Gly Glu Asp Leu Glu Asp Pro Pro Ser Asp Ala
            420                 425                 430

Leu Leu Arg Trp Ser Ala Pro His Val Thr Ala Met Ile Glu Thr Ala
        435                 440                 445

Ala Ser
    450

<210> SEQ ID NO 37
<211> LENGTH: 306
<212> TYPE: PRT
<213> ORGANISM: Curtobacterium flaccumfaciens

<400> SEQUENCE: 37

Gly Val Met Leu Asp Val Ala Arg Ala Tyr Tyr Pro Val Ala Leu Ile
1               5                   10                  15

Lys Arg Tyr Ile Asp Leu Leu Ala Asp Asp Gly Arg Phe Leu His
            20                  25                  30

Leu His Leu Thr Asp Asp Gln Asn Val Gly Ile Glu Ser Thr Val Leu
        35                  40                  45

Gly Gln Thr Pro Ala Asn Ala Asp Leu Asp His Gly Val Tyr Thr Ser
    50                  55                  60

Arg Val Thr His Arg Pro Phe Leu Ser Ala Ala Gln Ala Arg Thr Ile
65                  70                  75                  80

Ser Ala Tyr Gly Ala Glu Arg Gly Val Ala Ile Val Pro Glu Ile Asp
                85                  90                  95

Thr Pro Gly His Met Ala Ala Ala Phe Ala Leu Leu Glu Ala Gln His
            100                 105                 110

Gly Thr Lys Trp Val Asp Arg Ile Arg Ser Gly Glu Asn Glu Leu Asp
        115                 120                 125

Thr Ser Ala Pro Glu Ser Leu Ala Leu Ala Lys Lys Leu Tyr Ala Glu
130                 135                 140

Val Gln Arg Thr Phe Pro Ser Ser Arg Thr Val His Ile Gly Gly Asp
145                 150                 155                 160

Glu Trp Gly Asp Asp Val Thr Ala Ala Gln Arg Val Thr Trp Met Asn
                165                 170                 175

Ala Met Ala Ala Ala Leu Asp Asp Arg Glu Val Trp Ala Trp Asn Asp
            180                 185                 190

Gly Ile Asp Arg Val Ala Val Gly Arg Leu Asp Pro Arg Ile His Val
        195                 200                 205

Thr Tyr Trp Ser Phe Asp Gly Asp Thr Glu Asp Ala Ala Glu Arg Arg
210                 215                 220

Glu Arg Arg Ala Arg Arg Ala Ser Ala Val Asp Leu Gln Gln Ala Gly
225                 230                 235                 240

Ile Asp Gln Leu Asn Tyr Asn Ser Tyr Tyr Leu Tyr Glu Val Pro Thr
                245                 250                 255

Asp Leu Asp Pro Ala Asp Ser Asp Tyr Thr Val Ala Asp Leu Arg Glu
            260                 265                 270

Asn Trp Ser Leu Arg Ala Trp Asp Gly Asp Ser Gly Ser Leu Leu Ala
        275                 280                 285

Ala Pro Met Ser Gly Ala Ala Val Ala Ile Trp Gly Glu Asp Leu Glu
    290                 295                 300

Asp Pro
305

<210> SEQ ID NO 38
<211> LENGTH: 306
<212> TYPE: PRT
<213> ORGANISM: Curtobacterium luteum

<400> SEQUENCE: 38

Gly Val Met Leu Asp Val Ala Arg Ala Tyr Tyr Pro Val Ala Leu Ile
1               5                   10                  15

Lys Arg Tyr Ile Asp Leu Leu Ala Asp Asp Gly Arg Phe Leu His
            20                  25                  30

Leu His Leu Thr Asp Asp Gln Asn Val Gly Ile Glu Ser Thr Val Leu
        35                  40                  45

Gly Gln Thr Pro Ala Asn Ala Asp Leu Asp His Gly Val Tyr Thr Ser

```
     50                  55                  60
Arg Val Thr His Arg Pro Phe Leu Ser Ala Ala Gln Ala Arg Thr Ile
 65                  70                  75                  80

Ser Glu Tyr Gly Ala Glu Arg Gly Val Thr Ile Val Pro Glu Ile Asp
                 85                  90                  95

Thr Pro Gly His Met Ala Ala Ala Phe Ala Leu Leu Glu Ala Gln His
                100                 105                 110

Gly Thr Lys Trp Val Asp Arg Ile Arg Ser Gly Glu Asn Glu Leu Asp
                115                 120                 125

Thr Ser Ala Pro Glu Ser Leu Val Leu Ala Lys Lys Leu Tyr Ala Glu
            130                 135                 140

Val Gln Arg Thr Phe Pro Ser Ser Arg Thr Val His Ile Gly Gly Asp
145                 150                 155                 160

Glu Trp Gly Asp Asp Val Thr Ala Ala His Arg Val Ala Trp Met Asn
                165                 170                 175

Glu Met Ala Ala Thr Leu Gly Asn Arg Glu Val Trp Ala Trp Asn Asp
                180                 185                 190

Gly Ile Asp Arg Val Ala Val Gly Arg Leu Asp Pro Arg Ile His Val
                195                 200                 205

Thr Tyr Trp Ser Phe Asp Gly Asp Thr Glu Asp Ala Ala Glu Arg Arg
            210                 215                 220

Glu Arg Arg Ala Arg Arg Ala Ser Ala Val Asp Leu Gln Gln Ala Gly
225                 230                 235                 240

Ile Asp Gln Leu Asn Tyr Asn Ser Tyr Tyr Leu Tyr Glu Val Pro Thr
                245                 250                 255

Asp Leu Asp Pro Ala Asp Ser Asp Tyr Thr Val Ala Asp Leu Arg Glu
                260                 265                 270

Asn Trp Ser Leu Arg Ala Trp Asp Gly Asp Ser Gly Ser Leu Leu Ala
            275                 280                 285

Ala Pro Met Ser Gly Ala Ala Val Ala Ile Trp Gly Glu Asp Leu Glu
            290                 295                 300

Asp Pro
305

<210> SEQ ID NO 39
<211> LENGTH: 304
<212> TYPE: PRT
<213> ORGANISM: Curtobacterium oceanosedimentum

<400> SEQUENCE: 39

Gly Val Met Leu Asp Val Ala Arg Ala Tyr Tyr Pro Val Ala Leu Ile
 1               5                  10                  15

Glu Gln Tyr Ile Ala Leu Leu Ala Asp His Gly Gly Arg Phe Leu His
                20                  25                  30

Leu His Leu Thr Asp Asp Gln Asn Val Gly Ile Glu Ser Glu Val Leu
            35                  40                  45

Gly Gln Thr Leu Ala Asn Ala Asp Leu Arg Asp Gly Val Tyr Thr Ser
        50                  55                  60

Arg Ile Thr Gly Arg Pro Phe Leu Ser Ala Ala Gln Ala Arg Glu Ile
 65                  70                  75                  80

Ser Arg Tyr Ala Ala Gln Arg Gly Ile Ala Ile Pro Glu Ile Asp
                85                  90                  95

Thr Pro Gly His Met Ala Ala Ala Phe Ala Leu Leu Glu Ala Gly His
                100                 105                 110
```

```
Gly Lys Gln Trp Val Asp Arg Ile Arg Ser Gly Glu Ser Glu Leu Asp
            115                 120                 125

Thr Ser Ala Pro Gly Ser Ser Ala Leu Ala Ala Arg Leu Leu Gln Glu
130                 135                 140

Val Thr Arg Thr Phe Pro Ser Ser Arg Thr Val His Ile Gly Gly Asp
145                 150                 155                 160

Glu Trp Gly Asp Asp Val Thr Ala Asp Glu Arg Val Gln Trp Leu Asn
                165                 170                 175

Thr Met Ala Ala Ala Val Gly Asn Arg Ala Val Trp Ala Trp Asn Asp
            180                 185                 190

Gly Ile Asp Arg Ala Ala Ile Gly Arg Leu Asp Pro Arg Ile His Val
        195                 200                 205

Thr Tyr Trp Ser Phe Asp Gly Asp Thr Glu Asp Ala Thr Glu Arg Arg
    210                 215                 220

Glu Arg Arg Glu Arg Arg Ala Gly Ala Asn Asp Leu Tyr Ala Ala Gly
225                 230                 235                 240

Ile Asp Leu Leu Asn Tyr Asn Ser Tyr Leu Tyr Glu Val Pro Thr
                245                 250                 255

Asp Leu Asp Ala Ala Asp Ser Glu Tyr Thr Val Ala Asp Leu Arg Glu
            260                 265                 270

Asn Trp Ser Leu Arg Thr Trp Asp Gly Asp Ser Gly Ala Arg Leu Ala
        275                 280                 285

Gly Pro Thr Ser Gly Ala Ala Val Ala Ile Trp Gly Glu Asp Leu Glu
    290                 295                 300

<210> SEQ ID NO 40
<211> LENGTH: 306
<212> TYPE: PRT
<213> ORGANISM: Curtobacterium sp.

<400> SEQUENCE: 40

Gly Val Met Leu Asp Val Ala Arg Ala Tyr Tyr Pro Val Ala Leu Ile
1               5                   10                  15

Lys Arg Tyr Ile Asp Leu Leu Ala Asp Asp Gly Gly Arg Phe Leu His
                20                  25                  30

Leu His Leu Thr Asp Asp Gln Asn Val Gly Ile Glu Ser Thr Val Leu
            35                  40                  45

Gly Gln Thr Leu Ala Asn Ala Asp Leu Asp Glu Gly Val Tyr Thr Ser
        50                  55                  60

Arg Val Thr Arg Arg Pro Phe Leu Ser Ala Ala Gln Ala Arg Thr Ile
65                  70                  75                  80

Ser Asp Tyr Ala Ala Arg Arg Gly Val Ala Ile Val Pro Glu Ile Asp
                85                  90                  95

Thr Pro Gly His Met Thr Ala Ala Phe Asp Leu Leu Glu Ala Gln His
            100                 105                 110

Gly Thr Lys Trp Val Asp Arg Ile Arg Ser Gly Glu Asn Glu Leu Asp
        115                 120                 125

Thr Ser Thr Pro Gly Ser Leu Ala Leu Ala Lys Lys Leu Tyr Ala Glu
    130                 135                 140

Val Gln Arg Thr Phe Pro Ala Ser Arg Thr Val His Ile Gly Gly Asp
145                 150                 155                 160

Glu Trp Gly Asp Asp Val Ser Ala Ala Glu Arg Val Ala Trp Met Asn
                165                 170                 175

Ala Met Ala Ala Ala Leu Gly Asn Arg Glu Val Trp Ala Trp Asn Asp
            180                 185                 190
```

```
Gly Ile Asp Arg Val Ala Val Gly Arg Leu Asp Pro Arg Ile His Val
        195                 200                 205

Thr Tyr Trp Ser Phe Asp Gly Asp Thr Glu Asp Ala Ala Glu Arg Arg
    210                 215                 220

Glu Arg Arg Ala Arg Arg Ala Ser Ala Val Asp Leu Gln Gln Ala Gly
225                 230                 235                 240

Ile Asp Met Leu Asn Tyr Asn Ser Tyr Tyr Leu Tyr Glu Val Pro Thr
                245                 250                 255

Asp Leu Asp Pro Ala Asp Ser Glu Tyr Thr Val Ala Asp Leu Arg Glu
                260                 265                 270

Asn Trp Ser Leu Arg Thr Trp Asp Gly Asp Ser Gly Ser Leu Leu Ala
                275                 280                 285

Ala Pro Met Ser Gly Ala Ala Val Ala Ile Trp Gly Glu Asp Leu Glu
            290                 295                 300

Asp Pro
305

<210> SEQ ID NO 41
<211> LENGTH: 4
<212> TYPE: PRT
<213> ORGANISM: Artificial
<220> FEATURE:
<223> OTHER INFORMATION: Polypeptide motif III in some hexosaminidases
      of the invention
<220> FEATURE:
<221> NAME/KEY: MISC_FEATURE
<222> LOCATION: (2)..(2)
<223> OTHER INFORMATION: Xaa = Any natural amino acid

<400> SEQUENCE: 41

Gly Xaa Asp Glu
1

<210> SEQ ID NO 42
<211> LENGTH: 7
<212> TYPE: PRT
<213> ORGANISM: Artificial
<220> FEATURE:
<223> OTHER INFORMATION: Polypeptide motif in some hexosaminidases of
      the invention

<400> SEQUENCE: 42

Ala Arg Ala Tyr Tyr Pro Val
1               5

<210> SEQ ID NO 43
<211> LENGTH: 7
<212> TYPE: PRT
<213> ORGANISM: Artificial
<220> FEATURE:
<223> OTHER INFORMATION: Polypeptide motif in some hexosaminidases of
      the invention

<400> SEQUENCE: 43

Ala Trp Asn Asp Gly Ile Asp
1               5

<210> SEQ ID NO 44
<211> LENGTH: 7
<212> TYPE: PRT
<213> ORGANISM: Artificial
<220> FEATURE:
<223> OTHER INFORMATION: Polypeptide motif in some hexosaminidases of
      the invention
```

```
<400> SEQUENCE: 44

Asp Asp Gln Asn Val Gly Ile
1               5

<210> SEQ ID NO 45
<211> LENGTH: 5
<212> TYPE: PRT
<213> ORGANISM: Artificial
<220> FEATURE:
<223> OTHER INFORMATION: Polypeptide motif in some hexosaminidases of
      the invention

<400> SEQUENCE: 45

Asp Pro Arg Ile His
1               5

<210> SEQ ID NO 46
<211> LENGTH: 7
<212> TYPE: PRT
<213> ORGANISM: Artificial
<220> FEATURE:
<223> OTHER INFORMATION: Polypeptide motif in some hexosaminidases of
      the invention
<220> FEATURE:
<221> NAME/KEY: MISC_FEATURE
<222> LOCATION: (1)..(1)
<223> OTHER INFORMATION: Xaa = (Glu) E or (Gln) Q
<220> FEATURE:
<221> NAME/KEY: MISC_FEATURE
<222> LOCATION: (2)..(2)
<223> OTHER INFORMATION: Xaa = (Asn) N or (Arg) R or (Ser) S or His (H)
      or Ala (A)
<220> FEATURE:
<221> NAME/KEY: MISC_FEATURE
<222> LOCATION: (3)..(3)
<223> OTHER INFORMATION: Xaa = (Tyr) Y or (Val) V or (Phe) F or (leu) L
<220> FEATURE:
<221> NAME/KEY: MISC_FEATURE
<222> LOCATION: (4)..(4)
<223> OTHER INFORMATION: Xaa = (Ala) A or (Gly) G or (Ser) S or (Thr) T
      or (Cys) C
<220> FEATURE:
<221> NAME/KEY: MISC_FEATURE
<222> LOCATION: (5)..(5)
<223> OTHER INFORMATION: Xaa = (Ile) I or (Val) V or (Leu) L or (Phe) F
<220> FEATURE:
<221> NAME/KEY: MISC_FEATURE
<222> LOCATION: (6)..(6)
<223> OTHER INFORMATION: Xaa = (Glu) E or (Ala) A or (Gln) Q or (Tyr) Y
      or (Asn) N
<220> FEATURE:
<221> NAME/KEY: MISC_FEATURE
<222> LOCATION: (7)..(7)
<223> OTHER INFORMATION: Xaa = (Ser) S or (Asn) N

<400> SEQUENCE: 46

Xaa Xaa Xaa Xaa Xaa Xaa Xaa
1               5
```

DETERGENT COMPOSITIONS AND USES THEREOF

CROSS-REFERENCE TO RELATED APPLICATIONS

This application is a 35 U.S.C. 371 national application of PCT/EP2017/060252 filed Apr. 28, 2017, which claims priority or the benefit under 35 U.S.C. 119 of Denmark application PA 2016 00261 filed Apr. 29, 2016, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to cleaning compositions comprising one or more polypeptides having hexosaminidase activity, use of polypeptides having hexosaminidase activity in cleaning processes e.g. cleaning processes for deep cleaning of an item and methods for deep cleaning of an item. The invention further relates to polypeptides having hexosaminidase activity, nucleic acid constructs, vectors, and host cells comprising the polynucleotides as well as methods of producing and using the polypeptides.

Description of the Related Art

Polypeptides having hexosaminidase activity include dispersins such as Dispersin B (DspB) which are β-N-acetyl-glucosamininidases belonging to the Glycoside Hydrolase 20 family ($GH_{20}$). Dispersin B is produced by the periodontal pathogen, *Aggregatibacter actinomycetemcomitans*, a Gram-negative oral bacterium. Dispersin B is a β-hexosaminidase that specifically hydrolyzes β-1,6-glycosidic linkages of acetylglucosamine polymers e.g. found in biofilm. Dispersin B contains three highly conserved acidic residues: an aspartic acid at residue 183 (D183), a glutamic acid at residue 184 (E184), and a glutamic acid at residue 332 (E332). Biofilm have been found attached to various surfaces including medical devices such as implants. WO04061117 A2 (Kane Biotech INC) describe use of compositions comprising DspB for reducing biofilm caused by poly-N-acetylglucosamine-producing bacteria and Kane et al. describes the use of compositions for reduction of biofilm on medical devises and for wound care. Biofilm may also be present on laundry items, such as fabrics, other hard surfaces, such as dish wash utensils, dish washers and washing machines where they may cause malodor, which is difficult to remove and may sustain even after wash. The present invention provides suitable enzymes for use in cleaning compositions e.g. detergents and for deep cleaning of laundry item as well as cleaning processes.

SUMMARY OF THE INVENTION

The present invention relates to a cleaning composition comprising one or more polypeptides having hexosaminidase activity, wherein:
(a) the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings.

The invention also relates to a polypeptide having hexosaminidase activity, selected from the group consisting of:
(a) a polypeptide having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 20;

The invention further relates to a cleaning composition comprising one or more polypeptides having hexosaminidase activity, wherein:
(a) the polypeptide comprises one or more Glyco_hydro_20 catalytic domains, wherein the polypeptide comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41); and
(b) at least one cleaning ingredient.

The invention further relates to the use of a composition of the invention for deep-cleaning of an item, wherein the item is a textile. The invention also relates to a method for laundering an item comprising the steps of:
a. exposing an item to a wash liquor comprising a polypeptide having at least 60%, e.g. 80%, 85%, 90%, 95% or 100% sequence identity to the polypeptide of SEQ ID NO 20, SEQ ID NO 33, SEQ ID NO 34, SEQ ID NO 35, SEQ ID NO 36 or a detergent composition according to any of claims 1 to 10;
b. Completing at least one wash cycle; and
c. Optionally rinsing the item, wherein the item is a textile.

The invention further relates to a polypeptide having hexosaminidase activity, selected from the group consisting of:
(a) a polypeptide having at least 80% sequence identity to the polypeptide of SEQ ID NO 20;
(b) a polypeptide having at least 80% sequence identity to the polypeptide of SEQ ID NO 33;
(c) a polypeptide having at least 80% sequence identity to the polypeptide of SEQ ID NO 34;
(d) a polypeptide having at least 80% sequence identity to the polypeptide of SEQ ID NO 35;
(e) a variant of the polypeptide selected from the group consisting of SEQ ID NO 20, SEQ ID NO 33, SEQ ID NO 34 or SEQ ID NO 35, wherein the variant has hexosaminidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(f) a polypeptide comprising the polypeptide of (a) to (d) and a N-terminal and/or C-terminal His-tag and/or HQ-tag;
(g) a polypeptide comprising the polypeptide of (a) to (d) and a N-terminal and/or C-terminal extension of between 1 and 10 amino acids;
(h) a fragment of the polypeptide of (a) to (d) having hexosaminidase activity and having at least 90% of the length of the mature polypeptide;

(i) a polypeptide comprising one or more of the motifs [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) or DPRIH (SEQ ID NO 45); and (j) a polypeptide having β-N-acetylglucosamininidase activity.

The invention further relates to compositions comprising the hexosaminidase of the invention; use of the hexosaminidase of the invention in cleaning compositions, in the preparation of a composition for use in cleaning, and isolated polynucleotides encoding the polypeptides of the invention.

Overview of Sequence Listing

SEQ ID NO 1 is the amino acid sequence of the GH20 catalytic domain of SWISSPROT:Q6GYA5 from *Actinobacillus pleuropneumoniae*.

SEQ ID NO 2 is the amino acid sequence of the GH20 catalytic domain of SWISSPROT:G4AQA6 from *Aggregatibacter actinomycetemcomitans*.

SEQ ID NO 3 is the amino acid sequence of the GH20 catalytic domain of SWISSPROT:A6VMN2 from *Actinobacillus succinogenes*.

SEQ ID NO 4 is the amino acid sequence of the GH20 catalytic domain of SWISSPROT:G4CNH0 from *Neisseria wadsworthii*.

SEQ ID NO 5 is the amino acid sequence of the GH20 catalytic domain of SEQ ID 9 from *Actinobacillus capsulatus*.

SEQ ID NO 6 is the amino acid sequence of the GH20 catalytic domain of SEQ ID 10 from *Terribacillus goriensis*.

SEQ ID NO 7 is the amino acid sequence of the GH20 catalytic domain of SEQ ID 11 from *Terribacillus saccharophilus*.

SEQ ID NO 8 is the amino acid sequence of the catalytic domain of SEQ ID 12 from *Curtobacterium oceanosedimentum*.

SEQ ID NO 9 is the amino acid sequence derived from SEQ ID 13 from *Actinobacillus capsulatus*.

SEQ ID NO 10 is the amino acid sequence derived from SEQ ID 14 from *Terribacillus goriensis*.

SEQ ID NO 11 is the amino acid sequence derived from SEQ ID 15 from *Terribacillus saccharophilus*.

SEQ ID NO 12 is the amino acid sequence derived from SEQ ID 16 from *Curtobacterium oceanosedimentum*.

SEQ ID NO 13 is the DNA encoding the full-length polypeptide from *Actinobacillus capsulatus*.

SEQ ID NO 14 is the DNA encoding the full-length polypeptide from *Terribacillus goriensis*.

SEQ ID NO 15 is the DNA encoding the full-length polypeptide from *Terribacillus saccharophilus*.

SEQ ID NO 16 is the DNA encoding the full-length polypeptide from *Curtobacterium oceanosedimentum*.

SEQ ID NO 17 is the mature polypeptide of SEQ ID 13 from *Actinobacillus capsulatus*.

SEQ ID NO 18 is the mature polypeptide of SEQ ID 14 from *Terribacillus goriensis*.

SEQ ID NO 19 is the mature polypeptide of SEQ ID 15 from *Terribacillus saccharophilus*.

SEQ ID NO 20 is the mature polypeptide of SEQ ID 16 from *Curtobacterium oceanosedimentum*

SEQ ID NO 21 is conserved [IV]P[ED][LVI]DXP[AN]H
SEQ ID NO 22 is conserved motif II NYN[AS]Y[SY]LY SEQ ID NO 23 *Bacillus clausii* secretion signal MKKPLGKIVASTALLISVAFSSSIASA SEQ ID NO 24 His-tag HHHHHHPR SEQ ID NO 25 is the amino acid sequence derived from SEQ ID NO 29 from *Curtobacterium flaccumfaciens*

SEQ ID NO 26 is the amino acid sequence derived from SEQ ID NO 30 from *Curtobacterium luteum*

SEQ ID NO 27 is the amino acid sequence derived from SEQ ID NO 31 from *Curtobacterium oceanosedimentum*

SEQ ID NO 28 is the amino acid sequence derived from SEQ ID NO 32 from *Curtobacterium sp. Leaf154*

SEQ ID NO 29 is the DNA encoding the full-length polypeptide from *Curtobacterium flaccumfaciens*

SEQ ID NO 30 is the DNA encoding the full-length polypeptide from *Curtobacterium luteum*

SEQ ID NO 31 is the DNA encoding the full-length polypeptide from *Curtobacterium oceanosedimentum*

SEQ ID NO 32 is the DNA encoding the full-length polypeptide from *Curtobacterium sp. Leaf154*

SEQ ID NO 33 is the mature polypeptide of SEQ ID 25 from *Curtobacterium flaccumfaciens*

SEQ ID NO 34 is the mature polypeptide of SEQ ID 26 from *Curtobacterium luteum*

SEQ ID NO 35 is the mature polypeptide of SEQ ID 27 from *Curtobacterium oceanosedimentum*

SEQ ID NO 36 is the mature polypeptide of SEQ ID 28 from *Curtobacterium Leaf154*

SEQ ID NO 37 is the amino acid sequence of the catalytic domain of SEQ ID 25 from *Curtobacterium flaccumfaciens*.

SEQ ID NO 38 is the amino acid sequence of the catalytic domain of SEQ ID 26 from *Curtobacterium luteum*.

SEQ ID NO 39 is the amino acid sequence of the catalytic domain of SEQ ID 27 from *Curtobacterium oceanosedimentum*.

SEQ ID NO 40 is the amino acid sequence of the catalytic domain of SEQ ID 28 from *Curtobacterium Leaf154*

SEQ ID NO 41 is the polypeptide motif GXDE
SEQ ID NO 42 is the polypeptide motif ARAYYPV
SEQ ID NO 43 is the polypeptide motif AWNDGID
SEQ ID NO 44 is the polypeptide motif DDQNVGI
SEQ ID NO 45 is the polypeptide motif DPRIH
SEQ ID NO 46 is the polypeptide motif [EQ][NRSHA][YVFL][AGSTC][IVLF][EAQYN][SN]

BRIEF DESCRIPTION OF THE FIGURES

FIG. 1 shows an alignment of the polypeptides of the invention comprised in the ARAY clade.

FIG. 2 shows a phylogenetic tree of the ARAY clade.

DEFINITIONS

Dispersin: The term "dispersin" and the abbreviation "Dsp" means a polypeptide having hexosaminidase activity, EC 3.2.1.—that catalyzes the hydrolysis of β-1,6-glycosidic linkages of N-acetyl-glucosamine polymers (poly-N-acetyl-glucosamine) found e.g. in biofilm.

Hexosaminidase: The term "hexosaminidases" means a polypeptide having hexosaminidase activity (hexosaminidases), and includes EC 3.2.1.e.g. that catalyzes the hydrolysis of of N-acetyl-D-hexosamine or N-acetyl-glucosamine polymers found e.g. in biofilm. The term includes dispersins and includes polypeptides having N-acetylglucosaminidase activity and β-N-acetylglucosamininidase activity. The term "polypeptide having hexosaminidase activity" may be used interchangeably with the term hexosaminidases and similar the term "polypeptide having β-N-acetylglucosamininidase activity" may be used interchangeably with the term 6-N-acetylglucosamininidases. For the purposes of the present invention, hexosaminidase activity is determined according to the procedure described in Assay 1 or 2. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO 20, SEQ ID NO 33, SEQ ID NO 34 or SEQ ID NO 35.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm may be produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry and hard surfaces biofilm producing bacteria can be found among the following species: *Acinetobacter* sp., *Aeromicrobium* sp., *Brevundimonas* sp., *Microbacterium* sp *Micrococcus luteus*, *Pseudomonas* sp., *Streptococcus* sp., *Streptococcus dysgalactiae*, *Staphylococcus epidermidis*, *Staphylococcus aureus*, *Staphylococcus pneumoniae*, *Stenotrophomonas* sp., *Enterobacter* sp., *Xanthomonas* sp., *Yersinia* sp., *Klebsiella* sp., *Burkholderia* sp., *Stenotrophomonas* sp., *Variovorax* sp., *Escherichia* sp., *Ralstonia* sp., *Achromobacter* sp., *Luteibacter* sp., *Citrobacter* sp., *Xanthomonadaceae* sp., *Halomonas* sp., *Bordetella* sp., *Lysobacter* sp., *Serratia* sp., *Escherichia* sp., *Aggregatibacter* sp., *Listeria monocytogenes*, *Clostridium difficile*, *Mycobacterium* sp., *Neisseria gonorrheae*, *H. influenzae*, *Haemophilus ducreyi*, *Helicobacter pylori*, *Campylobacter jejuni* and *Enterococcus faecalis* as well as the fungi *Candida albicans*, *Aspergillus flavus*, *Fusarium solani*, and *Cryptococcus neoformans*. In one aspect, the biofilm component e.g. poly-N-acetylglucosamine comprising strain is *Brevundimonas* sp. In one aspect, the biofilm component e.g. poly-N-acetylglucosamine comprising strain is *Pseudomonas alcaliphila* or *Pseudomonas fluorescens*. In one aspect, the biofilm component e.g. poly-N-acetylglucosamine comprising strain is *Staphylococcus aureus*.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant reduction or removal of components of biofilm, such as EPS or parts hereof, polysaccharides, poly-N-acetylglucosamine (PNAG), proteins, DNA, soil or other components present in the biofilm.

Detergent adjunct ingredient: The cleaning e.g. detergent adjunct ingredient is different to the hexosaminidases of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Cleaning e.g. Detergent Composition: The terms "cleaning" and/or "detergent composition" refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, color clarification of the fabric and removal of particulate soils which are trapped in the fibers of the fabric or garment.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has hexosaminidase activity. In one aspect, a fragment contains at least 350 amino acid residues (e.g., amino acids 105 to 454 of SEQ ID NO 20), at least 355 amino acid residues (e.g., amino acids 100 to 454 of SEQ ID NO 20), at least 360 amino acid residues (e.g., amino acids 100 to 459 of SEQ ID NO 20) or at least 450 amino acid residues (e.g., amino acids 5 to 454 of SEQ ID NO 20) or at least 450 amino acid residues (e.g., amino acids 1 to 450 of SEQ ID NO 20). In one aspect, a fragment contains at least 300 amino acid residues (e.g., amino acids 1 to 300 of SEQ ID NO 33), at least 350 amino acid residues (e.g., amino acids 1 to 350 of SEQ ID NO 33), at least 340 amino acid residues (e.g., amino acids 10 to 349 of SEQ ID NO 33) or at least 400 amino acid residues (e.g., amino acids 5 to 404 of SEQ ID NO 33) or at least 440 amino acid residues (e.g., amino acids 1 to 440 of SEQ ID NO 33). In one aspect, a fragment contains at least 300 amino acid residues (e.g., amino acids 1 to 300 of SEQ ID NO 34), at least 350 amino acid residues (e.g., amino acids 1 to 350 of SEQ ID NO 34), at least 340 amino acid residues (e.g., amino acids 10 to 349 of SEQ ID NO 34) or at least 400 amino acid residues (e.g., amino acids 5 to 404 of SEQ ID NO 34) or at least 440 amino acid residues (e.g., amino acids 1 to 440 of SEQ ID NO 34). In one aspect, a fragment contains at least 350 amino acid residues (e.g., amino acids 105 to 454 of SEQ ID NO 35), at least 355 amino acid residues (e.g., amino acids 100 to 454 of SEQ ID NO 35), at least 360 amino acid residues (e.g., amino acids 100 to 459 of SEQ ID NO 35) or at least 450 amino acid residues (e.g., amino acids 5 to 454 of SEQ ID NO 35) or at least 450 amino acid residues (e.g., amino acids 1 to 450 of SEQ ID NO 35). In one aspect, a fragment contains at least 300 amino acid residues (e.g., amino acids 1 to 300 of SEQ ID NO 34), at least 290 amino acid residues (e.g., amino acids 1 to 290 of SEQ ID NO 34), at least 275 amino acid residues (e.g., amino acids 10 to 284 of SEQ ID NO 34) or at least 270 amino acid residues (e.g., amino acids 5 to 274 of SEQ ID NO 34) or at least 260 amino acid residues (e.g., amino acids 1 to 260 of SEQ ID NO 34).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Improved wash performance: The term "improved wash performance" is defined herein as an enzyme displaying an increased wash performance in a detergent composition relative to the wash performance of same detergent composition without the enzyme e.g. by increased stain removal or less re-deposition. The term "improved wash performance" includes wash performance in laundry.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: The term "malodor" means an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide consisting essentially of amino acids 27 to 378 of SEQ ID NO 9 and amino acids 1 to 26 of SEQ ID NO 9 comprise a signal peptide. In one aspect, the mature is the polypeptide is the amino acid sequence shown in SEQ ID NO 17. In another aspect, the mature polypeptide consisting essentially of amino acids 26 to 349 of SEQ ID NO 10 and amino acids 1 to 25 of SEQ ID NO 10 are a signal peptide. In one aspect, the mature is the polypeptide is the amino acid sequence shown in SEQ ID NO 18. In another aspect, the mature polypeptide consisting essentially of amino acids 42 to 365 of SEQ ID NO 11 and amino acids 1 to 41 of SEQ ID NO 11 are a signal peptide. In one aspect, the mature is the polypeptide is the amino acid sequence shown in SEQ ID NO 19. In another aspect, the mature polypeptide consisting essentially of amino acids 25 to 485 of SEQ ID NO 12 and amino acids 1 to 24 of SEQ ID NO 12 are a signal peptide. In one aspect, the mature polypeptide is the amino acid sequence shown in SEQ ID NO 20. In another aspect, the mature polypeptide consisting essentially of amino acids 42 to 486 of SEQ ID NO 25 and amino acids 1 to 41 of SEQ ID NO 25 are a signal peptide. In one aspect, the mature polypeptide is the amino acid sequence shown in SEQ ID NO 33. In another aspect, the mature polypeptide consisting essentially of amino acids 42 to 486 of SEQ ID NO 26 and amino acids 1 to 41 of SEQ ID NO 26 are a signal peptide. In one aspect, the mature polypeptide is the amino acid sequence shown in SEQ ID NO 34. In another aspect, the mature polypeptide consisting essentially of amino acids 24 to 481 of SEQ ID NO 27 and amino acids 1 to 23 of SEQ ID NO 27 are a signal peptide. In one aspect, the mature polypeptide is the amino acid sequence shown in SEQ ID NO 35. In another aspect, the mature polypeptide consisting essentially of amino acids 26 to 475 of SEQ ID NO 28 and amino acids 1 to 25 of SEQ ID NO 28 are a signal peptide. In one aspect, the mature polypeptide is the amino acid sequence shown in SEQ ID NO 36.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having hexosaminidase activity. In one aspect, the mature polypeptide coding sequence consisting essentially of nucleotides 73 to 1455 of SEQ ID NO 16 or the cDNA sequence thereof and nucleotides 1 to 72 of SEQ ID NO 16 are the signal peptide. In one aspect, the mature polypeptide coding sequence consisting essentially of nucleotides 124 to 1458 of SEQ ID NO 29 or the cDNA sequence thereof and nucleotides 1 to 123 of SEQ ID NO 29 are the signal peptide. In one aspect, the mature polypeptide coding sequence consisting essentially of nucleotides 124 to 1458 of SEQ ID NO 30 or the cDNA sequence thereof and nucleotides 1 to 123 of SEQ ID NO 30 are the signal peptide. In one aspect, the mature polypeptide coding sequence consisting essentially of nucleotides 70 to 1443 of SEQ ID NO 31 or the cDNA sequence thereof and nucleotides 1 to 69 of SEQ ID NO 31 are the signal peptide.

In one aspect, the mature polypeptide coding sequence consisting essentially of nucleotides 76 to 1425 of SEQ ID NO 32 or the cDNA sequence thereof and nucleotides 1 to 75 of SEQ ID NO 32 are the signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic and/or which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows:

(Identical Residues×100)/(Length of Alignment–
Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.8×SSC, 0.2% SDS at 55° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.8×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.8×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.8×SSC, 0.2% SDS at 70° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.4×SSC, 0.2% SDS at 70° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.4×SSC, 0.2% SDS at 75° C.

Subsequence: The term "subsequence" means a polynucleotide having one or more (e.g., several) nucleotides absent from the 5' and/or 3' end of a mature polypeptide coding sequence; wherein the subsequence encodes a fragment having hexosaminidase activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having hexosaminidase activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, 3, 4, 5 etc. amino acids adjacent to and immediately following the amino acid occupying the position.

In one aspect, a hexosaminidase variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the hexosaminidase activity of the parent hexosaminidase, such as SEQ ID NO 20.

In one aspect, a hexosaminidase variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the hexosaminidase activity of the parent hexosaminidase, such as SEQ ID NO 33.

In one aspect, a hexosaminidase variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the hexosaminidase activity of the parent hexosaminidase, such as SEQ ID NO 34.

In one aspect, a hexosaminidase variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the hexosaminidase activity of the parent hexosaminidase, such as SEQ ID NO 35.

In one aspect, a hexosaminidase variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the hexosaminidase activity of the parent hexosaminidase, such as SEQ ID NO 36.

Nomenclature

For purposes of the present invention, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

The present invention relates to polypeptides having hexosaminidase activity preferably PNAG (poly-N-acetyl-glucosamine) activity. Organic matter such as biofilm produces EPS (extra polymeric substances), which often comprises polysaccharides such as PNAG. The polypeptides of the invention are therefore effective in preventing, reducing and removing organic components such as PNAG. Organic matter such as biofilm associated with cleaning processes e.g. in textiles such as laundry is an important challenge since it may be associated with consumer relevant problems such as e.g. malodor and re-deposition. Several attempts have been made to solve various aspects of biofilm related problems in laundry many of which relate to removal of malodor. WO2014/087011 describes the use of a deoxyribonuclease (DNase) and other enzymes for reducing malodor from laundry and/or textile, WO99/09143 describes the use of one or more oxidoreductases in combination with a mediator for the reduction of malodor and WO2012/112718 describes a method for inhibiting production of laundry malodor caused by bacteria by using various strains of *Bacillus*. The present invention relates to polypeptides and cleaning e.g. detergent compositions comprising polypeptides preferably having a Glyco_hydro_20 catalytic domains as defined PFAM (PF00728, Pfam version 31.0 Finn (2016). Nucleic Acids Research, Database Issue 44: D279-D285) optionally wherein the GH20 catalytic domain gives a domT score of 150 or more when queried using a Profile Hidden Markov Model prepared using SEQ ID NOs: 1 to 7 using the software program hmmbuild, the query being carried out using the hmmscan software program with default settings and wherein the polypeptide has hexosaminidase activity. In one aspect, the Glyco_hydro_20 catalytic domain is selected from the conserved motif I [IV]P[ED][LVI]DXP[AN]H (SEQ ID NO 21) and conserved motif II NYN[AS]Y[SY]LY (SEQ ID NO 22). The polypeptides of the invention preferably comprise an additional motif GXDE (SEQ ID NO 41) situated in positions corresponding to positions 275 to 278 in *Curtobacterium luteum* (SEQ ID NO 34). Residues D and E are the key catalytic residues of hexosaminidases (position 277 to 278 in SEQ ID NO 34).

One aspect of the invention relates to polypeptides comprising one or more of the motif(s) [IV]P[ED][LVI]DXP[AN]H (SEQ ID NO 21), NYN[AS]Y[SY]LY (SEQ ID NO 22) or GXDE (SEQ ID NO 41), wherein the polypeptides have hexosaminidase activity, preferably n-N-acetylglucosamininidase activity, such as PNAG activity. In one particular aspect, of the invention the polypeptide is obtained from the genus *Curtobacterium*. Preferably the polypeptides belong to the ARAY clade which comprises polypeptides of bacterial origin, having PNAG activity. The polypeptides of the clade comprise the motif example ARAYYPV (SEQ ID NO 42), corresponding to pos 124 to 130 of SEQ ID NO 34, where Rat position 125 in SEQ ID NO 34 is part of the active site. Another motif which may be comprised by the polypeptides of the ARAY clade is AWNDGID (SEQ ID NO 43), corresponding to 306 to 312 in SEQ ID NO 34. A further motif which may be comprised by the polypeptides of the ARAY clade is DDQNVGI (SEQ ID NO 44), corresponding to amino acids 154 to 160 in SEQ ID NO 34. An additional motif which may be comprised by the polypeptides of the ARAY clade is DPRIH (SEQ ID NO 45), corresponding to amino acids 320 to 324 in SEQ ID NO 34

One aspect of the invention relates to polypeptides comprising one or more of the motif(s) [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) or DPRIH (SEQ ID NO 45), wherein the polypeptides have hexosaminidase activity, preferably β-N-acetylglucosamininidase activity, such as PNAG activity.

Figure 1:
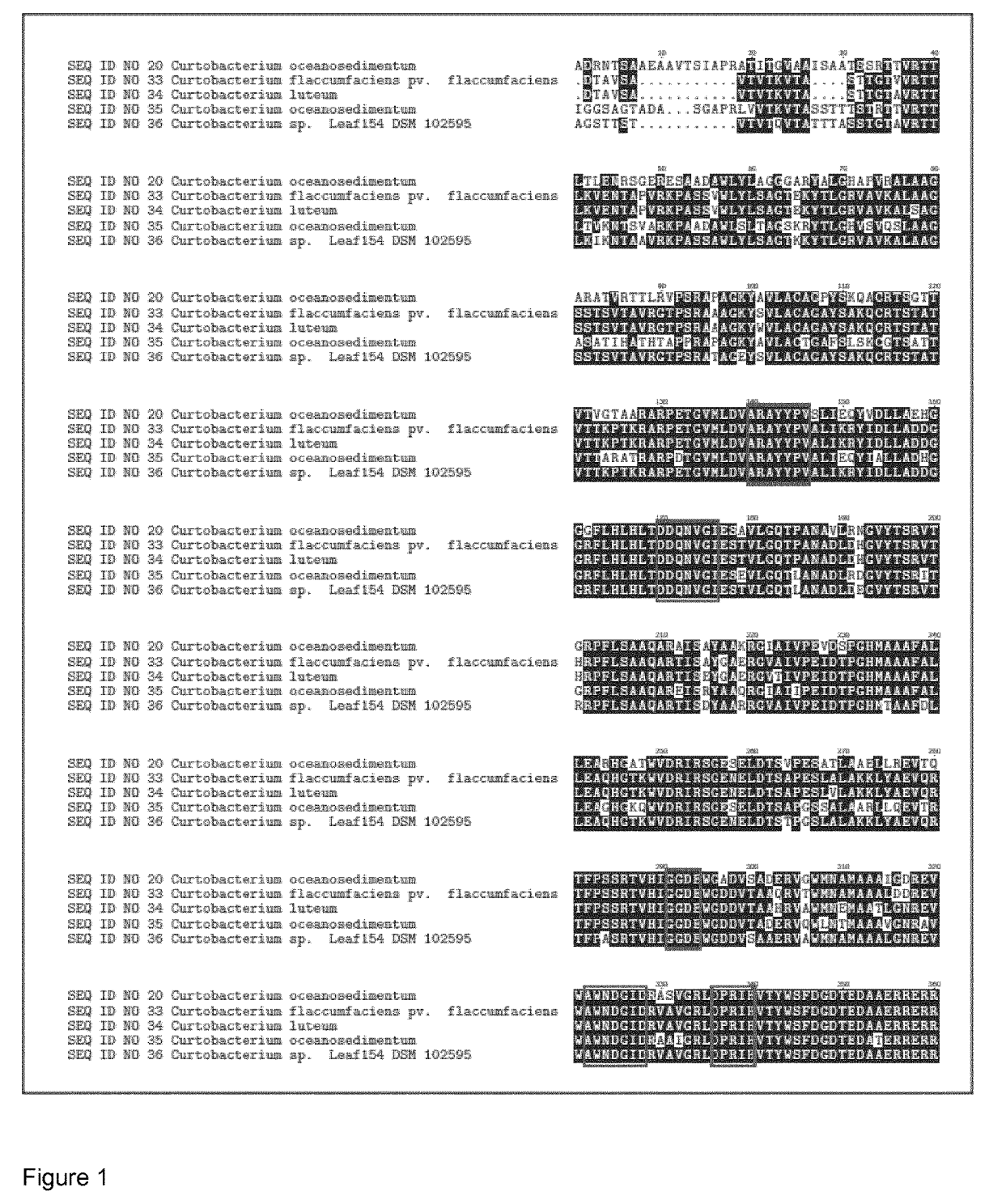

An alignment of the polypeptides of the invention comprised in the clade is shown in FIG. 1. A phylogenetic tree of the ARAY clade is shown in FIG. 2.

Also claimed are laundering methods and method for deep cleaning of an item such as a hard surface or a textile and the use of a polypeptide comprising Glyco_hydro_20 catalytic domain, which has hexosaminidase activity. In particular, polypeptides comprising one or more Glyco_hydro_20 catalytic domains, such as the conserved motif I [IV]P[ED][LVI]DXP[AN]H (SEQ ID NO 21), conserved motif II NYN[AS]Y[SY]LY (SEQ ID NO 22) or conserved motif III GXDE (SEQ ID NO 41) and which have hexosaminidase activity are useful in laundering methods for deep cleaning of items being washed. The inventors have surprisingly found that polypeptides having hexosaminidase activity and which comprises one or more GH20 catalytic domain, wherein the GH20 catalytic domain gives a domT score of 150 or more when queried as described above e.g. polypeptides comprising one or more of the motifs [IV]P[ED][LVI]DXP[AN]H, NYN[AS]Y[SY]LY or GXDE are particularly useful for deep cleaning of laundry and hard surfaces. Dispersin B (DspB) which belongs to the GH20 family is known for its PNAG removal and reduction properties e.g. WO200406117 describe compositions comprising DspB. The composition may include a detergent, which may be anionic, cationic, or non-ionic. However, there is no indication in the art of the use of DspB in cleaning processes such as laundry or in detergent compositions comprising e.g. builders and/or bleaches. To be useful in cleaning processes the enzymes need to perform its action in detergents under the conditions of cleaning processes such as laundry, which includes stability in the presence of detergent components such as surfactants, builders and bleach components. The components of a detergent may significantly effect on the performance of the enzymes such as DspB. The present application relates to another group of dispersins, which are distinguishable from dispersin B. The polypeptides having hexosaminidase activity preferably comprises one or all the motifs [IV]P[ED][LVI]DXP[AN]H (SEQ ID NO 21), NYN[AS]Y[SY]LY (SEQ ID NO 22) or GXDE (SEQ ID NO 41), preferably is obtained from *Curtobacterium* and are preferably comprised in the ARAY clade. The ARAY clade comprises polypeptides comprising one or more of the motifs ARAYYPV (SEQ ID NO 42), AWNDGID (SEQ ID NO 43), DDQNVGI (SEQ ID NO 44) or DPRIH (SEQ ID NO 45). The inventors surprisingly show that polypeptides having hexosaminidase activity and which comprises one or more catalytic domain, and optionally one or more of the motifs [IV]P[ED][LVI]DXP[AN]H (SEQ ID NO 21), NYN[AS]Y[SY]LY (SEQ ID NO 22), GXDE (SEQ ID NO 41) and/or one or more of the motifs ARAYYPV (SEQ ID NO 42), AWNDGID (SEQ ID NO 43), DDQNVGI (SEQ ID NO 44) or DPRIH (SEQ ID NO 45), wherein the GH20 catalytic domain preferably gives a domT score of 150 or more when queried as described above, are useful for reduction and/or removing of organic matter e.g. EPS and/or PNAG associated with cleaning e.g. on textiles or washing machines.

For example, the polypeptide of SEQ ID NO 8 comprise a Glyco_hydro_20 catalytic domain and gives a domT score of 282 when queried using a Profile Hidden Markov Model prepared as described below, displays hexosaminidase activity (see Assay 1 and e.g. table 2 of example 4) and deep cleaning capability in the presence of detergent (see table 3 of example 5).

Cleaning Compositions Comprising Polypeptides Having Hexosaminidase Activity

One aspect, the invention relates to a cleaning composition comprising one or more polypeptides having hexosaminidase activity, wherein polypeptide comprises one or more GH20 catalytic domains, wherein:

(a) the polypeptide comprises one or more GH20 catalytic domains, wherein the GH20 catalytic domain gives a domT score of 150 or more when queried using a Profile Hidden Markov Model prepared using SEQ ID NOs: 1 to 7 using the software program hmmbuild, the query being carried out using the hmmscan software program with default settings.

The theory behind Profile HMMs as described in Durbin et al. (Biological sequence analysis: probabilistic models of proteins and nucleic acids, Cambridge University Press, 1998) and Krogh et al. (1994 *J. Mol. Biol.* 235:1501-1531), both incorporated herein by reference, is characterization of a set of proteins based on the probability of each amino acid occurring at each position in the alignment of the proteins of the set.

A GH20 domain is defined in the following manner. SEQ ID NOs: 1 to 7, which are partial sequences of the Uniprot entries or of the polypeptide sequences disclosed herein, as explained in the 'overview of sequence listing' section, are aligned using the software program MUSCLE v3.8.31 with the default settings. Using this alignment, a hidden Markov model (HMM) is built for the GH20 domain as an extension of the state-of-the-art GH20 domain definition. The HMM is constructed using the software program 'hmmbuild' from the package HMMER 3.1b2 (February 2015) (hmmer.org/) and the software is invoked using the default settings.

A GH20 domain is defined to match the above mentioned HMM using the software program 'hmmscan' from the package HMMER 3.1b2 (February 2015) (hmmer.org/) using the default settings if the domT score is 150 or more. In a preferred embodiment, the domT score is 160 or more, preferably 180 or more, more preferably 190 or more, even more preferably 200 or more, or most preferably 250 or more.

The HMM profile of the GH20 domain as generated using SEQ ID NOs: 1 to 7 according to the procedure above is given in example 1. The HMM profile can be copied into a text file which is subsequently loaded into the software program 'hmmscan' so that other polypeptides can be tested to see whether the polypeptide comprises one or more GH20 catalytic domains.

Likewise, the HMM profile of the Glyco_hydro_20 domain has been generated by Pfam (PF00728, pfam.xfam.org/family/PF00728) using hmmbuild and parameters specified (pfam.xfam.org/family/PF00728#tabview=tab6). The HMM profile can be obtained from Pfam (pfam.xfam.org/family/PF00728) and copied into a text file which is subsequently loaded into the software program 'hmmscan' so that other polypeptides can be tested to see whether the polypeptide comprises one or more Glyco_hydro_20 catalytic domains. In some aspects, the invention relates to a cleaning composition comprising one or more polypeptides having hexosaminidase activity, wherein polypeptide comprises one or more Glyco_hydro_20 catalytic domains, wherein the Glyco_hydro_20 catalytic domain comprises one or more motifs selected from motif I: [IV]P[ED][LVI]DXP[AN]H (SEQ ID NO 21) or one or more motif II NYN[AS]Y[SY]LY (SEQ ID NO 22).

Some aspects of the invention relate to the use in a cleaning process of a polypeptide comprising a GH20 catalytic domain having a domT score of 150 or more when queried using a Profile Hidden Markov Model prepared using SEQ ID NOs: 1 to 7 using the software program hmmbuild as describe above, preferably comprising one or more motifs selected from motif I: [IV]P[ED][LVI]DXP[AN]H (SEQ ID NO 21) and/or one or more motif II NYN[AS]Y[SY]LY (SEQ ID NO 22), wherein the polypeptide has hexosaminidase activity. Some aspects of the invention relates to detergent compositions comprising a) a polypeptide comprising a GH20 catalytic domain having a domT score of 150 or more when queried using a Profile Hidden Markov Model prepared using SEQ ID NOs: 1 to 7 using the software program hmmbuild as describe above, preferably comprising one or more motifs selected from motif I: [IV]P[ED][LVI]DXP[AN]H (SEQ ID NO 21) and/or one or more motif II NYN[AS]Y[SY]LY (SEQ ID NO 22), wherein the polypeptide has hexosaminidase activity and b) at least one cleaning ingredient such as a surfactant, preferably at least one surfactant selected from the group consisting of anionic, nonionic and/or cationic surfactants.

One aspect of the invention relates to a cleaning composition comprising one or more polypeptides having hexosaminidase activity, wherein:
 (a) the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, and
 (b) at least one cleaning ingredient.

In a preferred aspect, the polypeptide has N-acetylglucosaminidase activity and/or β-N-acetylglucosamininidase activity. In one aspect, the polypeptide has hexosaminidase activity, preferably N-acetylglucosaminidase activity and/or β-N-acetylglucosamininidase activity and has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20, SEQ ID NO 33, SEQ ID NO 34, SEQ ID NO 35 or SEQ ID NO 36.

One aspect relates to a cleaning composition comprising one or more polypeptides having hexosaminidase activity, preferably N-acetylglucosaminidase activity and/or β-N-acetylglucosamininidase activity wherein:
 (a) the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, and
 (b) at least one cleaning ingredient,
 wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20, SEQ ID NO 33, SEQ ID NO 34, SEQ ID NO 35 or SEQ ID NO 36.

The polypeptides preferably comprise the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41).

One aspect of the invention relates to a cleaning composition comprising one or more polypeptides having hexosaminidase activity, wherein:
 (a) the polypeptide comprises one or more Glyco_hydro_20 catalytic domains, wherein the polypeptide comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41); and
 (b) at least one cleaning ingredient.

The polypeptides having hexosaminidase activity, preferably N-acetylglucosaminidase activity and/or β-N-acetylglucosamininidase activity.

One aspect of the invention relates to a cleaning composition comprising one or more polypeptides having hexosaminidase activity, preferably N-acetylglucosaminidase activity and/or β-N-acetylglucosamininidase activity wherein:
(a) the polypeptide comprises one or more Glyco_hydro_20 catalytic domains, wherein the polypeptide comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41); and
(b) at least one cleaning ingredient.

In one aspect, the polypeptide has hexosaminidase activity, preferably N-acetylglucosaminidase activity and/or β-N-acetylglucosamininidase activity and has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20, SEQ ID NO 33, SEQ ID NO 34, SEQ ID NO 35 or SEQ ID NO 36.

One aspect of the invention relates to a cleaning composition comprising one or more polypeptides having hexosaminidase activity, preferably N-acetylglucosaminidase activity and/or β-N-acetylglucosamininidase activity wherein:
(a) the polypeptide comprises one or more Glyco_hydro_20 catalytic domains, wherein the polypeptide comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41); and
(b) at least one cleaning ingredient,
wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20, SEQ ID NO 33, SEQ ID NO 34, SEQ ID NO 35 or SEQ ID NO 36.

The polypeptide preferably comprises one or more of the motifs ARAYYPV (SEQ ID NO 42), AWNDGID (SEQ ID NO 43), DDQNVGI (SEQ ID NO 44) or DPRIH (SEQ ID NO 45).

One aspect of the invention relates to a cleaning composition comprising one or more polypeptides having hexosaminidase activity, preferably N-acetylglucosaminidase activity and/or β-N-acetylglucosamininidase activity wherein:
(a) the polypeptide comprises one or more Glyco_hydro_20 catalytic domains, wherein the polypeptide comprises one or more of the motifs ARAYYPV (SEQ ID NO 42), AWNDGID (SEQ ID NO 43), DDQNVGI (SEQ ID NO 44) or DPRIH (SEQ ID NO 45); and
(b) at least one cleaning ingredient.

One aspect of the invention relates to a cleaning composition comprising one or more polypeptides having hexosaminidase activity, preferably N-acetylglucosaminidase activity and/or β-N-acetylglucosamininidase activity wherein:
(a) the polypeptide comprises one or more Glyco_hydro_20 catalytic domains, wherein the polypeptide comprises one or more of the motifs ARAYYPV (SEQ ID NO 42), AWNDGID (SEQ ID NO 43), DDQNVGI (SEQ ID NO 44) or DPRIH (SEQ ID NO 45); and
(b) at least one cleaning ingredient,
wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20, SEQ ID NO 33, SEQ ID NO 34, SEQ ID NO 35 or SEQ ID NO 36.

The amount of polypeptide may be in the range of 0.00004-100 ppm, such as in the range of 0.00008-50 ppm, in the range of 0.00001-20, in the range of 0.0002-20 ppm, in the range of 0.0001-50 ppm, in the range of 0.0002-50, in the range of 0.0004-50, in the range of 0.0008-50, in the range of 0.001-50 ppm, 0.01-50 ppm, preferably 0.0001-50 ppm, more preferably 0.0002-20 ppm, more preferably 0.0002-10 ppm, more preferably 0.001-10 ppm, and most preferably 0.002-10 ppm. The hexosaminidase of the present invention may be in an amount corresponding to at least 0.00001 ppm, such as at least 0.00002 ppm, at least 0.0001 ppm, at least 0.0002 ppm, at least 0.0005 ppm, at least 0.001 ppm, at least 0.002 mg ppm, at least 0.005 ppm, at least 0.01 ppm or at least 0.02 ppm. The composition may comprise at least 0.00008%, preferably at least 0.0000.1%, 0.00002%, 0.000.1%, 0.0002%, 0.001%, 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% hexosaminidase.

One aspect, relates to cleaning composition comprising one or more polypeptides having hexosaminidase activity, wherein:
(a) the polypeptide comprises one or more Glyco_hydro_20 catalytic domains, wherein the polypeptide comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41); and
(b) at least one cleaning ingredient, wherein the cleaning ingredient is selected from,
a) at least one builder,
b) at least one surfactant, and
c) at least one bleach component.

Some aspect of the invention relate to detergent compositions comprising a) a polypeptide comprising a Glyco_hydro_20 catalytic domain, preferably comprising one or both motif(s) [IV]P[ED][LVI]DXP[AN]H (SEQ ID NO 21) or NYN[AS]Y[SY]LY (SEQ ID NO 22), wherein the polypeptide is selected from polypeptides comprising an amino acid sequence shown in SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 37, SEQ ID NO 38, SEQ ID NO 39, SEQ ID NO 40 and polypeptides having at least 60% e.g. 80%, 85%, 90%, 95%, 98% or 100% sequence identity hereto, wherein the polypeptide has hexosaminidase activity and b) at least one cleaning ingredient such as a surfactant, preferably at least one surfactant selected from the group consisting of anionic, nonionic and/or cationic surfactants.

Some aspects of the invention relate the use in a cleaning process of a polypeptide comprising SEQ ID NO 20 or a polypeptide having at least 60% e.g. 80%, 85%, 90%, 95%, 98% or 100% sequence identity hereto, wherein the polypeptide has hexosaminidase activity. Some aspects of the invention relate to detergent compositions comprising a) a polypeptide comprising the amino acid sequence shown in SEQ ID NO 20 or a polypeptide having at least 60% e.g. 80%, 85%, 90%, 95%, 98% or 100% sequence identity hereto, wherein the polypeptide has hexosaminidase activity and b) at least one surfactant, preferably at least one surfactant selected from the group consisting of anionic, non-ionic and/or cationic surfactants.

Some aspects of the invention relate the use in a cleaning process of a polypeptide comprising SEQ ID NO 33 or a polypeptide having at least 60% e.g. 80%, 85%, 90%, 95%, 98% or 100% sequence identity hereto, wherein the polypeptide has hexosaminidase activity. Some aspects of the invention relate to detergent compositions comprising a) a polypeptide comprising the amino acid sequence shown in SEQ ID NO 33 or a polypeptide having at least 60% e.g. 80%, 85%, 90%, 95%, 98% or 100% sequence identity hereto, wherein the polypeptide has hexosaminidase activity and b) at least one surfactant, preferably at least one surfactant selected from the group consisting of anionic, non-ionic and/or cationic surfactants.

Some aspects of the invention relate the use in a cleaning process of a polypeptide comprising SEQ ID NO 34 or a polypeptide having at least 60% e.g. 80%, 85%, 90%, 95%, 98% or 100% sequence identity hereto, wherein the polypeptide has hexosaminidase activity. Some aspects of the invention relate to detergent compositions comprising a) a polypeptide comprising the amino acid sequence shown in SEQ ID NO 34 or a polypeptide having at least 60% e.g. 80%, 85%, 90%, 95%, 98% or 100% sequence identity hereto, wherein the polypeptide has hexosaminidase activity and b) at least one surfactant, preferably at least one surfactant selected from the group consisting of anionic, non-ionic and/or cationic surfactants.

Some aspects of the invention relate the use in a cleaning process of a polypeptide comprising SEQ ID NO 35 or a polypeptide having at least 60% e.g. 80%, 85%, 90%, 95%, 98% or 100% sequence identity hereto, wherein the polypeptide has hexosaminidase activity. Some aspects of the invention relate to detergent compositions comprising a) a polypeptide comprising the amino acid sequence shown in SEQ ID NO 35 or a polypeptide having at least 60% e.g. 80%, 85%, 90%, 95%, 98% or 100% sequence identity hereto, wherein the polypeptide has hexosaminidase activity and b) at least one surfactant, preferably at least one surfactant selected from the group consisting of anionic, non-ionic and/or cationic surfactants.

Some aspects of the invention relate the use in a cleaning process of a polypeptide comprising SEQ ID NO 36 or a polypeptide having at least 60% e.g. 80%, 85%, 90%, 95%, 98% or 100% sequence identity hereto, wherein the polypeptide has hexosaminidase activity. Some aspects of the invention relate to detergent compositions comprising a) a polypeptide comprising the amino acid sequence shown in SEQ ID NO 36 or a polypeptide having at least 60% e.g. 80%, 85%, 90%, 95%, 98% or 100% sequence identity hereto, wherein the polypeptide has hexosaminidase activity and b) at least one surfactant, preferably at least one surfactant selected from the group consisting of anionic, non-ionic and/or cationic surfactants.

Some aspect of the invention relates to a detergent composition comprising:
a) at least 0.01 ppm of active enzyme polypeptide, wherein the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, optionally comprising one or more motifs selected from motif I: [IV]P[ED][LVI]DXP[AN]H (SEQ ID NO 21) and/or one or more motif II NYN[AS]Y[SY]LY (SEQ ID NO 22), and
b) from about 5 wt % to about 60 wt % surfactant.

Some aspect of the invention relates to a detergent composition comprising:
a) at least 0.0001 ppm of active enzyme polypeptide, wherein the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, wherein the polypeptide optionally comprising one or both motif(s) [IV]P[ED][LVI]DXP[AN]H (SEQ ID NO 21) or NYN[AS]Y[SY]LY (SEQ ID NO 22), wherein the polypeptide is selected from polypeptides comprising an amino acid sequence shown in SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 37, SEQ ID NO 38, SEQ ID NO 39, SEQ ID NO 40 and polypeptides having at least 60%, e.g. 80%, 85%, 90%, 95%, 98% or 100% sequence identity hereto, wherein the polypeptide has hexosaminidase activity, and
b) from about 5 wt % to about 60 wt % surfactant.

Some aspect of the invention relates to a detergent composition comprising:
a) at least 0.01 ppm of active enzyme polypeptide comprising SEQ ID NO 20 or a polypeptide having at least 80% sequence identity hereto, wherein the polypeptide has hexosaminidase activity, and
b) from about 5 wt % to about 60 wt % surfactant Some aspect of the invention relates to a detergent composition comprising:
a) at least 0.0001 ppm of active enzyme polypeptide comprising SEQ ID NO 20 or a polypeptide having at least 60%, e.g. 80%, 85%, 90%, 95%, 98% or 100% sequence identity hereto, wherein the polypeptide has hexosaminidase activity, and
b) from about 5 wt % to about 60 wt % surfactant.

Some aspect of the invention relates to a detergent composition comprising:
a) at least 0.01 ppm of active enzyme polypeptide comprising SEQ ID NO 33 or a polypeptide having at least 60%, e.g. 80%, 85%, 90%, 95%, 98% or 100% sequence identity hereto, wherein the polypeptide has hexosaminidase activity, and
b) from about 5 wt % to about 60 wt % surfactant.

Some aspect of the invention relates to a detergent composition comprising:
a) at least 0.01 ppm of active enzyme polypeptide comprising SEQ ID NO 34 or a polypeptide having at least 60%, e.g. 80%, 85%, 90%, 95%, 98% or 100% sequence identity hereto, wherein the polypeptide has hexosaminidase activity, and
b) from about 5 wt % to about 60 wt % surfactant.

Some aspect of the invention relates to a detergent composition comprising:
a) at least 0.01 ppm of active enzyme polypeptide comprising SEQ ID NO 35 or a polypeptide having at least 60%, e.g. 80%, 85%, 90%, 95%, 98% or 100% sequence identity hereto, wherein the polypeptide has hexosaminidase activity, and
b) from about 5 wt % to about 60 wt % surfactant.

Some aspect of the invention relates to a detergent composition comprising:
  a) at least 0.01 ppm of active enzyme polypeptide comprising SEQ ID NO 36 or a polypeptide having at least 60%, e.g. 80%, 85%, 90%, 95%, 98% or 100% sequence identity hereto, wherein the polypeptide has hexosaminidase activity, and
  b) from about 5 wt % to about 60 wt % surfactant The composition may comprise from about 2 wt % to about 60 wt %, from about 5 wt % to about 60 wt % surfactant, from about 5 wt % to about 50 wt %, from about 5 wt % to about 40 wt %, from about 5 wt % to about 30 wt %, from about 5 wt % to about 20 wt % or from about 5 wt % to about 10 wt % of at least one surfactant, wherein the surfactant is anionic, nonionic or cationic. The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C9-C15 alcohol ethersulfates, C12-C15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkyl-benzenesulfonates (LAS), isomers of LAS, branched alkyl-benzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants include Plurafac™, Lutensol™ and Pluronic™ range from BASF, Dehypon™ series from Cognis and Genapol™ series from Clariant.

The polypeptides of the invention may also be formulated in liquid compositions optionally comprising a builder such as liquid laundry compositions comprising:
  a) at least 0.01 ppm of active enzyme polypeptide, wherein the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, preferably comprising one or more motifs selected from motif I: [IV]P[ED][LVI]DXP[AN]H (SEQ ID NO 21) and/or one or more motif II NYN[AS]Y[SY]LY (SEQ ID NO 22),
  b) from about 2 wt % to about 60 wt % of at least one surfactant, and optionally
  c) from about 5 wt % to about 50 wt % of at least one builder such as carbonates, zeolites, phosphate builder, calcium sequestering builders or complexing agents.

In some aspects of the invention liquid laundry compositions comprising:
  a) at least 0.01 ppm of active enzyme polypeptide, wherein the polypeptide comprises SEQ ID NO 20 or a polypeptide having at least 60% sequence identity hereto,
  b) from about 2 wt % to about 60 wt % of at least one surfactant, and optionally
  c) from about 5 wt % to about 50 wt % of at least one builder such as carbonates, zeolites, phosphate builder, calcium sequestering builders or complexing agents.

In some aspects of the invention liquid laundry compositions comprising:
  a) at least 0.0001 ppm of active enzyme polypeptide, wherein the polypeptide comprises SEQ ID NO 20 or a polypeptide having at least 60%, e.g. 80%, 85%, 90%, 95%, 98% or 100% sequence identity hereto,
  b) from about 2 wt % to about 60 wt % of at least one surfactant, and optionally
  c) from about 5 wt % to about 50 wt % of at least one builder such as carbonates, zeolites, phosphate builder, calcium sequestering builders or complexing agents.

In some aspects of the invention liquid laundry compositions comprising:
  a) at least 0.0001 ppm of active enzyme polypeptide, wherein the polypeptide comprises SEQ ID NO 33 or a polypeptide having at least 60%, e.g. 80%, 85%, 90%, 95%, 98% or 100% sequence identity hereto,
  b) from about 2 wt % to about 60 wt % of at least one surfactant, and optionally
  c) from about 5 wt % to about 50 wt % of at least one builder such as carbonates, zeolites, phosphate builder, calcium sequestering builders or complexing agents.

In some aspects of the invention liquid laundry compositions comprising:
  a) at least 0.0001 ppm of active enzyme polypeptide, wherein the polypeptide comprises SEQ ID NO 34 or a polypeptide having at least 60%, e.g. 80%, 85%, 90%, 95%, 98% or 100% sequence identity hereto,
  b) from about 2 wt % to about 60 wt % of at least one surfactant, and optionally
  c) from about 5 wt % to about 50 wt % of at least one builder such as carbonates, zeolites, phosphate builder, calcium sequestering builders or complexing agents.

In some aspects of the invention liquid laundry compositions comprising:
  a) at least 0.0001 ppm of active enzyme polypeptide, wherein the polypeptide comprises SEQ ID NO 35 or a polypeptide having at least 60%, e.g. 80%, 85%, 90%, 95%, 98% or 100% sequence identity hereto, b) from about 2 wt % to about 60 wt % of at least one surfactant, and optionally c) from about 5 wt % to about 50 wt % of at least one builder such as carbonates, zeolites, phosphate builder, calcium sequestering builders or complexing agents.

In some aspects of the invention liquid laundry compositions comprising:

a) at least 0.0001 ppm of active enzyme polypeptide, wherein the polypeptide comprises SEQ ID NO 36 or a polypeptide having at least 60%, e.g. 80%, 85%, 90%, 95%, 98% or 100% sequence identity hereto, b) from about 2 wt % to about 60 wt % of at least one surfactant, and optionally c) from about 5 wt % to about 50 wt % of at least one builder such as carbonates, zeolites, phosphate builder, calcium sequestering builders or complexing agents.

The composition may comprise from about 1 wt % to about 65 wt %, from about 5 wt % to about 50 wt %, preferably from about 40 wt % to 65 wt %, particularly about 20 wt % to about 65 wt %, particularly from 10 wt % to 50 wt % and wherein the builder. The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphonates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In the composition of the invention, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl)inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N, N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonic acid) (EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP)

The composition of the invention may also contain 0-50% by weight, such as about 5% to about 30%, of a detergent co-builder. The composition may include a co-builder alone, or in combination with a builder, for example a zeolite builder. Non-limiting examples of co-builders include homopolymers of polyacrylates or copolymers thereof, such as poly (acrylic acid) (PM) or copoly (acrylic acid/maleic acid) (PAA/PMA) or polyaspartic acid. Further exemplary builders and/or co-builders are described in, e.g., WO 09/102854, U.S. Pat. No. 5,977,053. In one preferred embodiment, the builder is a non-phosphorus based builder such as citric acid and/or methylglycine-N, N-diacetic acid (MGDA) and/or glutamic-N, N-diacetic acid (GLDA) and/or salts thereof.

Some aspect of the invention relates a composition comprising at least one enzyme, wherein the enzyme is a polypeptide comprising SEQ ID NO 20 or polypeptides having at least 60% sequence identity hereto, wherein the polypeptide has hexosaminidase activity and a non-phosphate builder selected from citric acid, methyl glycine-N, N-diacetic acid (MGDA) and/or glutamic-N, N-diacetic acid (GLDA) and mixtures thereof.

In some aspects, the composition is detergent composition, such as a laundry composition or an automatic dish wash composition (ADW) comprising:

a) at least 0.000.1 e.g. 0.01 ppm of active enzyme, wherein the enzyme is a polypeptide comprising SEQ ID NO 20 or polypeptides having at least 60% e.g. 80%, 85%, 90%, 95%, 98% or 100% sequence identity hereto, wherein the polypeptide has hexosaminidase activity, and b) 10-50 wt % builder selected from citric acid, methylglycine-N, N-diacetic acid (MGDA) and/or glutamic acid-N, N-diacetic acid (GLDA) and mixtures thereof, and optionally c) at least one bleach component.

In some aspects, the composition is detergent composition, such as a laundry composition or an automatic dish wash composition (ADW) comprising:

a) at least 0.0001 ppm of active enzyme, wherein the enzyme is a polypeptide comprising SEQ ID NO 20, SEQ ID NO 33, SEQ ID NO 34, SEQ ID NO 35, SEQ ID NO 36 or polypeptides having at least 60%, e.g. 80%, 85%, 90%, 95%, 98% or 100% sequence identity hereto, wherein the polypeptide has hexosaminidase activity, and b) 10-50 wt % builder selected from citric acid, methylglycine-N, N-diacetic acid (MGDA) and/or glutamic acid-N, N-diacetic acid (GLDA) and mixtures thereof, and optionally c) at least one bleach component.

In some aspects, the composition is detergent composition, such as a laundry composition or an automatic dish wash composition (ADW) comprising:

a) at least 0.0001 e.g. 0.01 ppm polypeptide, wherein the polypeptide comprises one or more Glyco_hydro_20 catalytic domains, wherein the Glyco_hydro_20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, preferably comprising one or more motifs selected from motif I: [IV]P[ED][LVI]DXP[AN]H (SEQ ID NO 21) and/or one or more motif II NYN[AS]Y[SY]LY (SEQ ID NO 22), and b) at least one bleach component.

In some aspects, the composition is detergent composition, such as a laundry composition or an automatic dish wash composition (ADW) comprising:

a) at least 0.01 ppm of active enzyme polypeptide, wherein the polypeptide comprises SEQ ID NO 20 or a polypeptide having at least 60% e.g. 80%, 85%, 90%, 95%, 98% or 100% sequence identity hereto, and b) at least one bleach component.

In some aspects, the composition is detergent composition, such as a laundry composition or an automatic dish wash composition (ADW) comprising:

a) at least 0.0001 ppm of active enzyme polypeptide, wherein the polypeptide comprises SEQ ID NO 20 or a polypeptide having at least 60% e.g. 80%, 85%, 90%, 95%, 98% or 100% sequence identity hereto, and b) at least one bleach component.

In some aspects, the composition is detergent composition, such as a laundry composition or an automatic dish wash composition (ADW) comprising:

a) at least 0.0001 ppm of active enzyme polypeptide, wherein the polypeptide comprises SEQ ID NO 33 or a polypeptide having at least 60% sequence identity hereto, and b) at least one bleach component.

In some aspects, the composition is detergent composition, such as a laundry composition or an automatic dish wash composition (ADW) comprising:

a) at least 0.0001 ppm of active enzyme polypeptide, wherein the polypeptide comprises SEQ ID NO 34 or a polypeptide having at least 60% e.g. 80%, 85%, 90%, 95%, 98% or 100% sequence identity hereto, and b) at least one bleach component.

In some aspects, the composition is detergent composition, such as a laundry composition or an automatic dish wash composition (ADW) comprising:

a) at least 0.0001 ppm of active enzyme polypeptide, wherein the polypeptide comprises SEQ ID NO 35 or a polypeptide having at least 60% e.g. 80%, 85%, 90%, 95%, 98% or 100% sequence identity hereto, and b) at least one bleach component.

In some aspects, the composition is detergent composition, such as a laundry composition or an automatic dish wash composition (ADW) comprising:

a) at least 0.0001 ppm of active enzyme polypeptide, wherein the polypeptide comprises SEQ ID NO 36 or a polypeptide having at least 60% e.g. 80%, 85%, 90%, 95%, 98% or 100% sequence identity hereto, and b) at least one bleach component.

The composition may contain from about 1 wt % to about 40 wt %, preferably from about 0.5 wt % to about 30 wt %, preferably from about 0.1 wt % to about 10 wt % 0-30% by weight, such as about 1% to about 20%, such as about 1% to about 10%, such as about 1% to about 5%, such as about 10% to about 30%, such as about 5% to about 10% or such as about 10% to about 20% by weight (wt %) of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide Suitable sources of hydrogen peroxide are inorganic persalts, including alkali metal salts such as sodium percarbonate and sodium perborates (usually mono- or tetrahydrate), and hydrogen peroxide-urea (1/1).

Sources of peracids Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl) oxy] benzene-1-sulfonate (ISONOBS), sodium 4-(dodecanoyloxy) benzene-1-sulfonate (LOBS), sodium 4-(decanoyloxy) benzene-1-sulfonate, 4-(decanoyloxy) benzoic acid (DOBA), sodium 4-(nonanoyloxy) benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2''-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

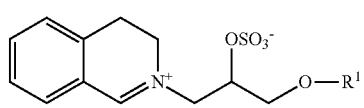

(i)

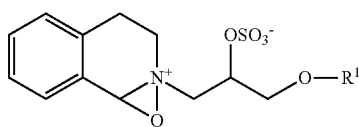

(ii)

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

The present invention relates to polypeptides comprising a Glyco_hydro_20 catalytic domain and having hexosaminidase activity, compositions e.g. detergent compositions comprising the polypeptides, and the use of detergent composition comprising the polypeptides of the invention for deep cleaning of an item such as a textile.

Accordingly, some aspects of the invention relate to detergent compositions comprising:
  a) at least 0.001 e.g. 0.01 ppm of active enzyme polypeptide, wherein the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, preferably comprising one or more motifs selected from motif I: [IV]P[ED][LVI]DXP[AN]H (SEQ ID NO 21) and/or one or more motif II NYN[AS]Y[SY]LY (SEQ ID NO 22), and optionally
  b) from about 10 wt % to about 50 wt % builder preferably selected from citric acid, methylglycine-N, N-diacetic acid (MGDA) and/or glutamic acid-N, N-diacetic acid (GLDA) and mixtures thereof, and optionally
  c) from about 5 wt % to about 50 wt % surfactant, preferably selected from anionic surfactants such as LAS, AOS, AEOS and/or nonionic surfactants such as AE or AEO, and optionally
  d) at least one bleach component, preferably selected from percarbonates, persulphates and peracids.

Accordingly, some aspects of the invention relate to detergent compositions comprising:
  a) at least 0.0001 ppm e.g. 0.01 ppm of active enzyme polypeptide, wherein the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, preferably comprising one or more motifs selected from motif I: [IV]P[ED][LVI]DXP[AN]H (SEQ ID NO 21) and/or one or more motif II NYN[AS]Y[SY]LY (SEQ ID NO 22), and optionally
  b) from about 10 wt % to about 50 wt % builder preferably selected from citric acid, methylglycine-N, N-diacetic acid (MGDA) and/or glutamic acid-N, N-diacetic acid (GLDA) and mixtures thereof, and optionally
  c) from about 5 wt % to about 50 wt % surfactant, preferably selected from anionic surfactants such as LAS, AOS, AEOS and/or nonionic surfactants such as AE or AEO, and optionally
  d) at least one bleach component, wherein the bleach is a peroxide and the bleach catalyst is a manganese compound, wherein, the oxygen bleach is preferably percarbonate and the manganese catalyst preferably 1,4,7-trimethyl-1,4,7-triazacyclononane or manganese (III) acetate tetrahydrate (MnTACN).

In a preferred aspect, the polypeptide comprises the amino acids sequence with SEQ ID NO 20 or an amino acid sequence having at least 60%, such as at least 70%, such as at least 80%, such as at least 90%, such as at least 95% sequence identity to SEQ ID NO 20.

In a preferred aspect the polypeptide comprises the amino acids sequence with SEQ ID NO 20 or an amino acid sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to SEQ ID NO 20.

In a preferred aspect the polypeptide comprises the amino acids sequence with SEQ ID NO 33 or an amino acid sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to SEQ ID NO 33.

In a preferred aspect the polypeptide comprises the amino acids sequence with SEQ ID NO 34 or an amino acid sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to SEQ ID NO 34.

In a preferred aspect the polypeptide comprises the amino acids sequence with SEQ ID NO 35 or an amino acid sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to SEQ ID NO 35.

In a preferred aspect the polypeptide comprises the amino acids sequence with SEQ ID NO 36 or an amino acid sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to SEQ ID NO 36.

The polypeptides and composition comprising the polypeptides of the invention having hexosaminidase activity, preferably N-acetylglucosaminidase activity and/or β-N-acetylglucosamininidase activity may be used for reducing and/or removing components of biofilm e.g. EPS and/or PNAG on items such as hard surfaces, textiles and/or fabric. Organic matter such as biofilm can develop on surfaces such as textiles when microorganisms are present on the item. The organic matter maybe sticky and soils may stick to the organic matter, which may be difficult to remove. One aspect of the invention relates to the use of a composition as described above for deep-cleaning of an item, wherein the item is a textile.

One aspect of the invention relates to the use of a polypeptide, having hexosaminidase activity, preferably N-acetylglucosaminidase activity and/or β-N-acetylglucosamininidase activity, wherein the polypeptide comprises one or more Glyco_hydro_20 catalytic domains, wherein the polypeptide comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41).

One aspect of the invention relates to the use of a polypeptide, having hexosaminidase activity, preferably N-acetylglucosaminidase activity and/or β-N-acetylglucosamininidase activity, wherein the polypeptide comprises one or more Glyco_hydro_20 catalytic domains, wherein the polypeptide comprises one or more of the motif(s) ARAYYPV (SEQ ID NO 42), AWNDGID (SEQ ID NO 43) or DDQNVGI (SEQ ID NO 44) or DPRIH (SEQ ID NO 45).

One aspect relates to the use of a polypeptide, having hexosaminidase activity, preferably N-acetylglucosaminidase activity and/or β-N-acetylglucosamininidase activity, wherein the polypeptide comprises one or more Glyco_hydro_20 catalytic domains, wherein the polypeptide comprises one or more of the motif(s) [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) or DPRIH (SEQ ID NO 45), (i) for preventing, reducing or removing stickiness of the item;

(ii) for pretreating stains on the item;

(iii) for preventing, reducing or removing redeposition of soil during a wash cycle;

(iv) for preventing, reducing or removing adherence of soil to the item;

(v) for maintaining or improving whiteness of the item;

(vi) for preventing, reducing or removal malodor from the item, wherein the item is a textile.

The polypeptide preferably has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 20, SEQ ID NO 33, SEQ ID NO 34, SEQ ID NO 35 or SEQ ID NO 36.

The present invention concerns the use of a polypeptides comprising the Glyco_hydro_20 catalytic domain and having hexosaminidase activity for deep cleaning of an item, wherein the polypeptide is a polypeptide having at least 60% e.g. 80%, 85%, 90%, 95%, 98% or 100% sequence identity to the polypeptide comprising SEQ ID NO 20, SEQ ID NO 33, SEQ ID NO 34, SEQ ID NO 35 or SEQ ID NO 36 and wherein the item is a textile. In one aspect of the invention the polypeptide comprising the Glyco_hydro_20 catalytic domain having hexosaminidase activity is used for preventing, reducing or removing the stickiness of an item, wherein the polypeptide is a polypeptide having at least 60% e.g. 80%, 85%, 90%, 95%, 98% or 100% sequence identity to the polypeptide comprising SEQ ID NO 20, SEQ ID NO 33, SEQ ID NO 34, SEQ ID NO 35 or SEQ ID NO 36. The polypeptide comprising the Glyco_hydro_20 catalytic domain having hexosaminidase activity can further be used for pre-treating stains on textile such as textile.

Additionally, the invention relates to the use of a polypeptide Glyco_hydro_20 catalytic domain having hexosaminidase activity e.g. a polypeptide having at least 60% e.g. 80%, 85%, 90%, 95%, 98% or 100% sequence identity to the polypeptide comprising SEQ ID NO 20, SEQ ID NO 33, SEQ ID NO 34, SEQ ID NO 35 or SEQ ID NO 36 for preventing, reducing or removing re-deposition of soil during a wash cycle. When the polypeptide is used for example in the laundering of textile, the polypeptide hinders deposition of soil present in the wash liquor to deposit on the textile.

Further, the invention concerns the use of a polypeptide Glyco_hydro_20 catalytic domain having hexosaminidase activity e.g. a polypeptide having at least 60% e.g. 80%, 85%, 90%, 95%, 98% or 100% sequence identity to the polypeptide comprising SEQ ID NO 20, SEQ ID NO 33, SEQ ID NO 34, SEQ ID NO 35 or SEQ ID NO 36 for preventing, reducing or removing the adherence of soil to an item. In one embodiment, the item is textile. When the soil does not adhere to the item, the item appears cleaner. Thus, the invention further concerns the use of a polypeptide comprising a Glyco_hydro_20 catalytic domain e.g. a polypeptide having at least 60% e.g. 80%, 85%, 90%, 95%, 98% or 100% sequence identity to the polypeptide comprising SEQ ID NO 20, SEQ ID NO 33, SEQ ID NO 34, SEQ ID NO 35 or SEQ ID NO 36 having hexosaminidase activity for maintaining or improving the whiteness of the item.

When items like T-shirts or sportswear are used, they are exposed to bacteria from the body of the user and from the rest of the environment in which they are used, such bacteria may form organic matter such as EPS (extracellular polymeric substances), which comprises PNAG. The organic matter may cause malodor on the item even after the item is washed. The polypeptides of the invention have hexosaminidase activity e.g. PNAG activity and are thus effective in preventing, reducing or removing organic components such as PNAG and the EPS comprising PNAG. The present invention therefore also concerns removal or reduction of malodor on textile. The malodor can be present on newly washed textile which is still wet. Or the malodor can be present on newly washed textile, which has subsequently been dried. The malodor may also be present on textile, which has been stored for some time after wash. The present invention relates to reduction or removal of malodor such as E-2-nonenal from wet or dry textile.

The cleaning composition according to the invention may comprise a cleaning ingredient or a detergent adjunct; the detergent adjunct ingredient may be surfactants and builders and/or chelators such as those described above. The adjunct ingredients may also be any of the following flocculating aid, dye transfer inhibitors, enzymes, enzyme stabilizers, enzyme inhibitors, catalytic materials, bleach activators, hydrogen peroxide, sources of hydrogen peroxide, pre-formed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

In one embodiment, the detergent adjunct ingredient is a builder or a clay soil removal/anti-redeposition agent.

In one embodiment, detergent adjunct ingredient is an enzyme. The one or more enzymes may be selected from the group consisting of proteases, lipases, cutinases, amylases, carbohydrases, cellulases, pectinases, mannanases, arabinases, galactanases, xylanases and oxidases.

In addition to the polypeptides having hexosaminidase activity comprising SEQ ID NO 20, SEQ ID NO 33, SEQ ID NO 34, SEQ ID NO 35, SEQ ID NO 36 or polypeptide having at least 60% sequence identity hereto the cleaning composition of the invention may further comprise cellulases. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase polypeptides such as those described in WO 94/07998, EP 0 531 315, U.S. Pat. Nos. 5,457,046, 5,686,593, 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially polypeptides thereof having substitution, insertion and/or deletion at one or more of the positions corresponding to the following positions in SEQ ID NO 8 of WO 02/099091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme™, Celluclean and Carezyme™ (Novozymes A/S), Clazinase™, and Puradax HA™ (Genencor International Inc.), and KAC-500(B)™ (Kao Corporation).

In addition to the polypeptides having hexosaminidase activity comprising SEQ ID NO 20, SEQ ID NO 33, SEQ ID NO 34, SEQ ID NO 35, SEQ ID NO 36 or polypeptide having at least 60% sequence identity hereto the cleaning composition of the invention may further comprise proteases. Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, compared to SEQ ID NO 1 of WO 2016/001449, wherein the positions correspond to the positions of the *Bacillus Lentus* protease shown in SEQ ID NO 1 of WO 2016/001449. More preferred the subtilase variants may comprise one or more of the mutations: S3T, V41, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V1991, Y203W, S206G, L211Q, L211D, N212D, N212S, M216S, A226V, K229L, Q230H, Q239R, N246K, N255W, N255D, N255E, L256E, L256D T268A or R269H. The protease variants are preferably variants of the *Bacillus Lentus* protease (Savinase®) shown in SEQ ID NO 1 of WO 2016/001449, the *Bacillus* amylolichenifaciens protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO 1 of WO2004/067737, wherein the protease variant has a sequence identity of at least 75% but less than 100% to SEQ ID NO 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes NS), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™ Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

In addition to the polypeptides having hexosaminidase activity comprising SEQ ID NO 20, SEQ ID NO 33, SEQ ID NO 34, SEQ ID NO 35, SEQ ID NO 36 or polypeptide having at least 60% sequence identity hereto the cleaning composition of the invention may further comprise lipases and cutinases which include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147). Other examples are lipase polypeptides such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500. Preferred commercial lipase products include include Lipolase™, Lipex™; Lipolex™ and Lipoclean™ (Novozymes A/S), Lumafast (originally from Genencor) and Lipomax (originally from Gist-Brocades). Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and polypeptides of the *M. smegmatis* perhydrolase in particular the S54V variant used in the commercial product Gentle Power Bleach from Huntsman Textile Effects Pte Ltd (WO10/100028).

In addition to the polypeptides having hexosaminidase activity comprising SEQ ID NO 20, SEQ ID NO 33, SEQ ID NO 34, SEQ ID NO 35, SEQ ID NO 36 or polypeptide having at least 60% sequence identity hereto the cleaning composition of the invention may further comprise amylases which can be used together with a polypeptide of the invention. The amylase may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839. Suitable amylases include amylases having SEQ ID NO 3 in WO 95/10603 or polypeptides having 90% sequence identity to SEQ ID NO 3 thereof. Preferred polypeptides are described in WO 94/02597, WO 94/18314, WO 97/43424 and SEQ ID NO 4 of WO 99/019467, such as polypeptides with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO 6 in WO 02/010355 or polypeptides thereof having 90% sequence identity to SEQ ID NO 6. Preferred polypeptides of SEQ ID NO 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO 6 of WO 2006/066594 and residues 36-483 of the *B. licheniformis* alpha-amylase shown in SEQ ID NO 4 of WO 2006/066594 or polypeptides having 90% sequence identity thereof. Preferred polypeptides of this hybrid alpha-amylase are those having a substitution, a deletion or an insertion in one of more of the following positions: G48, T49, G107, H156, A181, N190, M197, I201, A209 and Q264. Most preferred polypeptides of the hybrid alpha-amylase comprising residues 1-33 of the alpha-amylase derived from *B. amyloliquefaciens* shown in SEQ ID NO 6 of WO 2006/066594 and residues 36-483 of SEQ ID NO 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO 6 in WO 99/019467 or polypeptides thereof having 90% sequence identity to SEQ ID NO 6. Preferred polypeptides of SEQ ID NO 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO 1, SEQ ID NO 3, SEQ ID NO 2 or SEQ ID NO 7 of WO 96/023873 or polypeptides thereof having 90% sequence identity to SEQ ID NO 1, SEQ ID NO 2, SEQ ID NO 3 or SEQ ID NO 7. Preferred polypeptides of SEQ ID NO 1, SEQ ID NO 2, SEQ ID NO 3 or SEQ ID NO 7 are those having a substitution, a deletion or an insertion in one or more of the following positions: 140, 181, 182, 183, 184, 195, 206, 212, 243, 260, 269, 304 and 476. More preferred polypeptides are those having a deletion in positions 181 and 182 or positions 183 and 184. Most preferred amylase polypeptides of SEQ ID NO 1, SEQ ID NO 2 or SEQ ID NO 7 are those having a deletion in positions 183 and 184 and a substitution in one or more of positions 140, 195, 206, 243, 260, 304 and 476. Other amylases which can be used are amylases having SEQ ID NO 2 of WO 08/153815, SEQ ID NO 10 in WO 01/66712 or polypeptides thereof having 90% sequence identity to SEQ ID NO 2 of WO 08/153815 or 90% sequence identity to SEQ ID NO 10 in WO 01/66712. Preferred polypeptides of SEQ ID NO 10 in WO 01/66712 are those having a substitution, a deletion or an insertion in one of more of the following positions: 176, 177, 178, 179, 190, 201, 207, 211 and 264. Further suitable amylases are amylases having SEQ ID NO 2 of WO 09/061380 or polypeptides having 90% sequence identity to SEQ ID NO 2 thereof. Preferred polypeptides of SEQ ID NO 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred polypeptides of SEQ ID NO 2 are those having the substitution in one of more of the following positions: Q87E,R, Q98R, S125A, N128C, T131I, T165I, K178L, T182G, M201L, F202Y, N225E,R, N272E,R, S243Q,A,E, D, Y305R, R309A, Q320R, Q359E, K444E and G475K and/or deletion in position R180 and/or S181 or of T182 and/or G183. Most preferred amylase polypeptides of SEQ ID NO 2 are those having the substitutions:
N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+ Y305R+G475K wherein the polypeptides are C-terminally truncated and optionally further comprises a substitution at position 243 and/or a deletion at position 180 and/or position 181.

Other suitable amylases are the alpha-amylase having SEQ ID NO 12 in WO01/66712 or a variant having at least 90% sequence identity to SEQ ID NO 12. Preferred amylase polypeptides are those having a substitution, a deletion or an insertion in one of more of the following positions of SEQ ID NO 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include polypeptides having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase polypeptides such as those described in WO2011/098531, WO2013/001078 and WO2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

In addition to the polypeptides having hexosaminidase activity comprising SEQ ID NO 20, SEQ ID NO 33, SEQ ID NO 34, SEQ ID NO 35, SEQ ID NO 36 or a polypeptide having at least 60% sequence identity hereto the cleaning composition of the invention may further comprise peroxidases/oxidases including those of plant, bacterial or fungal origin. Chemically modified or protein engineered mutants are included. Examples of useful peroxidases include peroxidases from Coprinus, e.g., from C. cinereus, and polypeptides thereof as those described in WO 93/24618, WO 95/10602, and WO 98/15257. Commercially available peroxidases include Guardzyme™ (Novozymes A/S).

The cleaning compositions of the invention may also contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide anti-redeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), (carboxymethyl) inulin (CMI), and polycarboxylates such as PAA, PAA/ PMA, polyaspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The cleaning compositions of the present invention may also include fabric hueing agents such as dyes or pigments, which when formulated in detergent compositions can deposit onto a fabric when the fabric is contacted with a wash liquor comprising the cleaning e.g. detergent compositions and thus altering the tint of the fabric through absorption/reflection of visible light. Fluorescent whitening agents emit at least some visible light if subjected to ultraviolet light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The cleaning compositions of the present invention may also include one or more dye transfer inhibiting agents. Suitable polymeric dye transfer inhibiting agents include, but are not limited to, polyvinylpyrrolidone polymers, polyamine-N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the laundry composition of the present invention. The most commonly used fluorescent whitening agents are those belonging to the classes of diaminostilbene-sulfonic acid derivatives, diarylpyrazoline derivatives and biphenyl-distyryl derivatives. Examples of the diaminostilbene-sulfonic acid derivative type of fluorescent whitening agents include the sodium salts of: 4,4'-bis[(4-anilino-6-diethanolamino-s-triazin-2-yl)amino]stilbene-2,2'-disulfonate, 4,4'-bis[(4,6-dianilino-s-triazin-2-yl)amino]stilbene-2,2'-disulfonate, 4,4'-bis{4-anilino-6-[methyl(2-hydroxyethyl)amino]-s-triazin-2-ylamino} stilbene-2,2'-disulfonate, 4,4'-bis(4-phenyl-1,2,3-triazol-2-yl) stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from BASF. Tinopal DMS is the disodium salt of 4,4'-bis[(4-anilino-6-morpholino-s-triazin-2-yl) amino] stilbene-2,2'-disulfonate. Tinopal CBS is the disodium salt of 2,2'-[biphenyls-4,4'-di(2,1-ethenediyl)]dibenzene-1-sulfonate. Also preferred is the commercially available Parawhite KX, supplied by Paramount Minerals and Chemicals, Mumbai, India. Other fluorescers suitable for use in the invention include the 1-3-diarylpyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The cleaning compositions of the present invention may also include one or more soil-release polymers which aid the removal of soils from fabrics such as cotton and polyester-based fabrics, in particular the removal of hydrophobic soils from polyester-based fabrics. The soil release polymers may for example be nonionic or anionic terephthalate-based polymers, polyvinylcaprolactam and related copolymers, vinyl graft copolymers or polyester polyamides; see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil-release polymers. Suitable graft co-polymers are described in more detail in WO 2007/138054, WO 2006/108856 and WO 2006/113314 (hereby incorporated by reference). Other soil-release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof.

The cleaning compositions of the present invention may also include one or more anti-redeposition agents such as (carboxymethyl) cellulose (CMC), poly (vinyl alcohol) (PVA), homopolymers of acrylic acid, copolymers of acrylic acid and maleic acid, and ethoxylated polyethyleneimines. The cellulose based polymers described under soil-release polymers above may also function as anti-redeposition agents.

The cleaning composition of the invention may also contain one are more adjunct material. Suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably, the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US2009/0011970 A1.

Cleaning and detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

The present invention is also directed to methods for using the polypeptides according to the invention or compositions thereof in laundering of textile and fabrics, such as house hold laundry washing and industrial laundry washing.

The invention is also directed to methods for using the polypeptides according to the invention or compositions thereof in cleaning hard surfaces such as floors, tables, walls, roofs etc. as well as surfaces of hard objects such as cars (car wash) and dishes (dish wash).

The polypeptides of the present invention may be added to and thus become a component of a detergent composition. Thus, one aspect of the invention relates to the use of a polypeptide having hexosaminidase activity comprising SEQ ID NO 20, SEQ ID NO 33, SEQ ID NO 34, SEQ ID NO 35, SEQ ID NO 36 or a polypeptide having at least 60% sequence identity hereto and having hexosaminidase activity in a cleaning process such as laundering and/or hard surface cleaning.

Thus, one aspect of the invention relates to the use of the use of a polypeptide having hexosaminidase activity comprising SEQ ID NO 20, SEQ ID NO 33, SEQ ID NO 34, SEQ ID NO 35, SEQ ID NO 36 or a polypeptide having at least 60% sequence identity hereto and having hexosaminidase activity in a cleaning process such as laundering and/or hard surface cleaning and wherein the polypeptide has improved wash performance, relative to a reference enzyme.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease variant of the invention. The cleaning process or a textile care process can for example be carried out in a machine washing process or in a manual washing process. The washing solution can for example be an aqueous washing solution containing a detergent composition.

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases are needed to achieve a similar or improved wash performance when compared to the traditional detergent compositions.

The polypeptides comprising the Glyco_hydro_20 catalytic domain are thus particularly useful in composition, such as detergent compositions, comprising cleaning ingredients and the polypeptides of the invention may preferably be used in cleaning processes such as laundry and dish wash.

Novel Hexosaminidases of the Invention

The invention relates to a polypeptide having hexosaminidase activity, wherein the polypeptide comprises one or more Glyco_hydro_20 catalytic domains and optionally one or more domain(s) [IV]P[ED][LVI]DXP[AN]H (SEQ ID NO 21), NYN[AS]Y[SY]LY (SEQ ID NO 22), GXDE (SEQ ID NO 41). One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprises an amino acid sequences selected from the sequences shown in SEQ ID NO 5, SEQ ID NO 6, SEQ ID NO 7, SEQ ID NO 8, SEQ ID NO 37, SEQ ID NO 38 and SEQ ID NO 39 or polypeptides having at least 60% e.g. 80%, 85%, 90%, 95%, 98% or 100% sequence identity hereto.

One aspect relates to a polypeptide having hexosaminidase activity, selected from the group consisting of:
  (a) a polypeptide having at least 80% sequence identity to the polypeptide of SEQ ID NO 20;
  (b) a polypeptide having at least 80% sequence identity to the polypeptide of SEQ ID NO 33;
  (c) a polypeptide having at least 80% sequence identity to the polypeptide of SEQ ID NO 34;
  (d) a polypeptide having at least 80% sequence identity to the polypeptide of SEQ ID NO 35;
  (e) a variant of the polypeptide selected from the group consisting of SEQ ID NO 20, SEQ ID NO 33, SEQ ID NO 34 or SEQ ID NO 35, wherein the variant has hexosaminidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
  (f) a polypeptide comprising the polypeptide of (a) to (e) and a N-terminal and/or C-terminal His-tag and/or HQ-tag;
  (g) a polypeptide comprising the polypeptide of (a) to (e) and a N-terminal and/or C-terminal extension of between 1 and 10 amino acids;
  (h) a fragment of the polypeptide of (a) to (e) having hexosaminidase activity and having at least 90% of the length of the mature polypeptide;
  (i) a polypeptide comprising one or more of the motifs [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) or DPRIH (SEQ ID NO 45); and
  (j) polypeptide having N-acetylglucosaminidase activity and/or β-N-acetylglucosamininidase activity.

The polypeptide preferably has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 20, SEQ ID NO 33, SEQ ID NO 34 or SEQ ID NO 35.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 5 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 5.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 6 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 6.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 7 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 7.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 8 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 8.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 37 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 37.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 38 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 38.

One aspect relates to a polypeptide having hexosaminidase activity, wherein the polypeptide optionally comprises one or more domain(s) [IV]P[ED][LVI]DXP[AN]H (SEQ ID NO 21), NYN[AS]Y[SY]LY (SEQ ID NO 22), GXDE (SEQ ID NO 41) and wherein the polypeptide comprise the amino acid sequence shown in SEQ ID NO 39 or comprise an amino acids sequence having at least 60%, such as at least 70%, such as at least 75%, such as at least 80%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence shown in SEQ ID NO 39.

In some aspects of the invention the polypeptides of the invention e.g. the polypeptides having at least at least 60%, such as at least 70%, such as at least 80% or such as at least 90% sequence identity the mature polypeptides of SEQ ID NO 12 or to the mature polypeptide with SEQ ID NO 20 have β-N-acetylglucosamininidase activity and in some aspect, the hexosaminidase activity is β-N-acetylglucosamininidase activity and the polypeptide of the invention are β-N-acetylglucosamininidases.

In some aspects of the invention the polypeptides of the invention e.g. the polypeptides having at least at least 60%, such as at least 70%, such as at least 80% or such as at least 90% sequence identity the mature polypeptides of SEQ ID NO 25 or to the mature polypeptide with SEQ ID NO 33 have β-N-acetylglucosamininidase activity and in some aspect, the hexosaminidase activity is β-N-acetylglucosamininidase activity and the polypeptide of the invention are β-N-acetylglucosamininidases.

In some aspects of the invention the polypeptides of the invention e.g. the polypeptides having at least at least 60%, such as at least 70%, such as at least 80% or such as at least 90% sequence identity the mature polypeptides of SEQ ID NO 26 or to the mature polypeptide with SEQ ID NO 34 have β-N-acetylglucosamininidase activity and in some aspect, the hexosaminidase activity is β-N-acetylglucosamininidase activity and the polypeptide of the invention are β-N-acetylglucosamininidases.

In some aspects of the invention the polypeptides of the invention e.g. the polypeptides having at least at least 60%, such as at least 70%, such as at least 80% or such as at least 90% sequence identity the mature polypeptides of SEQ ID NO 27 or to the mature polypeptide with SEQ ID NO 35 have β-N-acetylglucosamininidase activity and in some aspect, the hexosaminidase activity is β-N-acetylglucosamininidase activity and the polypeptide of the invention are β-N-acetylglucosamininidases.

In some aspects of the invention the polypeptides of the invention e.g. the polypeptides having at least at least 60%, such as at least 70%, such as at least 80% or such as at least 90% sequence identity the mature polypeptides of SEQ ID NO 28 or to the mature polypeptide with SEQ ID NO 36 have β-N-acetylglucosamininidase activity and in some aspect, the hexosaminidase activity is β-N-acetylglucosamininidase activity and the polypeptide of the invention are β-N-acetylglucosamininidases.

The invention further relates to a polypeptide, optionally comprising one or more domain(s) selected from the group consisting of [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) and DPRIH (SEQ ID NO 45), wherein the polypeptide has a sequence identity to the mature polypeptide shown in SEQ ID NO 20 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which has hexosaminidase activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO 20. In an embodiment, the polypeptide has been isolated. In an embodiment, the polypeptide has at least at least 70%, e.g. at least 80%, at least 90%, at least 95% or at least 100% of the hexosaminidase activity of the mature polypeptide of SEQ ID NO 20.

The invention further relates to a polypeptide, optionally comprising one or more domain(s) selected from the group consisting of [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) and DPRIH (SEQ ID NO 45), wherein the polypeptide has a sequence identity to the mature polypeptide shown in SEQ ID NO 33 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which has hexosaminidase activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO 33. In an embodiment, the polypeptide has been isolated. In an embodiment, the polypeptide has at least at least 70%, e.g. at least 80%, at least 90%, at least 95% or at least 100% of the hexosaminidase activity of the mature polypeptide of SEQ ID NO 33.

The invention further relates to a polypeptide, optionally comprising one or more domain(s) selected from the group consisting of [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) and DPRIH (SEQ ID NO 45), wherein the polypeptide has a sequence identity to the mature polypeptide shown in SEQ ID NO 34 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which has hexosaminidase activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO 34. In an embodiment, the polypeptide has been isolated. In an embodiment, the polypeptide has at least at least 70%, e.g. at least 80%, at least 90%, at least 95% or at least 100% of the hexosaminidase activity of the mature polypeptide of SEQ ID NO 34.

The invention further relates to a polypeptide, optionally comprising one or more domain(s) selected from the group consisting of [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) and DPRIH (SEQ ID NO 45), wherein the polypeptide has a sequence identity to the mature polypeptide shown in SEQ ID NO 35 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which has hexosaminidase activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO 35. In an embodiment, the polypeptide has been isolated. In an embodiment, the polypeptide has at least at least 70%, e.g. at least 80%, at least 90%, at least 95% or at least 100% of the hexosaminidase activity of the mature polypeptide of SEQ ID NO 35.

The invention further relates to a polypeptide, optionally comprising one or more domain(s) selected from the group consisting of [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) and DPRIH (SEQ ID NO 45), wherein the polypeptide has a sequence identity to the mature polypeptide shown in SEQ ID NO 36 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% and which has hexosaminidase activity. In one aspect, the polypeptides differ by up to 49 amino acids, e.g., between 1 and 49 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 amino acids from the mature polypeptide of SEQ ID NO 36. In an embodiment, the polypeptide has been isolated. In an embodiment, the polypeptide has at least at least 70%, e.g. at least 80%, at least 90%, at least 95% or at least 100% of the hexosaminidase activity of the mature polypeptide of SEQ ID NO 36.

A polypeptide of the present invention preferably comprises or consists of the amino acid sequence of SEQ ID NO 20 or an allelic variant thereof; comprises or consists of the amino acid sequence of SEQ ID NO 20 and a N-terminal and/or C-terminal His-tag and/or HQ-tag; or is a fragment thereof having hexosaminidase activity wherein the fragment comprises at least 300 amino acids, such as at least 320 amino acids, at least 350 amino acids, at least 400 amino acids, at least 410 amino acids, at least 420 amino acids, at least 430 amino acids, at least 440 amino acids, at least 450 amino acids or at least 460 amino acids.

A polypeptide of the present invention preferably comprises or consists of the amino acid sequence of SEQ ID NO 33 or an allelic variant thereof; comprises or consists of the amino acid sequence of SEQ ID NO 33 and a N-terminal and/or C-terminal His-tag and/or HQ-tag; or is a fragment thereof having hexosaminidase activity wherein the fragment comprises at least 300 amino acids, such as at least 320 amino acids, at least 350 amino acids, at least 400 amino acids, at least 410 amino acids, at least 420 amino acids, at least 430 amino acids, at least 440 amino acids, at least 450 amino acids or at least 460 amino acids.

A polypeptide of the present invention preferably comprises or consists of the amino acid sequence of SEQ ID NO 34 or an allelic variant thereof; comprises or consists of the amino acid sequence of SEQ ID NO 34 and a N-terminal and/or C-terminal His-tag and/or HQ-tag; or is a fragment thereof having hexosaminidase activity wherein the fragment comprises at least 300 amino acids, such as at least 320 amino acids, at least 350 amino acids, at least 400 amino acids, at least 410 amino acids, at least 420 amino acids, at least 430 amino acids, at least 440 amino acids, at least 450 amino acids or at least 460 amino acids.

A polypeptide of the present invention preferably comprises or consists of the amino acid sequence of SEQ ID NO 35 or an allelic variant thereof; comprises or consists of the amino acid sequence of SEQ ID NO 35 and a N-terminal and/or C-terminal His-tag and/or HQ-tag; or is a fragment thereof having hexosaminidase activity wherein the fragment comprises at least 300 amino acids, such as at least 320 amino acids, at least 350 amino acids, at least 400 amino acids, at least 410 amino acids, at least 420 amino acids, at least 430 amino acids, at least 440 amino acids, at least 450 amino acids or at least 460 amino acids.

A polypeptide of the present invention preferably comprises or consists of the amino acid sequence of SEQ ID NO 36 or an allelic variant thereof; comprises or consists of the amino acid sequence of SEQ ID NO 36 and a N-terminal and/or C-terminal His-tag and/or HQ-tag; or is a fragment thereof having hexosaminidase activity wherein the fragment comprises at least 300 amino acids, such as at least 320 amino acids, at least 350 amino acids, at least 400 amino acids, at least 410 amino acids, at least 420 amino acids, at least 430 amino acids, at least 440 amino acids, at least 450 amino acids or at least 460 amino acids.

In another aspect, the present invention relates to a polypeptide having hexosaminidase activity encoded by a polynucleotide that hybridizes under medium-high stringency conditions, high stringency conditions, or very high stringency conditions with (i) the mature polypeptide coding sequence of SEQ ID NO 16, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 16 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another aspect, the present invention relates to a polypeptide having hexosaminidase activity encoded by a polynucleotide that hybridizes under medium-high stringency conditions, high stringency conditions, or very high stringency conditions with (i) the mature polypeptide coding sequence of SEQ ID NO 29, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 29 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another aspect, the present invention relates to a polypeptide having hexosaminidase activity encoded by a polynucleotide that hybridizes under medium-high stringency conditions, high stringency conditions, or very high stringency conditions with (i) the mature polypeptide coding sequence of SEQ ID NO 30, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 30 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another aspect, the present invention relates to a polypeptide having hexosaminidase activity encoded by a polynucleotide that hybridizes under medium-high stringency conditions, high stringency conditions, or very high stringency conditions with (i) the mature polypeptide coding sequence of SEQ ID NO 31, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 31 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another aspect, the present invention relates to a polypeptide having hexosaminidase activity encoded by a polynucleotide that hybridizes under medium-high stringency conditions, high stringency conditions, or very high stringency conditions with (i) the mature polypeptide coding sequence of SEQ ID NO 32, (ii) the cDNA sequence thereof; or (iii) the full-length complement of (i) or (ii) (Sambrook et al., 1989, *Molecular Cloning, A Laboratory Manual,* 2d edition, Cold Spring Harbor, New York). In an embodiment, the polypeptide has been isolated.

The polynucleotide of SEQ ID NO 16, SEQ ID NO 29, SEQ ID NO 30, SEQ ID NO 31, SEQ ID NO 32 or a subsequence thereof, as well as the mature polypeptide of SEQ ID NO 20, SEQ ID NO 33, SEQ ID NO 34, SEQ ID NO 35, SEQ ID NO 36 or a fragment thereof may be used to design nucleic acid probes to identify and clone DNA encoding polypeptides having hexosaminidase activity from strains of different genera or species according to methods well known in the art. Such probes can be used for hybridization with the genomic DNA or cDNA of a cell of interest, following standard Southern blotting procedures, to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having hexosaminidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. To identify a clone or DNA that hybridizes with SEQ ID NO 16, 29, 30, 31 or 32 or a subsequence thereof, the carrier material is used in a Southern blot.

For purposes of the present invention, hybridization indicates that the polynucleotide hybridizes to a labeled nucleic acid probe corresponding to (i) SEQ ID NO 16, SEQ ID NO 29, SEQ ID NO 30, SEQ ID NO 31, SEQ ID NO 32; (ii) the mature polypeptide coding sequence of SEQ ID NO 20, SEQ ID NO 33, SEQ ID NO 34, SEQ ID NO 35, SEQ ID NO 36; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

The present invention relates to polynucleotides encoding a polypeptide or a catalytic domain of the present invention, as described herein. In an embodiment, the polynucleotide encoding the polypeptide or catalytic domain domain of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Curtobacterium*, or a related organism and thus, for example, may be an allelic or species variant of the polypeptide encoding region of the polynucleotide. Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

In another embodiment, the present invention relates to a polypeptide having hexosaminidase activity encoded by a polynucleotide having a sequence identity to the mature polypeptide coding sequence of SEQ ID NO 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 29 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 30 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 32 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 33 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 35 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having hexosaminidase activity encoded by a polynucleotide having a sequence identity to the mature polypeptide coding sequence of SEQ ID NO 32 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO 20, SEQ ID NO 33, SEQ ID NO 34 or SEQ ID NO 35 comprising a substitution, and/or deletion, and/or insertion at one or more (e.g., several) positions. In an embodiment, the number of positions comprising one or more amino acid substitutions, and/or one or more amino acid deletions, and/or one or more amino acid insertions or any combination thereof in SEQ ID NO 20 is not more than 49, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49. In another embodiment, the number of positions comprising one or more amino acid substitutions, and/or one or more amino acid deletions, and/or one or more amino acid insertions or any combination thereof in SEQ ID NO 20, SEQ ID NO 33, SEQ ID NO 34 or SEQ ID NO 35 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO 20, SEQ ID NO 33, SEQ ID NO 34 or SEQ ID NO 35 is not more than 10, e.g., 1, 2, 3, 4, 5, 6, 7, 8, 9 or 10. In another embodiment, the number of substitutions and/or deletions and/or insertions in SEQ ID NO 20, SEQ ID NO 33, SEQ ID NO 34 or SEQ ID NO 35 is not more than 10, e.g., 1, 2, 3, 4, 5, 6, 7, 8, 9 or 10. In a further embodiment, the number of substitutions in SEQ ID NO 20, SEQ ID NO 33, SEQ ID NO 34 or SEQ ID NO 35 is not more than 10, e.g., 1, 2, 3, 4, 5, 6, 7, 8, 9 or 10. In a further embodiment, the number of conservative substitutions in SEQ ID NO 20, SEQ ID NO 33, SEQ ID NO 34 or SEQ ID NO 35 is not more than 10, e.g., 1, 2, 3, 4, 5, 6, 7, 8, 9 or 10. In an embodiment, the variant has at least at least 70%, e.g. at least 80%, at least 90%, at least 95% or at least 100% of the hexosaminidase activity compared to the parent e.g. compared to SEQ ID NO 20, SEQ ID NO 33, SEQ ID NO 34 or SEQ ID NO 35.

The amino acid changes in the mature polypeptide of SEQ ID NO 20, SEQ ID NO 33, SEQ ID NO 34 or SEQ ID NO 35 described above may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R.L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for hexosaminidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Hexosaminidase Activity

A polypeptide having hexosaminidase activity of the present invention may be obtained from microorganisms of any genus. For purposes of the present invention, the term "obtained from" as used herein about a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. In one aspect, the polypeptide is a polypeptide having hexosaminidase activity from a bacterium of the class Actinobacteria, such as from the order Micrococcales, or from the family Microbacteriaceae, or from the genus *Curtobacterium* or from the species *Curtobacterium oceanosedimentum, Curtobacterium flaccumfaciens, Curtobacterium luteum* or *Curtobacterium* sp. Leaf154

It will be understood that for the aforementioned species, the invention encompasses both the perfect and imperfect states, and other taxonomic equivalents, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trichophaea* or a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO 20 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, Protein Expression and Purification 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HISS, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Strepto-*

*myces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteria* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteria Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al, 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M.I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Curtobacterium* cell. In another aspect, the cell is a *Curtobacterium oceanosedimentum*, a *Curtobacterium flaccumfaciens* a *Curtobacterium luteum* or a *Curtobacterium Leaf*154 cell.

The present invention also relates to methods of producing a polypeptide of the present invention, comprising (a) cultivating a recombinant host cell of the present invention under conditions conducive for production of the polypeptide; and optionally, (b) recovering the polypeptide.

One embodiment relates to a method of producing the polypeptide selected from a polypeptide comprising the amino acid sequence shown in SEQ ID NO 20, SEQ ID NO 33, SEQ ID NO 34, SEQ ID NO 35 or a polypeptide having at least 80% sequence identity hereto, comprising cultivating a cell, which in its wild-type form produces the polypeptide, under conditions conducive for production of the polypeptide e.g. further comprising recovering the polypeptide.

One embodiment relates to a method of producing a polypeptide having hexosaminidase activity, comprising cultivating the host cell under conditions conducive for production of the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermenters in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Preferred Embodiments

Herein follows a list if preferred embodiments of the invention.
1. A cleaning composition comprising one or more polypeptides having hexosaminidase activity, wherein:
    a. the polypeptide comprises one or more Glyco_hydro_20 catalytic domains, wherein the Glyco_hydro_20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings; and
    b. at least one cleaning ingredient.
2. The cleaning composition of paragraph 1, wherein the Glyco_hydro_20 catalytic domain gives a domT score of 170 or more, such as 190 or more, such as 200 or more, such as 220 or more, such as 250 or more, such as 280 or more, such as 300 or more or such as 350 or more.

3. The cleaning composition according to any of the preceding paragraphs wherein the polypeptide having hexosaminidase activity, comprises the Glyco_hydro_20 catalytic domain and wherein the Glyco_hydro_20 catalytic domain comprises one or more motif(s) selected from the group consisting of [IV]P[ED][LVI]DXP[AN]H (SEQ ID NO 21), NYN[AS]Y[SY]LY (SEQ ID NO 22) GXDE (SEQ ID NO 41), ARAYYPV (SEQ ID NO 42), AWNDGID (SEQ ID NO 43), DDQNVGI (SEQ ID NO 44) and DPRIH (SEQ ID NO 45).
4. The cleaning composition according to paragraph 3, wherein the polypeptide comprises the motif [IV]P[ED][LVI]DXP[AN]H (SEQ ID NO 21).
5. The cleaning composition according to paragraph 3 or 4, wherein the polypeptide comprises the motif NYN[AS]Y[SY]LY (SEQ ID NO 22)
6. The cleaning composition according to paragraph 3 or 4, wherein the polypeptide comprises the motif GXDE (SEQ ID NO 41).
7. The cleaning composition according to paragraph 3 or 4, wherein the polypeptide comprises the motif ARAYYPV (SEQ ID NO 42).
8. The cleaning composition according to paragraph 3 or 4, wherein the polypeptide comprises the motif AWNDGID (SEQ ID NO 43).
9. The cleaning composition according to paragraph 3 or 4, wherein the polypeptide comprises the motif DDQNVGI (SEQ ID NO 44).
10. The cleaning composition according to paragraph 3 or 4, wherein the polypeptide comprises the motif DPRIH (SEQ ID NO 45).
11. The cleaning composition according to any of paragraph 3 to 10, wherein Glyco_hydro_20 catalytic domain has at least 60% identity, such as at least 70% identity, such as at least 80% identity, such as at least 90% identity, such as at least 95% identity, such as at least 98% identity or 100% sequence identity to SEQ ID NO 1, SEQ ID NO 2, SEQ ID NO 3 or SEQ ID NO 4.
12. The cleaning composition according to any of paragraph 3 to 10, wherein Glyco_hydro_20 catalytic domain has at least 60% identity such as at least 70% identity, such as at least 80% identity, such as at least 90% identity, such as at least 95% identity, such as at least 98% identity or 100% sequence identity to SEQ ID NO 5, SEQ ID NO 6, SEQ ID NO 7, SEQ ID NO 8, SEQ ID NO 37, SEQ ID NO 38, SEQ ID NO 39 or SEQ ID NO 40.
13. The cleaning composition according to any of the preceding composition paragraphs wherein the polypeptide having hexosaminidase activity is the amino acid sequence of SEQ ID NO 20 or polypeptides having at least 60% sequence identity, at least 70% sequence identity, at least 80% sequence identity, at least 90% sequence identity, at least 95% sequence identity or at least 100% sequence identity hereto.
14. The cleaning composition according to any of the preceding composition paragraphs wherein the polypeptide having hexosaminidase activity is the amino acid sequence of SEQ ID NO 33 or polypeptides having at least 60% sequence identity, at least 70% sequence identity, at least 80% sequence identity, at least 90% sequence identity, at least 95% sequence identity or at least 100% sequence identity hereto
15. The cleaning composition according to any of the preceding composition paragraphs wherein the polypeptide having hexosaminidase activity is the amino acid sequence of SEQ ID NO 34 or polypeptides having at least 60% sequence identity, at least 70% sequence identity, at least 80% sequence identity, at least 90% sequence identity, at least 95% sequence identity or at least 100% sequence identity hereto
16. The cleaning composition according to any of the preceding composition paragraphs wherein the polypeptide having hexosaminidase activity is the amino acid sequence of SEQ ID NO 35 or polypeptides having at least 60% sequence identity, at least 70% sequence identity, at least 80% sequence identity, at least 90% sequence identity, at least 95% sequence identity or at least 100% sequence identity hereto
17. The cleaning composition according to any of the preceding composition paragraphs wherein the polypeptide having hexosaminidase activity is the amino acid sequence of SEQ ID NO 36 or polypeptides having at least 60% sequence identity, at least 70% sequence identity, at least 80% sequence identity, at least 90% sequence identity, at least 95% sequence identity or at least 100% sequence identity hereto.
18. The cleaning composition according to any of the preceding composition paragraphs, wherein the cleaning ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
19. The cleaning composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.
20. The cleaning composition according to any of the preceding composition paragraphs wherein the composition comprises from about 10 wt % to about 50 wt % of at least one builder, preferably selected from citric acid, methylglycine-N, N-diacetic acid (MGDA) and/or glutamic acid-N, N-diacetic acid (GLDA) and mixtures thereof.
21. The cleaning composition according to any of the preceding paragraphs comprising from about 5 wt % to about 40 wt % nonionic surfactants, and from about 0 wt % to about 5 wt % anionic surfactant.

22. The cleaning composition according to paragraph 12, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.

23. The cleaning composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

24. The cleaning composition according to any of the preceding composition paragraphs, wherein the enzyme is a protease, which is of animal, vegetable or microbial origin.

25. The cleaning composition according to any of the preceding composition paragraphs, wherein the protease is chemically modified or protein engineered.

26. The cleaning composition according to any of the preceding composition paragraphs, wherein the protease is a serine protease or a metalloprotease, preferably an alkaline microbial protease or a trypsin-like protease.

27. The cleaning composition according to any of the preceding composition paragraphs, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.

28. The cleaning composition according to any of the preceding composition paragraphs, wherein the composition is capable of reducing adhesion of bacteria selected from the group consisting of *Acinetobacter* sp., *Aeromicrobium* sp., *Brevundimonas* sp., *Microbacterium* sp., *Micrococcus luteus, Pseudomonas* sp., *Staphylococcus epidermidis, Staphylococcus aureus*, and *Stenotrophomonas* sp. to a surface, or releasing the bacteria from a surface to which they adhere.

29. The cleaning composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

30. The cleaning composition according to any of the preceding composition paragraphs, wherein the composition is selected from liquid detergent, powder detergent and granule detergent compositions.

31. Use of a polypeptide comprising one or more Glyco_hydro_20 catalytic domains, wherein the Glyco_hydro_20 catalytic domain gives a domT score of 150 or more when queried using a Profile Hidden Markov Model prepared using SEQ ID NOs: 1 to 7 using the software program hmmbuild, when the query being carried out using the hmmscan software program with default settings, for deep cleaning of an item, wherein the item is a textile.

32. Use according to paragraph 31, wherein the polypeptide comprises one or more of the motif(s) [IV]P[ED][LVI]DXP[AN]H (SEQ ID NO 21) NYN[AS]Y[SY]LY (SEQ ID NO 22) or GXDE (SEQ ID NO 41).

33. Use according to paragraph 31 or 32, wherein Glyco_hydro_20 catalytic domain has at least 60% identity, such as at least 70% identity, such as at least 80% identity, such as at least 90% identity, such as at least 95% identity, such as at least 98% identity or 100% sequence identity to SEQ ID NO 1, SEQ ID NO 2, SEQ ID NO 3 or SEQ ID NO 4.

34. Use according to any of paragraph 31 or 32, wherein Glyco_hydro_20 catalytic domain has at least 60% identity such as at least 70% identity, such as at least 80% identity, such as at least 90% identity, such as at least 95% identity, such as at least 98% identity or 100% sequence identity to SEQ ID NO 5, SEQ ID NO 6, SEQ ID NO 7, SEQ ID NO 8, SEQ ID NO 37, SEQ ID NO 38, SEQ ID NO 39 or SEQ ID NO 40.

35. Use of a polypeptide according to any of paragraphs 57 to 65 for deep cleaning of an item 36. Use according to any of the preceding use paragraphs for preventing, reducing or removing stickiness of the item.

37. Use according to any of the preceding use paragraphs for pre-treating stains on the item.

38. Use according to any of the preceding use paragraphs for preventing, reducing or removing re-deposition of soil during a wash cycle.

39. Use according to any of the preceding use paragraphs for preventing, reducing or removing adherence of soil to the item.

40. Use according to any of the preceding use paragraphs for maintaining or improving the whiteness of the item.

41. Use according to any of the preceding use paragraphs, wherein a malodor is reduced or removed from the item.

42. Use according to any of the preceding composition use paragraphs, wherein the surface is a textile surface.

43. Use according to any of the preceding composition use paragraphs, wherein the textile is made of cotton, Cotton/Polyester, Polyester, Polyamide, Polyacryl and/or silk.

44. A method for laundering an item comprising the steps of:
   a. Exposing an item to a wash liquor comprising a polypeptide of paragraphs 57-65 or a composition according to any of paragraphs 1-30;
   b. Completing at least one wash cycle; and
   c. Optionally rinsing the item, wherein the item is a textile.

45. Method according to paragraph 44, wherein the pH of the wash liquor is in the range of 1 to 11.

46. Method according to any of the preceding method paragraphs, wherein the pH of the wash liquor is in the range 5.5 to 11, such as in the range of 7 to 9, in the range of 7 to 8 or in the range of 7 to 8.5.

47. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50°

C., in the range of 15° C. to 40° C., in the range of 20° C. to 40° C., in the range of 15° C. to 30° C. or in the range of 20° C. to 30° C.
48. Method according to any of the preceding method paragraphs, wherein the temperature of the wash liquor is from about 20° C. to about 40° C.
49. Method according to any of the preceding method paragraphs, wherein the temperature of the wash liquor is from about 15° C. to about 30° C.
50. Method according to any of the preceding method paragraphs, wherein stains present on the item is pretreated with a polypeptide of paragraphs 57-65 or a cleaning composition according to any of paragraphs 1-30.
51. Method according to any of the preceding method paragraphs, wherein stickiness of the item is reduced.
52. Method according to any of the preceding method paragraphs, wherein redeposition of soil is reduced.
53. Method according to any of the preceding method paragraphs, wherein adherence of soil to the item is reduced or removed.
54. Method according to any of the preceding method paragraphs, wherein whiteness of the item is maintained or improved.
55. Method according to any of the preceding method paragraphs, wherein malodor is reduced or removed from the item.
56. Method according to any of the preceding method paragraphs, wherein the concentration of the polypeptide having hexosaminidase activity in the wash liquor is at 0.001 mg of polypeptide, such as at least 0.05 mg of protein, or at least 1.0 mg of protein, or at least 1.5 mg of protein per liter of wash liquor, optionally the concentration of polypeptide in the wash liquor is in the range 0.0002 mg/L to 2 mg/L, such as 0.002 mg/L to 2 mg/L, such as 0.2 mg/L to 2 mg/L or in the range of 0.00001 mg/L to 10 mg/L or in the range of in the range of 0.0001 mg/L to 10 mg/L, or in the range of 0.001 mg/L to 10 mg/L, or in in the range of 0.01 mg/L to 10 mg/L per liter of wash liquor, optionally the concentration of the polypeptide of the invention is 0.00001% to 2 wt %, such as 0.0001 to 0.1 wt %, such as 0.0005 to 0.1 wt %, such as 0.001 to 0.1 wt %, such as 0.001 to 0.5 wt %, such as 0.002 to 0.5 wt % or 0.0002 to 0.09 wt % in the total detergent concentration.
57. A polypeptide having hexosaminidase activity, selected from the group consisting of:
   a. a polypeptide having at least 60% e.g. 70%, 75%, 80%, 85%, 90% or 95% sequence identity to the mature polypeptide of SEQ ID NO 12, SEQ ID NO 25, SEQ ID NO 26, SEQ ID NO 27, SEQ ID NO 28 or a polypeptide having at least 60% e.g. 70%, 75%, 80%, 85%, 90% or 95% sequence identity to the mature polypeptide of SEQ ID NO 20, SEQ ID NO 33, SEQ ID NO 34, SEQ ID NO 35 or SEQ ID NO 36;
   b. a polypeptide encoded by a polynucleotide that hybridizes under low stringency conditions with
      i. the mature polypeptide coding sequence of SEQ ID NO 16, SEQ ID NO 29, SEQ ID NO 30, SEQ ID NO 31, or SEQ ID NO 32,
      ii. the cDNA sequence thereof, or
      iii. the full-length complement of (i) or (ii);
   c. a polypeptide encoded by a polynucleotide having at least 60% sequence identity to the mature polypeptide coding sequence of SEQ ID NO 16, SEQ ID NO 29, SEQ ID NO 30, SEQ ID NO 31, SEQ ID NO 32 or the cDNA sequence thereof;
   d. a variant of the mature polypeptide of SEQ ID NO 20, SEQ ID NO 33, SEQ ID NO 34, SEQ ID NO 35 or SEQ ID NO 36 comprising a substitution, deletion, and/or insertion at one or more positions compared to the sequences SEQ ID NO 20, SEQ ID NO 33, SEQ ID NO 34, SEQ ID NO 35 or SEQ ID NO 36 respectively;
   e. a fragment of the polypeptide of (a), (b), (c), or (d) that has hexosaminidase activity; and
   f. a polypeptide comprising any of the motif(s) selected from the group consisting of [IV]P[ED][LVI]DXP[AN]H (SEQ ID NO 21), NYN[AS]Y[SY]LY (SEQ ID NO 22), GXDE (SEQ ID NO 41), ARAYYPV (SEQ ID NO 42), AWNDGID (SEQ ID NO 43), DDQNVGI (SEQ ID NO 44) and DPRIH (SEQ ID NO 45).
58. The polypeptide of paragraph 57, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 12 or to the polypeptide shown in SEQ ID NO 20.
59. The polypeptide of paragraph 57, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 25 or to the polypeptide of SEQ ID NO 33.
60. The polypeptide of paragraph 57, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 26 or to the polypeptide of SEQ ID NO 34.
61. The polypeptide of paragraph 57, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 27 or to the polypeptide of SEQ ID NO 35.
62. The polypeptide of paragraph 57, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 28 or to the polypeptide of SEQ ID NO 36.
63. The polypeptide according to paragraph 57 to 62, which is encoded by a polynucleotide that hybridizes under low stringency conditions, low-medium stringency conditions, medium stringency conditions, medium-high stringency conditions, high stringency conditions, or very high stringency conditions with
   a. the mature polypeptide coding sequence of SEQ ID NO 16, SEQ ID NO 29, SEQ ID NO 30, SEQ ID NO 31, SEQ ID NO 32,
   b. the cDNA sequence thereof, or
   c. the full-length complement of (i) or (ii).
64. The polypeptide according to any of paragraphs 57-63, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 16 or the cDNA sequence thereof.

65. The polypeptide according to any of paragraphs 57 to 64, comprising or consisting of SEQ ID NO 20, SEQ ID NO 33, SEQ ID NO 34, SEQ ID NO 35, SEQ ID NO 36 or the mature polypeptide of SEQ ID NO 12. SEQ ID NO 25, SEQ ID NO 26, SEQ ID NO 27 or SEQ ID NO 28.

66. A polynucleotide encoding the polypeptide according to any of paragraphs 57-65.

67. A nucleic acid construct or expression vector comprising the polynucleotide of paragraph 66 operably linked to one or more control sequences that direct the production of the polypeptide in an expression host.

68. A recombinant host cell comprising the polynucleotide of paragraph 66 operably linked to one or more control sequences that direct the production of the polypeptide.

69. A method of producing the polypeptide of any of paragraphs 57-65, comprising cultivating a cell, which in its wild-type form produces the polypeptide, under conditions conducive for production of the polypeptide.

70. The method of paragraph 69, further comprising recovering the polypeptide.

71. A method of producing a polypeptide according to any of paragraphs 57-65, comprising cultivating the host cell of paragraph 68 under conditions conducive for production of the polypeptide.

72. The method of paragraph 71, further comprising recovering the polypeptide.

73. A nucleic acid construct or expression vector comprising a gene encoding a protein operably linked to the polynucleotide of paragraph 66, wherein the gene is foreign to the polynucleotide encoding the signal peptide.

74. A recombinant host cell comprising a gene encoding a protein operably linked to the polynucleotide of paragraph 66, wherein the gene is foreign to the polynucleotide encoding the signal peptide.

75. A method of producing a protein, comprising cultivating a recombinant host cell comprising a gene encoding a protein operably linked to the polynucleotide of paragraph 54, wherein the gene is foreign to the polynucleotide encoding the signal peptide, under conditions conducive for production of the protein.

76. The method of paragraph 75, further comprising recovering the protein.

77. The recombinant host cell of paragraph 74 further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

78. The recombinant host cell of paragraph 77, wherein the second polypeptide of interest is heterologous or homologous to the host cell.

79. The recombinant host cell of paragraph 68 or 74, which is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

80. The recombinant host cell of paragraph 68 or 74, which is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus,* or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* host cell.

81. A method of producing the second polypeptide of interest as defined paragraph 65 comprising cultivating the host cell of any of paragraphs 68 or 74 under conditions conducive for production of the second polypeptide of interest.

82. The method of paragraph 81, further comprising recovering the second polypeptide of interest.

83. Item laundered according to the method of any of paragraphs 44-56.

Preferred embodiments include:

1. A cleaning composition comprising one or more polypeptides having hexosaminidase activity, wherein:
   (a) the polypeptide comprises one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, and
   (b) at least one cleaning ingredient.

2. The composition of paragraph 1, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 20.

3. The composition of any of paragraphs 1 or 2, wherein the polypeptide comprises the conserved motif I [IV]P[ED][LVI]DXP[AN]H (SEQ ID NO 21) and/or the conserved motif II NYN[AS]Y[SY]LY (SEQ ID NO 22).

4. The composition according to any of paragraphs 1 to 3 wherein the composition is a cleaning composition such as a laundry or dish wash composition 5. The composition according to paragraph 4, wherein the cleaning ingredient is selected from,
   a) at least one builder,
   b) at least one surfactant, and
   c) at least one bleach component.

6. The composition according to paragraph 5, wherein the composition comprises at least one builder, wherein the builder is added in an amount of about 0-65% by weight, preferably about 40-65% by weight, particularly about 20-65% by weight, particularly from 10% to 50% by weight and wherein the builder is selected among phosphates, sodium citrate builders, sodium carbonate, sodium silicate, sodium and zeolites.

7. The composition according to paragraph 6 wherein the builder is selected from citric acid, methyl glycine-N,N-diacetic acid (MGDA) and/or glutamic-N,N-diacetic acid (GLDA) and mixtures thereof.

8. The composition according to any of the preceding paragraphs comprising 1-40 wt %, preferably from 0.5-30 wt %, of at least one bleaching component, wherein the bleach component includes a percarbonate and bleach catalyst, preferably a manganese compound.

9. The composition according to paragraph 8 wherein at least one bleach component is a peroxide, preferably percabonate and a catalyst preferably a metal-containing bleach catalyst such as 1,4,7-trimethyl-1,4,7-triazacyclononane or manganese (II) acetate tetrahydrate (MnTACN).

10. The composition according to any of the previous paragraphs, wherein the composition comprise at least one surfactant wherein the surfactant is anionic and/or nonionic.

11. The composition according to paragraph 10, wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant.

12. The composition according to any of paragraphs 10 or 11, wherein the composition comprises from about 5 wt % to about 50 wt %, from about 5 wt % to about 40 wt %, from about 5 wt % to about 30 wt, from about 5 wt % to about 20 wt, from about 5 wt % to about 10 wt % nonionic surfactant 13. The composition according to any of paragraphs 10 to 12, wherein the anionic surfactant is selected from linear alkylbenzenesulfonates (LAS) isomers of LAS, alcohol ether sulfate (AEO, AEOS) and sodium lauryl ether sulfate and sodium laureth sulfate (SLES).

14. The composition according to any of paragraphs 10 to 13, wherein the nonionic surfactant is selected from alcohol ethoxylates (AE or AEO), alcohol propoxylates, alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, N-acyl N-alkyl derivatives of glucosamine (glucamides, GA, or fatty acid glucamides, FAGA) and combinations thereof.

16. Use of a composition of any of paragraphs 1 to 14 for deep-cleaning of an item, wherein the item is a textile.

17. A laundering method for laundering an item comprising the steps of:
   Exposing an item to a wash liquor comprising a polypeptide having at least 60% sequence identity to the polypeptide of SEQ ID NO 20 or a detergent composition according to any of paragraphs 1 to 14;
   Completing at least one wash cycle; and
   Optionally rinsing the item,
   wherein the item is a textile.

18. Use of a polypeptide, having hexosaminidase activity, comprising one or more GH20 catalytic domains, wherein the GH20 catalytic domain gives a domT score of 150 or more when queried using a Profile Hidden Markov Model prepared using SEQ ID NOs: 1 to 7 using the software program hmmbuild, the query being carried out using the hmmscan software program with default settings, in a cleaning process, such as laundry and/or dish wash.

19. Use of a the polypeptide, having hexosaminidase activity, comprising one or more GH20 catalytic domains, wherein the GH20 catalytic domain gives a domT score of 150 or more when queried using a Profile Hidden Markov Model prepared using SEQ ID NOs: 1 to 7 inclusive using the software program hmmbuild, the query being carried out using the hmmscan software program with default settings, for deep cleaning of an item, wherein the item is a textile.

20. Use according to paragraph 17 for preventing, reducing or removing stickiness of the item.

21. Use according to any of paragraphs 17 or 18 for preventing, reducing or removing redeposition of soil during a wash cycle.

22. Use according to any of the preceding paragraphs, wherein the polypeptide is selected from the group consisting of a polypeptide having at least 60% sequence identity to the polypeptide of SEQ ID NO 20 and at least one cleaning ingredient.

23. Use of paragraph 21, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 20.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Assays and Detergent Compositions

Detergent Compositions

The below mentioned detergent composition may be used in combination with the enzyme of the invention.

Biotex Black (Liquid)

5-15% Anionic surfactants, <5% Nonionic surfactants, perfume, enzymes, DMDM and hydantoin.

Composition of Ariel Sensitive White & Color, Liquid Detergent Composition

Aqua, Alcohol Ethoxy Sulfate, Alcohol Ethoxylate, Amino Oxide, Citric Acid, C12-18 topped palm kernel fatty acid, Protease, Glycosidase, Amylase, Ethanol, 1.2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-42485 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent A (Liquid)

Ingredients: 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w)

Composition of model detergent N (liquid)

Ingredients: NaOH 0.87%, MPG (Monopropylenglycol) 6%, Glycerol 2%, Soap-soy 2.75%, Soap-coco 2.75%, PCA (Sokalon CP-5) 0.2%, AEO Biosoft N25-7(NI) 16%, Sodium formiate 1%, Sodium Citrate 2%, DTMPA 0.2%, Ethanol (96%) 3%, adjustment of pH with NaOH or Citric acid ass water to 100% (all percentages are w/w (weight volume).

Composition of Persil Universal Gel

Ingredients: 15-30% Anionic surfactants, 5-15% Nonionic surfactant, <5% Phosphonate, soap, Amyl cinnamal, Butylphenyl methylpropional, limonene, Gernaiol, Optical brightener, enzymes.

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour&Style (Liquid)

Ingredients: 5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.

Composition of Persil Small & Mighty (Liquid)

Ingredients: 15-30% Anionic surfactants, Non-ionic surfacts, 5-15% Soap, <5% Polycarboxylates, Perfume, Phosphates, Optical Brighteners Persil 2 In1 with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Parfum, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbene-sulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Parfum, Tetrasodium Etidronate, Sodium sulfate, Sodium Polyacrylate, Dimethicone, Disodium Anilinomorpholinotriazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin, Persil Colour Care Biological Powder Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Parfum, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Parfum, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 In1 with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15

Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2 In1 with Comfort Sunshiny Days

Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process),Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium slilcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift Colour&Style (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)

Ingredients: 5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase, Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/ polydimethyl silicone.

Tide TOTALCARE HE Liquid, Renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide liquid HE Free:

Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:

Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, Dimethicone.

Tide for Coldwater HE Free Liquid:

Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:

Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:

Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:

Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:

Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:

Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:

Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to go Stain Eraser:

Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:

Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:

Polyvinyl Alcoholpouch film, wherein there is packed a liquid part and a powder part: Liquid Ingredients: Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:

Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:

Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:

Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/Mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Pwdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Wash Assays

Mini Launder-O-Meter (MiniLOM) Model Wash System

MiniLOM is a mini wash system in which washes are performed in 50 ml test tubes placed in a Stuart rotator. Each tube simulates one small washing machine and during an experiment, each will contain a solution of a specific detergent/enzyme system to be tested along with the soiled and unsoiled fabrics it is tested on. Mechanical stress is achieved via rotation (typically 20 rpm), and the temperature is controlled by placement of the rotator in a heating cabinet/room.

Terg-O-Timeter (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines. Equipment: The water bath with 12 steel beakers and 1 rotating arm per beaker with capacity of 500 or 1200 mL of detergent solution. Temperature ranges from 5 to 80° C. The water bath must be filled up with deionised water. Rotational speed can be set up to 70 to 120 rpm/min. Set temperature in the Terg-O-Tometer and start the rotation in the water bath. Wait for the temperature to adjust (tolerance is +/−0.5° C.). All beakers shall be clean and without traces of prior test material. The wash solution with desired amount of detergent, temperature and water hardness is prepared in a bucket. The detergent is allowed to dissolve during magnet stirring for 10 min. Wash solution shall be used within 30 to 60 min after preparation. 800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The soiled swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

The present invention is further described by the following examples that should not be construed as limiting the scope of the invention.

Assay

Assay 1: Testing of Hexosaminidase Activity

The hexosaminidase activity of the mature polypeptide with SEQ ID NO 20 was determined using 4-nitrophenyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 50 mM 2-(N-morpholino) ethanesulfonic acid pH 6 buffer, 1.5 mg/ml 4-nitrophenyl N-acetyl-3-D-glucosaminide and 20 µg/ml purified enzyme sample in a total reaction volume of 100 µl. Blank samples without enzyme were run in parallel. The reactions were carried out at 37° C. in a Thermomixer comfort (Eppendorf). After 10 minutes of incubation, 5 µl 1 M NaOH was added to each reaction mixture to stop the enzymatic reaction. The absorbance was read at 405 nm using a POLARstar Omega plate reader (BMG LABTECH) to estimate the formation of 4-nitrophenolate ion released because of enzymatic hydrolysis of the 4-nitrophenyl N-acetyl-β-D-glucosaminide substrate.

The results are summarized in the table below. Table 1 shows the average absorbance measured at 405 nm for each reaction performed in triplicates. It is seen that the absorbance is higher for the reaction carried out with SEQ ID NO 20 compared to blank without enzyme which demonstrates that SEQ ID NO 20 exhibit hexosaminidase activity.

TABLE 1

| Hexosaminidase activity of SEQ ID NO 20. | | | |
| --- | --- | --- | --- |
| Enzyme | Enzyme concentration | A405 nm | $\Delta A405$ nm (A405 $nm_{sample}$ − A405 $nm_{blank}$) |
| Blank | 0 µg/ml | 0.179 | — |
| SEQ ID NO 20 | 20 µg/ml | 0.376 | 0.197 |

Assay 2 Testing of Hexosaminidase Activity

The hexosaminidase activity of the mature polypeptides with SEQ ID NO 20, SEQ ID NO 33, SEQ ID NO 34 SEQ ID NO 35 and SEQ ID NO 36, was determined using 4-Methylumbeliferyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 20 mM 3-morpholinopropane-1-sulfonic acid pH 7 buffer, 5 mM 4-Methylumbeliferyl N-acetyl-β-D-glucosaminide and 20 nM purified enzyme sample in a total reaction volume of 200 µl. Blank samples without enzyme were run in parallel. The reactions were carried out at ambient temperature 20-25° C. The reaction kinetics was followed immediately after mixing of enzyme and substrate using a SpectraMax M2e plate reader. Excitation wavelength was set to 368 nm and fluorescence emission reading was done at 448 nm. The reaction was followed for 30 min with 60 second intervals. Increase in fluorescence signal was used to estimate the formation of 4-Methylumbeliferyl ion released because of enzymatic hydrolysis of the 4-Methyl-umbeliferyl N-acetyl-β-D-glucosaminide substrate. The results are summarized in the table below. The table shows the average initial rate of reaction measured as relative fluorescence units per minute (RFU/min) using excitation at 368 nm and fluorescence emission at 448 nm for each reaction performed in triplicates. It is seen that the reaction initial rate is higher for the reaction carried out with SEQ ID NO 20, SEQ ID NO 33, SEQ ID NO 34 SEQ ID NO 35 and SEQ ID NO 36 compared to blank without enzyme which demonstrates that SEQ ID NO 20, SEQ ID NO 33, SEQ ID NO 34 SEQ ID NO 35 and SEQ ID NO 36 exhibit hexosaminidase activity.

TABLE 2

Hexosaminidase activity of SEQ ID NO 20, SEQ ID NO 33, SEQ ID NO 34 SEQ ID NO 35 and SEQ ID NO 36. Δ Reaction initial rate (RFU/min) = (Reaction initial rate$_{sample}$ − Reaction initial rate$_{blank}$)

| Enzyme | Enzyme concentration | Reaction initial rate (RFU/min) | Δ Reaction initial rate (RFU/min) |
|---|---|---|---|
| Blank | 0 nM | 1.1 | — |
| SEQ ID NO 20 | 25 nM | 10.3 | 9.2 |
| SEQ ID NO 33 | 25 nM | 7.7 | 6.6 |
| SEQ ID NO 35 | 25 nM | 20.7 | 19.6 |
| SEQ ID NO 34 | 25 nM | 10.4 | 9.3 |
| SEQ ID NO 36 | 25 nM | 6.4 | 5.3 |

EXAMPLES

Example 1

The DNA encoding the Glyco_hydro_20 hexosaminidase having the polypeptide comprised in with SEQ ID NO 12, 25, 26 and 27 were isolated from the bacterial strains *Curtobacterium oceanosedimentum*; *Curtobacterium flaccumfaciens*; *Curtobacterium luteum*, *Curtobacterium oceanosedimentum* respectively, isolated from environmental soil samples collected in USA and Germany (see table 2). Chromosomal DNA from the *Curtobacterium* sp strains was isolated by QIAamp DNA Blood Mini Kit (Qiagen, Hilden, Germany) and subjected to full genome sequencing using Illumina technology. The genome sequence was analyzed for protein sequences that have glycosyl hydrolase domains. Four Glyco_hydro_20 genes and corresponding sequences (SEQ ID NO 16, 29, 30 and 31) were identified from the *Curtobacterium* sp. strains. The Glyco_hydro_20 gene and corresponding sequence (SEQ ID NO 32) encoding the Glyco_hydro_20 hexosaminidase having polypeptide sequence SEQ ID NO 28 was found in the public database from the donor *Curtobacterium* sp. Leaf154 (DSM102595 strain, origin Switzerland). The codon optimized synthetic DNA encoding the mature peptide sequence of the Glyco_hydro_20 hexosaminidases were ordered from the company Geneart (SEQ ID NO 20, 33, 34, 35 and 36)

TABLE 3

| Enzyme | Donor | Country of origin |
|---|---|---|
| SEQ ID NO 20 | *Curtobacterium oceanosedimentum* | USA |
| SEQ ID NO 33 | *Curtobacterium flaccumfaciens* | USA |
| SEQ ID NO 34 | *Curtobacterium luteum* | Germany |

TABLE 3-continued

| Enzyme | Donor | Country of origin |
|---|---|---|
| SEQ ID NO 35 | *Curtobacterium oceanosedimentum* | USA |
| SEQ ID NO 36 | *Curtobacterium* sp. Leaf154 | Switzerland |

Example 2: Cloning and Expression of Glyco_Hydro_20 Hexosaminidases

The codon optimized synthetic genes encoding the mature peptide sequences of the hexosaminidase with SEQ ID NO 20, 33, 35 and 36 were inserted into a *Bacillus* expression vector as described in WO12/025577. Briefly, the DNA encoding the mature peptide of the Glyco_hydro_20 hexosaminidase gene was cloned in frame to a *Bacillus clausii* secretion signal (BcSP; with the following amino acid sequence: MKKPLGKIVASTALLISVAFSSSIASA (SEQ ID NO 23). BcSP replaced the native secretion signal in the gene. Downstream of the BcSP sequence, an affinity tag sequence was introduced to ease the purification process (His-tag; with the following amino acid sequence: HHHHHHPR (SEQ ID NO 24) The gene that was expressed therefore comprised the BcSP sequence followed by the His-tag sequence followed by the mature wild type Glyco_hydro_20 sequence. The DNA encoding the mature peptide of the Glyco_hydro_20 beta-hexosaminidase gene SEQ ID 34 was amplified from the *Curtobacterium luteum* genomic DNA by standard PCR techniques using specific primers containing an overhang to the cloning vector. The gene was consecutively cloned in frame to a *Bacillus clausii* secretion signal as described above. The final expression plasmid (BcSP-His-tag-Glyco_hydro_20) was transformed into a *Bacillus subtilis* expression host. The Glyco_hydro_20 BcSP-fusion gene was integrated by homologous recombination into the *Bacillus subtilis* host cell genome upon transformation. The gene construct was expressed under the control of a triple promoter system (as described in WO99/43835). The gene coding for chloramphenicol acetyltransferase was used as maker (as described in (Diderichsen et al., 1993, *Plasmid* 30: 312-315)). Transformants were selected on LB media agar supplemented with 6 micrograms of chloramphenicol per ml. One recombinant *Bacillus subtilis* clone containing the Glyco_hydro_20 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

Example 3: His Tag Purification Method

The His-tagged Glyco_hydro_20 hexosaminidase enzyme was purified by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzyme was checked by SDS-PAGE and the concentration of the enzyme determined by Absorbance 280 nm after a buffer exchange in 50 mM HEPES, 100 mM NaCl pH7.0

Example 4: Biofilm Assay

*Staphylococcus aureus* was kindly provided by Iñigo Lasa (Valle et al., Mol Microbio 1.2003 May; 48 (4):1075-87).

The strain was grown on trypticase soy agar (TSA) at 37° C. overnight. Next day, a single colony was transferred to 15 ml trypticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L Model detergent A containing 0 (control) or 20, 10, 5, 2.5, 1.25, 0.62, 0.31, 0.16, 0.08, 0.04, 0.02 and 0.01 µg/mL of enzyme (the mature polypeptide having SEQ ID NO 20, 33, 34, 35 and 36). After incubation at 37° C. for 1 hour, wells were washed with water and stained for 15 min with 100 µL of 0.095% crystal violet solution (SIGMA V5265). Wells were then rinsed twice with 100 µL water, dried and the plates were scanned. The lowest concentration of each enzyme that could remove the visible formation of biofilm of *S. aureus* after 1 hour incubation, in the presence and absence of detergent was determined (see Table 4). All enzymes were assayed per duplicate with similar results.

Table 4. Minimal concentration of enzyme that can reduce the visible formation of *S. aureus* after 1 hour incubation in either hard water or Model detergent A.

TABLE 4

| Enzyme | Minimal concentration for biofilm reduction in Model A µg/mL | Minimal concentration for biofilm reduction in Hard water µg/mL |
| --- | --- | --- |
| SEQ ID NO 20 | 5 | 1.25 |
| SEQ ID NO 33 | 0.31 | 0.04 |
| SEQ ID NO 34 | 0.16 | 0.02 |
| SEQ ID NO 35 | 1.25 | 0.08 |
| SEQ ID NO 36 | 5 | 2.5 |

Example 5 Deep-Cleaning of Polypeptides with Hexosaminidase Activity in Liquid Model Detergent

*Staphylococcus aureus* (kind gift from Inigo Lasa (Valle et al., *Mol Microbio* 1.2003 May; 48 (4):1075-87) was used as model microorganism in the present example. *S.aureus* was restreaked on Tryptone Soya Agar (TSA) (pH 7.3) (CM0131; Oxoid Ltd, Basingstoke, UK) and incubated for 1 day at 37° C. A single colony was inoculated into 10 mL of TSB and the culture was incubated for 16 hours at 37° C. with shaking (200 rpm). After propagation, the *S.aureus* culture was diluted (1:100) in fresh TSB+1% glucose (24563; Roquette Freres) and 2 mL aliquots were added to the wells of 12-well polystyrene flat-bottom microplates (3512; Costar, Corning Incorporated, Corning, N.Y., USA), in which round swatches (diameter 2 cm) of sterile polyester (prewashed WFK30A) had been placed. Sterile TSB+1% glucose was added to control wells. After 48 h at 37° C. (static incubation), the swatches were rinsed twice with 15° dH water. Five rinsed swatches (sterile or with *S. aureus*) were placed in 50 mL test tubes and 10 mL of wash liquor (15° dH water with 0.2 g/L iron(III) oxide nanopowder (544884; Sigma-Aldrich) with 3.33 g/L liquid model A detergent) and 0.2 ppm enzyme (mature polypeptide with SEQ ID NO 20) was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night.

The color difference (L) values were measured using a Handheld Minolta CR-300, and are displayed in table 5. Delta values ($L_{(swatch\ washed\ with\ enzyme)} - L_{(swatch\ washed\ without\ enzyme)}$) are also indicated.

The results show that the hexosaminidases display deep-cleaning properties in model detergent A.

TABLE 5

Deep-cleaning effects of hexosaminidase in model detergent A

| Enzyme | Enzyme concentration (ppm) | L values | ΔL (Lwith enzyme − Lwithout enzyme) |
| --- | --- | --- | --- |
| No enzyme | 0 | 102.9 | |
| SEQ ID NO 20 | 0.2 | 108.8 | 5.9 |

Example 6 Deep-Cleaning Effects of Hexosaminidases in Liquid Model Detergent on Biofilm Swatches

*Staphylococcus aureus* biofilms were grown on textile swatches (wfk30A) as previously described (example 5). Swatches incubated with sterile medium were included as controls. For examining the deep-cleaning properties of the hexosaminidases, five rinsed swatches (sterile or with *S.aureus*) were placed in 50 mL conical centrifuge tubes and 10 mL of wash liquor (15° dH water with 0.2 g/L iron(III) oxide nanopowder (544884; Sigma-Aldrich) with 3.33 g/L liquid model A detergent) and 2 ppm enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night. The color difference (L) values were measured using a Handheld Minolta CR-300, and are displayed in table 6. Delta values ($L_{(swatch\ washed\ with\ enzyme)} - L_{(swatch\ washed\ without\ enzyme)}$) are also indicated.

The results show that these hexosaminidases also display deep-cleaning properties in model A liquid detergent.

TABLE 6

Deep-cleaning effects of hexosaminidase in model A detergent

| Swatch | Enzyme | Enzyme concentration (ppm) | L values | ΔL (Lwith enzyme − Lwithout enzyme) |
| --- | --- | --- | --- | --- |
| Clean Textile | No enzyme | 0 | 91.9 | |
| *S. aureus* biofilm swatch | No enzyme | 0 | 83.3 | |
| *S. aureus* biofilm swatch | SEQ ID NO 33 | 2 | 88.1 | 4.8 |
| *S. aureus* biofilm swatch | SEQ ID NO 35 | 2 | 89.6 | 6.3 |
| *S. aureus* biofilm swatch | SEQ ID NO 34 | 2 | 89.0 | 5.7 |
| *S. aureus* biofilm swatch | SEQ ID NO 36 | 2 | 86.9 | 3.6 |

Combined with the previous example, the results show that all the polypeptides of the invention have deep-cleaning properties i.e. disrupt and/or remove the biofilm components of the biofilm tested when compared to samples comprising no enzyme.

Example 7 Deep-Cleaning Properties of the Hexosaminidase on Swatches Soiled with EPS from S.Aureus A crude extract of biofilm extracellular polymeric substances (EPS) were prepared from S.aureus (kind gift from Iñigo Lasa (Valle, J., A. Toledo-Arana, C. Berasain, J. M. Ghigo, B. Amorena, J. R. Penades, and I. Lasa. 2003, Mol. Microbiol. 48:1075-1087) as follows: The strain was restreaked on Tryptone Soya Agar (TSA) (pH 7.3) (CM0131; Oxoid Ltd, Basingstoke, UK) and incubated for 1 day at 37° C. 500 mL of TSB+2% glucose (24563; Roquette Freres) was then inoculated, aliquoted into 50 ml conical centrifuge tubes (339652; Thermo Scientific Nunc) (33 ml in each), and incubated for 48 hours at 37° C. with shaking (200 rpm). The cells were subsequently pelleted by centrifugation (10 min, 6000 g, 25° C.), pooled and resuspended in a total of 4 ml 3M NaCl. The suspension was vortexed vigorously and incubated for 15 min at ambient temperature to extract the surface-associated EPS. The cells were then re-pelleted (10 min, 5000 g, 25° C.) and the EPS-containing supernatant was retrieved and diluted to 10 ml with sterile MilliQ water. The supernatant was sterile filtered twice (0.45 µm followed by 0.2 µm), tested for sterility and stored at −20° C. until further use. For wash performance testing, 50 ul aliquots of the EPS extract were spotted on sterile textile swatches (WFK20A, cotton/polyester blend) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 3.33 g/L liquid model A detergent) and 0.2 µg/ml or 2 µg/ml enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night. The tristimulus light intensity (Y) values were measured using a DigiEYE colour measurement and imaging system (VeriVide) equipped with a Nikon D90 digital camera, and are displayed in table 7.

Delta values ($Y_{(swatches\ washed\ with\ enzyme)} - Y_{(swatches\ washed\ without\ enzyme)}$) are also indicated. The data clearly shows that the hexosaminidases show direct deep-cleaning properties against the EPS of S.aureus.

TABLE 7

Deep-cleaning effects of hexosaminidase on swatches soiled with EPS from S. aureus

| Origin of EPS | Enzyme | Enzyme concentration (ppm) | Average Y values | ΔY |
|---|---|---|---|---|
| Clean textile, no EPS | | 0 | 85.1 | |
| S. aureus EPS | | 0 | 61.0 | |
| S. aureus EPS | SEQ ID NO 35 | 0.2 | 71.7 | 10.7 |
| S. aureus EPS | SEQ ID NO 35 | 2 | 81.1 | 20.1 |

Example 8 Deep-Cleaning Effects of Hexosaminidase in Liquid Model Detergent on EPS from Other Microorganisms Crude extracts of biofilm extracellular polymeric substances (EPS) were prepared from Pseudomonas fluorescens (Isolate from Iceland) and Acinetobacter iwoffi (textile isolate from Denmark). P.fluorescens was restreaked on Tryptone Soya Agar (TSA) (pH 7.3) (CM0131; Oxoid Ltd, Basingstoke, UK) and incubated for 1 day at 20° C. The strain was inoculated into 10 mL of TSB and the culture was incubated statically for 16 hours at 20° C. After propagation, the culture was diluted (1:100) in 400 ml M63 supplemented medium (15 mM $(NH_4)_2SO_4$, 100 mM $KH_2PO_4$, 1.8 µM, $FeSO_4$, 1 mM $MgSO_4.7H_2O$, 0.4% (w/v) glycerol, 0.2% (w/v) Casamino acids and 0.0001% (w/v) Thiamine), added to Corning® CellBIND® 225 cm² Angled Neck Cell Culture Flasks with Vent Cap (Product #3293) and incubated statically for 3 days at 20° C. The biofilm culture was subsequently pelleted by centrifugation (10 min, 8000 g, 25° C.), and the cells resuspended in 4 ml 3M NaCl and incubated for 30 min at 30° C. to extract the surface-associated EPS. The EPS-containing supernatant obtained after centrifugation (10 min, 5000 g, 25° C.) was then sterile filtered and stored at −20° C. until further.

The crude EPS extract from A.iwoffi was prepared as follows: 10 ml LB broth (L3152, Fluka) was inoculated and the culture was incubated for 2 day at 30° C. After propagation, the culture was diluted (1:100) in 300 ml fresh LB in a Corning® CellBIND® 225 cm² Angled Neck Cell Culture Flasks with Vent Cap (Product #3293) and incubated statically at 30° C. After 3 days, the culture was aliquoted into conical centrifuge tubes and the cells were pelleted by centrifugation (10 min, 6000 g, 25° C.). The pellets were then resuspended in a total of 1.5 ml 3M NaCl and incubated for 15 min at room temperature. The EPS-containing supernatant obtained after centrifugation (10 min, 6000 g, 25° C.) was sterile filtered and stored at −20° C. until use.

For wash performance testing, 50 ul aliquots of the different crude EPS extracts were spotted on sterile textile swatches (WFK20A) and incubated for 15 min at ambient temperature. The swatches (sterile or with EPS) were placed in 50 mL test tubes and 10 mL of wash liquor (15° dH water with 0.2 µg/L iron(III) oxide nano-powder (544884; Sigma-Aldrich) with 3.33 g/L liquid model A detergent) and 0.2 µg/ml or 2 µg/ml enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night.

The tristimulus light intensity (Y) values were measured using a DigiEYE colour measurement and imaging system (VeriVide) equipped with a Nikon D90 digital camera, and are displayed in table 8.

Delta values ($Y_{(swatches\ washed\ with\ enzyme)} - Y_{(swatches\ washed\ without\ enzyme)}$) are also indicated.

TABLE 8

Deep-cleaning effects of hexosaminidase in liquid model detergent on biofilm EPS from P. fluorescens and A. iwoffi

| Origin of EPS | Enzyme | Enzyme concentration (ppm) | Average Y values | ΔY |
|---|---|---|---|---|
| P. fluorescens | | 0 | 57.6 | |
| P. fluorescens | SEQ ID NO 35 | 0.2 | 72.6 | 14.9 |
| P. fluorescens | SEQ ID NO 35 | 2 | 78.7 | 21.1 |
| A. iwoffii | | 0 | 52.5 | |
| A. iwoffii | SEQ ID NO 35 | 0.2 | 60.0 | 7.5 |
| A. iwoffii | SEQ ID NO 35 | 2 | 58.0 | 5.5 |

The data clearly shows that the hexosaminidases also show deep-cleaning properties against EPS from gram-negative bacteria.

Example 9 Deep-Cleaning Effects of Hexosaminidase in Different Detergents

A crude extract of biofilm extracellular polymeric substances (EPS) were prepared from *S.aureus* (kind gift from Iñigo Lasa (Valle, J., A. Toledo-Arana, C. Berasain, J. M. Ghigo, B. Amorena, J. R. Penades, and I. Lasa. 2003, Mol. Microbiol. 48:1075-1087) as previously described in example 8.

Two circular swatches of 1 cm in diameter (20A wfk) were placed in each well of a 24 wells plate and spotted with 50 µl EPS from *S. aureus* for 10 min at RT. Swatches without EPS were included as controls. To each well was added one mechanical stress object (metal rod with plastic cover connected by rubbering); 975 µl of detergent solution (detergent and final concentration: Liquid model A detergent 3.33 g/L, Liquid model N detergent 2.0 g/L);

hexosaminidase in a final concentration of 5 mg/L; and 1000 µl soiled detergent with final concentration of 15 g/L rose clay facial mask purchased from www.saebevaerkstedet.dk. Swatches without PNAG and wells without enzyme was included as controls. The plate was shaken for 30 min at RT with repeating intervals of 30 sec at 1000 and 1200 rpm, respectively. All solutions were diluted in 15° dH water hardness. After washing the swatches were rinsed twice in water and dried on filter paper for a minimum of 2 hours or overnight. Dried swatches were fixed on a sheet of white paper for scanning and the color intensity (L) values were measured using the software Color Analyzer.

The tables 9 and 10 shows wash data for hexosaminidases in 2 different detergents Table 9 shows results in Model detergent A

| Enzyme | Enzyme concentration (ppm) | L values | ΔL (Lwith enzyme – Lwithout enzyme) |
|---|---|---|---|
| No Enzyme | 0 | 348 | 0 |
| SEQ ID NO 20 | 5 | 382 | 34 |
| SEQ ID NO 33 | 5 | 383 | 34 |
| SEQ ID NO 35 | 5 | 369 | 20 |
| SEQ ID NO 34 | 5 | 365 | 17 |
| SEQ ID NO 36 | 5 | 361 | 13 |

Table 10 Shows results in Model detergent N

| Enzyme | Enzyme concentration (ppm) | L values | ΔL (Lwith enzyme – Lwithout enzyme) |
|---|---|---|---|
| No Enzyme | 0 | 345 | 0 |
| SEQ ID NO 20 | 5 | 360 | 16 |
| SEQ ID NO 33 | 5 | 349 | 4 |
| SEQ ID NO 35 | 5 | 364 | 20 |
| SEQ ID NO 34 | 5 | 355 | 10 |
| SEQ ID NO 36 | 5 | 356 | 11 |

Example 10: Construction of Clades and Phylogenetic Trees

The Glyco_hydro_20 domain includes the polypeptides of the invention having PNAG activity and comprises the DSP domain as well as the clusters such as the clades.

A phylogenetic tree was constructed, of polypeptide sequences containing a Glyco_hydro_20 domain, as defined in PFAM (PF00728, Pfam version 31.0 Finn (2016). Nucleic Acids Research, Database Issue 44:D279-D285). The phylogenetic tree was constructed from a multiple alignment of mature polypeptide sequences containing at least one Glyco_hydro_20 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

The polypeptides containing a Glyco_hydro_20 domain comprises several motifs one example is GXDE (SEQ ID NO 41), situated in positions 277 to 278 in *Curtobacterium luteum* (SEQ ID NO 34). Residues D and E are the key catalytic residues of Glyco_hydro_20 enzymes (position 277 to 278 in SEQ ID NO 34).

As already described the polypeptides of the invention having PNAG activity may comprise the structural domains of Glyco_hydro_20.

The polypeptides may be separated into multiple distinct sub-clusters, or clades, where we denoted the clades listed below. The distinct motifs for each clade are described in details below.

Generation of IES Domain

A domain, preferably shared by the polypeptides of the invention, was identified. This domain has not been described previously. The domain is termed IES and polypeptides of this domain comprises Glyco_hydro_20 domain polypeptides of bacterial origin and are in addition to having PNAG activity, characterized by comprising certain motifs. The polypeptides of the domain comprise the motif example [EQ][NRSHA][YVFL][AGSTC][IVLF][EAQYN][SN] (SEQ ID NO 46), corresponding to QNVGIES at positions 156 to 162 of SEQ ID NO 34.

Generation of ARAY Clade

The ARAY clade comprises Glyco_hydro_20 domain polypeptides of bacterial origin, having PNAG activity. The polypeptides of the clade comprise the motif example ARAYYPV (SEQ ID NO 42), corresponding to pos 124 to 130 of SEQ ID NO 9, where Rat position 125 in SEQ ID NO 34 is part of the active site.

Another motif which may be comprised by the polypeptides of the ARAY clade is AWNDGID (SEQ ID NO 43), 306 to 312 in SEQ ID NO 34, where R (position 307 in SEQ ID NO 34) is part of the active site. A further motif which may be comprised by the polypeptides of the ARAY clade is DDQNVGI (SEQ ID NO 44), 154 to 160 in SEQ ID NO 34. An additional motif which may be comprised by the polypeptides of the ARAY clade is DPRIH (SEQ ID NO 45), 320 to 324 in SEQ ID NO 34.

An alignment of the polypeptides of the invention comprised in the clade is shown in FIG. 1.

A phylogenetic tree of the ARAY clade is shown in FIG. 2.

Example 11 Hmm Model

```
: The GH20 Catalytic Domain HMM
HMMER3/f [3.1b2 | February 2015]
NAME  GH20
LENG  349
ALPH  amino
RF    no
MM    no
CONS  yes
CS    no
MAP   yes
DATE  Tue Apr 19 15:50:13 2016
NSEQ  7
EFFN  0.721191
CKSUM 975545072
STATS LOCAL MSV      -11.4545  0.70012
STATS LOCAL VITERBI  -11.9986  0.70012
STATS LOCAL FORWARD   -5.4957  0.70012
HMM         A        C        D        E        F        G        H        I        K        L        M        N
            P        Q        R        S        T        V        W        Y
            m->m     m->i     m->d     i->m     i->i     d->m     d->d
COMPO   2.60174  4.67169  2.79327  2.61588  3.29203  2.91852  3.66283  2.75216
        2.66516  2.45487  3.74224  2.89789  3.53715  3.04900  3.06221  2.65049  2.86470  2.72758
        4.38456  3.25755
        2.68614  4.42170  2.77513  2.73135  3.46347  2.40530  3.72523  3.29326  2.67755
        2.69351  4.24655  2.90337  2.73753  3.18095  2.89809  2.37893  2.77513  2.98527  4.58506
        3.61494
        0.45793  1.55220  1.86030  1.93584  0.15584  0.00000        *
     1  2.62542  4.83427  2.82121  2.16711  4.08650  3.36627  3.59200  3.50267  2.32909
        3.09104  3.28010  2.61805  3.79033  2.27737  2.74111  2.64445  2.85824  3.17885  5.31504
        3.98423     18 e - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.03160  3.86615  4.58850  0.61958  0.77255  0.63100  0.75941
     2  2.59520  4.80934  2.56843  2.35720  4.04573  3.35360  3.12363  3.48055  2.19222
        2.71416  3.89420  2.88005  3.77532  2.74381  2.81030  2.39844  2.83053  3.15335  5.29560
        3.95248     19 k - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.03160  3.86615  4.58850  0.61958  0.77255  0.63100  0.75941
     3  2.44337  4.24133  3.44826  2.94557  3.60875  3.32170  3.90746  2.74241  2.86666
        2.33269  3.55471  3.28416  3.84623  3.20748  3.20284  2.11243  2.42884  2.23327  5.07294
        3.82985     20 s - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.03160  3.86615  4.58850  0.61958  0.77255  0.40460  1.10034
     4  2.32383  4.74064  2.88292  2.47855  4.20972  3.29447  3.71653  3.63312  2.49182
        3.22640  4.04628  2.96533  3.15174  1.88659  2.91020  2.35619  2.87019  3.25803  5.44415
        4.11846     21 q - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.02689  4.02509  4.74744  0.61958  0.77255  0.48576  0.95510
     5  2.60305  4.92460  2.34604  2.33546  4.20764  3.36563  3.59784  3.20833  2.23451
        3.20814  3.99952  2.60210  3.26130  2.72857  2.85746  2.60147  2.59997  3.28261  5.41136
        4.04410     22 k - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.02689  4.02509  4.74744  0.61958  0.77255  0.48576  0.95510
     6  2.96397  5.16780  3.08807  2.61611  4.55299  3.55911  3.63937  3.95530  1.33438
        3.42043  4.28125  3.07821  3.97783  2.08646  2.29309  2.94591  3.16238  3.61961  5.49982
        4.25880     23 k - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.02689  4.02509  4.74744  0.61958  0.77255  0.48576  0.95510
     7  2.87810  5.26730  2.45384  1.39315  4.56042  3.33537  3.71463  4.03551  2.48787
        3.54742  4.39801  2.82640  3.87420  2.18876  2.91430  2.81748  3.13497  3.66128  5.70116
        4.30753     24 e - - -
        2.68618  4.42225  2.77519  2.73123  3.46354  2.40513  3.72494  3.29354  2.67741
        2.69355  4.24690  2.90347  2.73739  3.18146  2.89801  2.37887  2.77519  2.98518  4.58477
        3.61503
        0.02689  4.02509  4.74744  0.61958  0.77255  0.48576  0.95510
     8  2.31131  4.64341  3.00787  2.53623  4.11949  2.84873  3.72249  3.52885  2.04434
        3.14224  3.96200  3.00481  3.78934  2.88956  2.92616  2.36328  2.26473  3.16299  5.37868
        4.06985     25 k - - -
```

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
9 2.86527 4.62317 3.57011 3.49011 4.62505 0.52816 4.59887 4.26391 3.69199
3.89823 4.87687 3.73474 4.01908 4.00427 3.90917 3.04194 3.35840 3.76278 5.67765
4.73288 26 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
10 3.27661 4.60563 4.81638 4.28979 3.17506 4.53343 4.88108 1.60763 4.11630
1.03186 2.99695 4.54933 4.75580 4.30643 4.26407 3.90698 3.51388 2.04894 5.23833
4.09917 27 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
11 2.23703 4.27706 3.59749 3.09133 3.59810 3.42501 4.01297 2.70077 3.00197
2.52770 2.56062 3.41118 3.94133 3.33484 3.32008 2.76392 1.85004 2.48383 5.10447
3.88249 28 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
12 3.27661 4.60563 4.81638 4.28979 3.17506 4.53343 4.88108 1.60763 4.11630
1.03186 2.99695 4.54933 4.75580 4.30643 4.26407 3.90698 3.51388 2.04894 5.23833
4.09917 29 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
13 3.15998 5.30397 0.72157 2.44238 4.70300 3.33206 4.07440 4.32728 3.18878
3.90937 4.89317 3.00552 3.99587 3.31546 3.72392 3.10675 3.50263 3.95099 5.84132
4.55374 30 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
14 2.89299 4.37089 4.29165 3.84509 3.55549 3.98375 4.62445 1.14199 3.69578
2.18331 3.42439 4.07889 4.43466 4.03173 3.92165 3.38134 2.66753 1.83054 5.36349
4.14337 31 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
15 1.21141 4.16247 3.48581 3.20999 4.27083 2.95735 4.25932 3.61453 3.25267
3.36905 4.22177 3.34067 3.71129 3.54606 3.54832 1.72877 2.72467 3.10484 5.63933
4.42397 32 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
16 3.18427 5.00812 3.69114 3.17333 4.40169 3.63992 3.94487 3.95597 2.31269
3.44427 4.44251 3.52033 4.13693 3.15941 0.76856 3.26233 3.44101 3.67383 5.42399
4.29809 33 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
17 2.91802 5.11009 3.26657 2.65260 4.45768 3.59624 2.28209 3.87264 1.65036
3.34797 4.18853 3.10273 3.96804 2.73579 1.89425 2.91169 3.10260 3.54063 5.42158
4.18113 34 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
18 3.60906 4.85790 4.61301 4.29200 1.07612 4.37531 3.49533 3.27851 4.13915
2.61105 3.87947 4.07109 4.68672 4.11993 4.17923 3.74459 3.83280 3.21007 3.64011
1.42609 35 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
19 3.47415 4.90106 4.06661 3.82674 2.31411 4.01031 3.69985 3.46280 3.67999
2.87675 4.12240 3.91595 4.48161 3.94901 3.83146 3.59477 3.76213 3.34085 3.96297
0.74537 36 y - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
20 2.32198 4.30679 3.25189 2.89710 4.22510 3.05357 4.03256 3.63023 2.93492
3.29831 4.12849 3.19386 2.11014 3.26010 3.30004 1.65444 2.37000 3.15702 5.54568
4.29162 37 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
21 2.66597 4.22511 3.91716 3.37375 3.43772 3.72193 4.15633 1.85319 3.28493
2.33346 3.36759 3.67002 3.26998 3.57237 3.55940 3.03288 2.59141 1.64956 5.01744
3.80727 38 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
22 2.82044 5.34850 2.13403 1.52422 4.64944 3.28466 3.68463 4.14292 2.24269
3.63308 4.43539 2.42022 3.82375 2.82399 3.08185 2.73861 3.07900 3.72182 5.78514
4.33259 39 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
23 2.56043 4.26125 3.87113 3.43769 3.72631 3.45624 4.31955 2.39581 3.33689
2.55074 3.63922 3.64954 4.05083 3.66947 3.61016 2.86041 1.73397 1.58618 5.33176
4.10720 40 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
24 3.22367 4.54297 4.81042 4.29477 3.28052 4.51488 4.91059 1.22931 4.12691
1.39564 3.11095 4.54183 4.76195 4.35034 4.28848 3.89419 3.46866 1.87895 5.31062
4.13865 41 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
25 3.11697 5.08145 3.30276 2.89877 4.50288 3.58722 3.85206 3.94235 0.84697
3.47537 4.43095 3.31562 4.07873 3.03659 2.47177 3.15035 3.36006 3.64238 5.49660
4.33243 42 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
26 2.13272 4.90400 2.43559 2.34272 4.27641 3.30690 3.67133 3.71686 2.49641
3.28917 4.09511 2.87194 3.79353 2.33192 2.97421 2.15688 2.89582 3.34042 5.49710
4.12889 43 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
27 3.16649 4.52728 4.63396 4.13742 1.55523 4.29617 4.32301 1.73842 4.00286
1.76408 3.11947 4.27581 4.58882 4.13968 4.13035 3.65327 3.40793 2.23962 4.62924
3.16052 44 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
28 3.11618 4.44875 4.77519 4.29382 3.52475 4.41912 5.00622 1.05857 4.16245
2.01027 3.34073 4.51329 4.74777 4.43442 4.35709 3.81802 3.38913 1.49499 5.51169
4.30526 45 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
29 3.15998 5.30397 0.72157 2.44238 4.70300 3.33206 4.07440 4.32728 3.18878
3.90937 4.89317 3.00552 3.99587 3.31546 3.72392 3.10675 3.50263 3.95099 5.84132
4.55374 46 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
30 2.67413 4.78076 2.75214 1.93151 4.20765 3.30969 3.79991 3.51271 2.62236
3.21069 4.09287 2.98239 3.85595 2.98671 3.03254 2.72726 1.69281 3.18792 5.49375
4.17123 47 t - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
31 3.15114 4.53079 4.54737 4.17094 3.48096 4.22724 4.87288 0.90672 4.00200
2.03850 3.39535 4.39520 4.64605 4.33611 4.18143 3.73942 3.44853 1.86187 5.40162
4.15144 48 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
32 2.27518 4.59840 2.98273 2.59620 4.01461 3.27359 2.35884 3.51023 2.60535
3.13774 3.98239 3.04442 3.81201 2.98424 3.00023 1.88039 2.86191 3.15155 5.33302
3.99996 49 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
33 2.20797 4.82901 2.95598 2.43130 4.08188 3.41762 3.17477 3.49920 2.19484
2.78090 3.90630 2.64872 3.81741 2.54863 2.77108 2.65181 2.85410 3.17381 5.31346
3.98688 50 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
34 1.72399 4.44652 3.01228 2.70067 4.25777 3.10875 3.93504 3.68015 2.82445
3.32584 4.14997 2.16806 3.75134 3.13888 3.22977 1.96545 2.80720 3.22507 5.55414
4.26228 51 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
35 2.86527 4.62317 3.57011 3.49011 4.62505 0.52816 4.59887 4.26391 3.69199
3.89823 4.87687 3.73474 4.01908 4.00427 3.90917 3.04194 3.35840 3.76278 5.67765
4.73288 52 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
36 2.86527 4.62317 3.57011 3.49011 4.62505 0.52816 4.59887 4.26391 3.69199
3.89823 4.87687 3.73474 4.01908 4.00427 3.90917 3.04194 3.35840 3.76278 5.67765
4.73288 53 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
37 2.70697 5.04010 1.97763 2.27126 4.43079 3.26888 3.71680 3.88291 2.60077
3.45129 4.26710 2.22267 3.80974 2.87048 3.10900 2.68588 2.10398 3.48789 5.64569
4.24126 54 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
38 3.60906 4.85790 4.61301 4.29200 1.07612 4.37531 3.49533 3.27851 4.13915
2.61105 3.87947 4.07109 4.68672 4.11993 4.17923 3.74459 3.83280 3.21007 3.64011
1.42609 55 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
39 3.33002 4.74841 4.43394 4.07687 3.19997 4.17458 4.68490 2.41486 3.84312
0.70779 3.17954 4.33748 4.58523 4.17477 3.99325 3.76683 3.61819 2.49136 5.13215
3.88991 56 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
40 2.87113 5.02265 2.89430 2.54183 3.92175 3.47916 1.83985 3.76451 2.31828
3.27943 4.16746 3.02970 3.94298 2.13713 2.63327 2.87433 3.10615 3.44925 5.22235
3.79305 57 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
41 3.33002 4.74841 4.43394 4.07687 3.19997 4.17458 4.68490 2.41486 3.84312
0.70779 3.17954 4.33748 4.58523 4.17477 3.99325 3.76683 3.61819 2.49136 5.13215
3.88991 58 l - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
42 3.17489 4.96114 3.28685 3.06447 3.40116 3.58476 0.85747 3.90143 2.90380
3.37516 4.43190 3.46668 4.14687 3.43336 3.15915 3.24489 3.48443 3.63377 4.86369
3.34821 59 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
43 3.45825 4.81603 4.44812 4.19374 0.79153 4.10787 3.95340 2.96558 4.09750
2.30148 3.67455 4.19402 4.56467 4.22394 4.17942 3.71886 3.76029 2.96711 4.16127
2.51081 60 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
44 2.39611 4.31724 3.34558 3.17089 4.23153 3.04461 4.27530 3.77599 3.25503
3.48527 4.40012 3.36943 3.79653 3.59279 3.53464 0.88216 2.88812 3.27739 5.59224
4.31654 61 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
45 3.15998 5.30397 0.72157 2.44238 4.70300 3.33206 4.07440 4.32728 3.18878
3.90937 4.89317 3.00552 3.99587 3.31546 3.72392 3.10675 3.50263 3.95099 5.84132
4.55374 62 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
46 2.82433 4.98743 2.72626 2.47424 3.84772 3.39017 1.79546 3.80387 2.51314
3.34581 4.22739 2.14774 3.91198 2.95173 2.88393 2.82843 3.09659 3.46249 5.21617
3.73245 63 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
47 3.09089 5.22592 2.56202 0.82634 4.59241 3.37774 3.98099 4.07700 2.88130
3.67069 4.64056 3.02951 3.99035 3.19510 3.30408 3.05927 3.39713 3.74605 5.73522
4.46059 64 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
48 2.66333 4.85194 2.82911 2.47306 4.29809 3.32358 3.71334 3.75949 2.41795
3.32573 4.15172 1.76097 3.83522 2.87346 2.41981 2.34515 2.95006 3.37838 5.48902
4.15662 65 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
49 3.47415 4.90106 4.06661 3.82674 2.31411 4.01031 3.69985 3.46280 3.67999
2.87675 4.12240 3.91595 4.48161 3.94901 3.83146 3.59477 3.76213 3.34085 3.96297
0.74537 66 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
50 0.81435 4.27445 3.62315 3.42433 4.20975 3.09435 4.42756 3.35852 3.44466
3.23284 4.24993 3.53357 3.84826 3.77227 3.68299 2.62446 2.91253 2.98636 5.62159
4.43962 67 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
51 3.25587 4.57778 4.82700 4.30157 3.21221 4.53220 4.89700 1.44546 4.13392
1.15442 3.03350 4.55420 4.75994 4.32908 4.28372 3.90604 3.49491 1.97962 5.26452
4.11932 68 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
52 2.03769 4.92952 2.57987 1.46106 4.37380 3.28153 3.79326 3.70661 2.65006
3.37321 4.24554 2.90322 3.84882 2.96755 3.10005 2.73885 3.03061 3.35463 5.62496
4.26393 69 e - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
53 2.39611 4.31724 3.34558 3.17089 4.23153 3.04461 4.27530 3.77599 3.25503
3.48527 4.40012 3.36943 3.79653 3.59279 3.53464 0.88216 2.88812 3.27739 5.59224
4.31654 70 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
54 2.65102 4.90823 2.76780 1.98616 4.19563 3.36273 2.75116 3.63175 2.42514
3.20954 4.02330 2.89383 3.81175 2.79138 2.87317 2.43615 2.37119 3.28393 5.41942
4.06591 71 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
55 2.80253 4.22179 4.31017 3.74307 2.20561 3.92303 4.06161 2.16322 3.61262
1.81545 3.11713 3.90030 4.25514 3.78488 3.75700 3.22501 3.03186 2.06234 4.53432
2.46480 72 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
56 3.33002 4.74841 4.43394 4.07687 3.19997 4.17458 4.68490 2.41486 3.84312
0.70779 3.17954 4.33748 4.58523 4.17477 3.99325 3.76683 3.61819 2.49136 5.13215
3.88991 73 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
57 2.82752 5.31584 2.08949 1.97162 4.63397 2.31340 3.71862 4.12629 2.64864
3.63806 4.45421 1.91931 3.82675 2.86930 3.19982 2.75097 3.10082 3.71075 5.80956
4.35188 74 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
58 3.01009 4.99534 3.01191 2.77152 4.18365 3.47191 3.93031 3.84023 2.58229
3.32714 4.35311 3.23169 4.02910 0.98524 2.86243 3.05251 3.30807 3.56112 5.42967
4.13451 75 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
59 2.76322 4.88423 3.14125 2.60350 4.14363 3.49723 3.64782 3.58659 2.20103
2.76990 4.01628 2.32855 3.90954 2.80978 1.76364 2.79935 2.98927 3.27553 5.32057
4.02555 76 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
60 1.88301 4.70754 2.77889 2.04292 4.23171 2.70975 3.76605 3.65306 2.62652
3.26332 4.08493 2.94632 3.78772 2.93801 3.08209 2.29057 2.87475 3.26489 5.49618
4.16190 77 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
61 2.12998 4.95682 2.55707 1.40093 4.39593 3.28197 3.79449 3.73028 2.65304
3.39386 4.26878 2.89522 3.85234 2.96839 3.10479 2.74883 3.04574 3.37772 5.64282
4.27718 78 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
62 2.87132 5.23258 2.02114 2.22822 4.58008 3.23965 3.81527 4.14555 2.79632
3.70120 4.56321 1.32198 3.86081 2.99894 3.32852 2.81489 3.18464 3.73193 5.81429
4.36009 79 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
63 1.26091 4.25315 3.38399 3.08468 4.20504 3.04239 4.17235 3.52109 3.12261
3.26340 4.14811 3.30699 2.21225 3.44135 3.44300 2.49769 2.78295 3.07867 5.56731
4.34523 80 a - - -

2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.19054 4.02509 1.86030 0.61958 0.77255 0.48576 0.95510
64 2.63710 4.26471 3.83287 3.32297 3.52352 3.62954 4.20457 1.98169 3.21852
2.29057 3.41590 3.62719 4.10629 3.54798 3.51624 2.97480 2.00441 1.82363 5.16958
3.94507 81 v - - -
2.68621 4.42228 2.77522 2.73126 3.46357 2.40516 3.72497 3.29357 2.67744
2.69358 4.24693 2.90350 2.73742 3.18125 2.89766 2.37890 2.77522 2.98521 4.58480
3.61506
0.30705 1.36957 4.58850 0.25181 1.50235 0.63100 0.75941
65 2.64016 4.96447 2.26629 2.06144 4.25840 2.81506 3.61637 3.69941 2.46807
3.26998 4.08149 2.48330 3.75866 2.76465 2.96551 2.62345 2.89483 2.89292 5.48085
4.09568 83 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
66 2.32512 4.76066 2.99914 2.60494 4.22816 3.34939 3.69714 3.52706 1.48205
3.17750 4.07526 3.04563 3.85645 2.86989 2.53074 2.75769 2.98044 3.20786 5.39552
4.13466 84 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
67 2.69811 4.98517 1.85769 2.24050 4.02912 3.27664 3.63332 3.69170 2.54094
3.26778 4.11119 2.47116 3.78689 2.81989 3.03591 2.67839 2.95708 3.34690 5.35319
3.03969 85 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
68 2.65708 4.43313 3.32956 3.22817 4.37057 0.73893 4.34882 3.96866 3.40858
3.62358 4.59928 3.49387 3.82406 3.73324 3.64531 2.82881 3.13782 3.49820 5.46738
4.47226 86 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
69 2.71555 4.26084 4.01045 3.49314 3.50176 3.78219 4.32824 1.82828 3.38934
2.22742 3.37809 3.78266 4.22210 3.70242 3.66847 3.12550 2.31069 1.54261 5.19718
3.98072 87 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
70 3.23798 4.72953 3.82891 3.55712 2.29361 3.82278 3.61560 3.24807 3.41482
2.70363 3.92376 3.71568 4.29677 3.72237 3.59982 3.37530 3.52463 3.11833 3.93713
0.97636 88 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
71 2.87230 4.31165 4.19157 3.65625 2.39581 3.95642 3.98324 1.69315 3.53508
1.94049 3.15076 3.85549 4.28439 3.73693 3.72476 3.26422 3.10466 2.25034 4.42927
2.55852 89 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
72 2.71820 4.71455 2.70482 2.58966 4.07708 3.17974 3.91591 3.78610 2.81907
3.43368 4.38897 1.16929 3.83129 3.18866 3.17352 2.78563 3.09985 3.40895 5.38372
4.02587 90 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
73 2.74311 4.50151 3.34959 3.18771 4.18344 3.18938 4.26569 3.72722 3.24447
3.35475 4.40432 3.49505 0.83946 3.63344 3.49072 2.91040 3.18417 3.37332 5.37173
4.30402 91 p - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
74 2.57998 4.49024 3.18601 2.64336 3.65510 3.45032 3.68065 3.00658 2.10954
2.70983 3.60157 3.09739 3.85237 2.91430 2.85071 2.70990 2.56455 2.49907 5.03209
3.15736 92 k - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
75 2.40932 4.25438 3.42249 3.17420 3.96330 3.09387 4.19201 3.08966 3.11705
2.95338 4.00431 3.38459 3.79712 3.51219 3.37604 2.61052 1.18267 2.78532 5.40166
4.17993 93 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.40460 1.10034
76 2.70229 4.94580 2.62102 2.36264 4.26419 2.44373 2.95596 3.81010 2.54731
3.37338 4.20279 1.83844 3.83055 2.89237 2.99078 2.70546 2.98733 3.43091 5.51220
4.12097 94 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
77 2.73064 4.86893 2.99005 2.58925 4.35918 3.38261 3.72140 3.77606 1.45572
3.34226 4.18943 3.04768 3.88536 2.88118 2.59856 2.08548 3.01111 3.40813 5.48642
4.20070 95 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
78 1.98628 4.26405 3.34273 3.00228 4.17542 3.05695 4.09779 3.47602 3.01866
3.21897 4.08702 3.25826 1.66206 3.34795 3.35647 2.48647 2.28667 3.04559 5.53327
4.29925 96 p - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
79 3.60906 4.85790 4.61301 4.29200 1.07612 4.37531 3.49533 3.27851 4.13915
2.61105 3.87947 4.07109 4.68672 4.11993 4.17923 3.74459 3.83280 3.21007 3.64011
1.42609 97 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
80 3.33002 4.74841 4.43394 4.07687 3.19997 4.17458 4.68490 2.41486 3.84312
0.70779 3.17954 4.33748 4.58523 4.17477 3.99325 3.76683 3.61819 2.49136 5.13215
3.88991 98 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
81 2.28585 4.22285 3.40606 3.08808 4.19721 3.01742 4.15603 3.54303 3.09540
3.28360 4.14309 3.29427 3.73505 3.42322 3.41193 1.62744 1.55290 3.07900 5.55939
4.32472 99 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
82 2.80548 4.54103 3.51754 2.99292 2.48793 3.69083 3.65985 3.04567 2.18102
2.65617 3.63318 3.36147 4.06968 3.21180 3.16262 2.96440 3.03488 2.83807 4.39569
1.87581 100 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
83 2.46104 5.05388 3.00611 2.26593 4.40780 3.48091 3.60489 3.80877 1.58818
3.32066 4.13656 2.98553 3.88379 2.73457 2.24172 2.77136 2.99409 3.45542 5.45676
4.16445 101 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
84 2.86785 5.21525 2.54398 1.83107 4.51410 3.36448 3.70136 3.97862 2.41801
3.49251 4.34395 2.86427 3.88267 1.65279 2.81169 2.82002 3.11732 3.61462 5.64287
4.27431 102 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
85 3.30073 4.65702 4.74385 4.22920 3.12452 4.49680 4.82353 1.90464 4.02827
0.88495 2.96754 4.50096 4.73304 4.24343 4.18267 3.87892 3.54126 2.17263 5.19002
4.02959 103 l - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
86 2.65877 4.99581 2.47013 2.14619 4.26940 3.35960 3.61847 3.71008 2.20644
2.53460 4.06683 2.40169 3.79985 2.75424 2.87825 2.64487 2.89639 3.34825 5.46578
4.09240 104 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
87 2.83807 5.33618 1.69859 1.78951 4.65491 3.25658 3.72510 4.14887 2.66491
3.66171 4.48056 2.73333 3.82881 2.87694 3.22207 2.07820 3.11390 3.73051 5.83102
4.36614 105 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
88 3.22367 4.54297 4.81042 4.29477 3.28052 4.51488 4.91059 1.22931 4.12691
1.39564 3.11095 4.54183 4.76195 4.35034 4.28848 3.89419 3.46866 1.87895 5.31062
4.13865 106 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
89 2.67869 4.42348 3.47794 2.94624 3.62577 3.60203 3.89183 1.84663 2.22721
2.56504 3.54443 3.34835 4.01262 3.17151 3.02552 2.89929 2.56473 2.44088 5.08673
3.85005 107 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
90 1.82839 4.62244 2.58343 2.54313 3.77433 3.38531 3.72959 3.25100 2.63974
2.92527 3.79709 3.02891 3.85128 2.95691 3.07254 2.69815 2.87475 2.96579 5.15933
2.82327 108 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
91 3.47415 4.90106 4.06661 3.82674 2.31411 4.01031 3.69985 3.46280 3.67999
2.87675 4.12240 3.91595 4.48161 3.94901 3.83146 3.59477 3.76213 3.34085 3.96297
0.74537 109 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
92 1.21141 4.16247 3.48581 3.20999 4.27083 2.95735 4.25932 3.61453 3.25267
3.36905 4.22177 3.34067 3.71129 3.54606 3.54832 1.72877 2.72467 3.10484 5.63933
4.42397 110 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
93 2.86665 5.10493 2.84216 2.49547 4.48992 3.44045 3.67909 3.93633 1.41713
3.44879 4.29421 2.18473 3.91870 2.82764 2.52526 2.85172 3.10667 3.57413 5.54267
4.24105 111 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
94 2.43678 5.18726 1.97399 2.03436 4.50995 3.28744 3.67198 3.98616 2.54413
3.50748 4.30465 2.43356 3.80476 2.81062 3.07138 2.19673 3.00070 3.57938 5.68251
4.25373 112 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
95 3.08499 5.19289 3.51099 2.82787 4.65937 3.69242 3.62259 4.00128 1.31465
3.43365 4.30648 3.22313 4.05699 2.75656 1.52521 3.07826 3.24642 3.68364 5.46575
4.30730 113 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
96 2.80542 5.19687 2.02773 2.20857 4.61825 2.67418 3.77417 4.12310 2.73202
3.65759 4.48827 1.55432 3.83044 2.93961 3.27520 2.75334 3.11040 3.69515 5.82269
4.37736 114 n - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
97 3.11613 4.44968 4.77262 4.29194 3.52300 4.41684 5.00429 1.05559 4.15968
2.00856 3.33974 4.51143 4.74646 4.43229 4.35428 3.81617 3.38941 1.50231 5.51006
4.30319 115 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
98 2.72273 4.76136 2.94932 1.67024 3.90234 3.46579 3.76456 3.18245 2.56433
2.81297 2.60535 3.06133 3.91515 2.95853 2.96031 2.79620 2.97154 2.95873 5.29546
3.98620 116 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
99 3.16163 4.49254 4.76914 4.22636 3.29555 4.45874 4.86010 1.76060 4.10085
1.23526 3.10116 4.47633 4.70773 4.29372 4.27087 3.81174 3.40261 1.51980 5.29741
4.16378 117 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
100 3.11130 4.42474 4.82205 4.32945 3.57088 4.45888 5.04233 1.20522
4.21559 2.06591 3.37517 4.54602 4.77150 4.47909 4.41151 3.85036 3.37865 1.25185
5.54730 4.34363 118 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
101 2.96585 4.69526 3.58992 3.45271 4.43091 3.37425 4.51572 4.01796
3.52354 3.62729 4.68520 3.74295 0.58713 3.90765 3.74983 3.13863 3.41988 3.64553
5.57332 4.55440 119 P - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
102 2.96406 5.52572 1.67512 1.28150 4.81416 3.24219 3.78335 4.33080
2.79447 3.83502 4.68921 2.70807 3.86182 2.94974 3.38467 2.84856 3.25200 3.90619
5.98418 4.48605 120 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
103 3.13982 4.44529 4.83263 4.29726 3.40582 4.49343 4.93951 1.48570
4.18488 1.54415 3.20710 4.52934 4.74725 4.39010 4.35704 3.85324 3.38440 1.35670
5.38804 4.23484 121 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
104 3.15998 5.30397 0.72157 2.44238 4.70300 3.33206 4.07440 4.32728
3.18878 3.90937 4.89317 3.00552 3.99587 3.31546 3.72392 3.10675 3.50263 3.95099
5.84132 4.55374 122 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
105 2.47570 4.32120 3.41534 2.95632 3.73107 3.30775 3.95200 2.98811
2.88215 2.10158 3.69589 3.29288 3.86540 3.23896 3.21708 1.75645 2.49035 2.71766
5.17536 3.91851 123 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
106 2.96585 4.69526 3.58992 3.45271 4.43091 3.37425 4.51572 4.01796
3.52354 3.62729 4.68520 3.74295 0.58713 3.90765 3.74983 3.13863 3.41988 3.64553
5.57332 4.55440 124 P - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
107 1.85721 4.55854 2.85901 2.64278 4.28840 3.14642 3.94666 3.69016
2.83077 3.38284 4.24500 1.57103 3.79755 3.15922 3.22584 2.60808 2.90624 3.26550
5.59505 4.27125 125 n - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
108 3.17489 4.96114 3.28685 3.06447 3.40116 3.58476 0.85747 3.90143
2.90380 3.37516 4.43190 3.46668 4.14687 3.43336 3.15915 3.24489 3.48443 3.63377
4.86369 3.34821 126 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
109 2.54708 4.30603 3.56761 3.11842 3.54148 3.40565 4.01831 2.82517
2.99881 2.51286 1.82933 3.42092 3.94676 3.36376 3.29058 2.09180 2.88069 2.61684
5.06929 3.80793 127 m - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
110 2.71423 4.78247 3.16282 2.63537 4.14187 3.46292 3.68040 3.50746
2.03512 3.11264 3.96760 3.08828 3.89674 2.84833 2.27234 2.77509 1.81528 3.19654
5.32878 4.06891 128 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
111 1.37678 4.16990 3.47143 3.15263 4.25712 1.99759 4.20963 3.60472
3.19472 3.33701 4.17373 3.31367 3.70623 3.48136 3.51256 2.41500 2.27599 3.09969
5.61177 4.40326 129 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
112 2.91787 4.35079 4.31360 3.77834 2.88033 3.98633 4.10805 1.47498
3.56553 2.00482 3.21189 3.95307 4.33627 3.82542 3.72767 3.32584 3.15861 2.29746
2.60881 3.14763 130 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
113 3.32075 4.67106 4.65248 4.18787 1.42808 4.36915 4.17707 2.44930
4.03693 1.35663 3.11212 4.29060 4.64318 4.14491 4.14864 3.74047 3.55563 2.53074
4.41270 2.86475 131 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
114 2.66073 5.07937 2.26031 2.28403 4.39463 3.34789 3.60201 3.85527
2.18826 3.37229 4.15086 2.30124 3.78910 2.72353 2.59107 2.62894 2.61999 3.45846
5.53515 4.14389 132 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
115 3.27661 4.60563 4.81638 4.28979 3.17506 4.53343 4.88108 1.60763
4.11630 1.03186 2.99695 4.54933 4.75580 4.30643 4.26407 3.90698 3.51388 2.04894
5.23833 4.09917 133 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
116 3.18836 4.56014 4.67858 4.11504 3.12109 4.40005 4.72037 2.14883
3.97244 1.10732 2.12990 4.38679 4.63146 4.13770 4.13124 3.73504 3.41689 1.97706
5.13923 4.05041 134 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
117 2.73946 5.10568 2.75550 1.85563 4.43286 3.39812 3.61445 3.86814
1.90313 3.37982 4.17993 2.88391 3.83738 2.46628 2.67483 2.70967 2.65657 3.49090
5.52943 4.17806 135 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
118 2.26057 4.88016 2.89797 2.03946 4.15763 3.41225 3.63010 3.54479
2.01125 2.81671 3.97038 2.94046 3.83099 2.77760 2.75755 2.67920 2.89372 3.21779
5.37090 4.04307 136 k - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
119 2.73194 5.17244 2.36766 2.07445 4.48588 3.35243 3.05785 3.95237
1.72160 3.45174 4.23972 2.82417 3.81517 2.74655 2.81056 2.68500 2.96930 3.55265
5.59666 4.20411 137 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
120 2.70692 5.07134 2.20922 2.33678 4.33648 3.38047 2.76322 3.83446
2.32985 3.35441 4.15259 2.87232 3.82189 2.74764 2.08040 2.68121 2.94146 3.45631
5.48854 4.10941 138 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
121 2.28383 4.25259 3.23331 3.03121 4.40948 1.54264 4.21451 3.88421
3.19676 3.54852 4.37163 3.25256 3.71581 3.47652 3.52832 1.53475 2.77442 3.29961
5.72416 4.48793 139 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
122 2.62670 4.71872 3.04803 2.57995 4.12542 2.45687 3.71580 3.48454
1.72319 3.12639 3.97514 3.04494 3.84872 2.88662 2.76011 2.69224 2.90242 2.73030
5.36328 4.07138 140 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
123 2.63671 4.94741 2.34491 2.17813 4.21572 3.36577 3.61482 3.64916
2.23177 2.53478 4.01943 2.86706 3.18257 2.75230 2.87923 2.63249 2.87359 3.29527
5.42737 4.06118 141 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
124 3.59200 4.88189 4.49524 4.16753 1.72141 4.33085 3.49196 3.32239
4.02300 2.67191 3.93511 4.01871 4.65923 4.05817 4.10592 3.70493 3.82201 3.24078
3.65279 0.91520 142 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
125 2.71495 4.30385 3.95717 3.43967 3.52461 3.73632 4.27384 2.20561
3.32711 2.07872 3.42685 3.73220 4.19239 3.64722 3.60799 3.07686 2.00598 1.60679
5.17470 3.95543 143 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
126 2.74811 5.23021 2.03597 2.22845 4.54525 3.32170 3.63837 4.02450
2.05939 3.51749 4.30407 2.49091 3.81017 2.21990 2.91368 2.68889 2.99363 3.61117
5.66339 4.24548 144 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.19054 4.02509 1.86030 0.61958 0.77255 0.48576 0.95510
127 2.71622 4.93032 2.91837 2.44757 4.27024 2.56128 3.58138 3.67599
1.97586 3.21555 4.04364 2.94106 3.83300 2.39687 2.25860 2.72275 2.94038 3.33632
5.37783 4.08673 145 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.40460 1.10034
128 3.25623 4.57823 4.82697 4.30148 3.21152 4.53230 4.89679 1.44812
4.13378 1.15209 3.03278 4.55421 4.75989 4.32875 4.28350 3.90611 3.49523 1.98079
5.26405 4.11904 146 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
129 2.76965 4.81252 3.27318 2.67726 4.10048 3.54325 3.66039 3.41986
1.63425 3.04914 3.92375 3.12545 3.93359 2.82771 2.22017 2.83233 2.98598 2.37446
5.28619 4.03751 147 k - - -

-continued

```
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
130 2.27947 4.22349 3.39397 3.08701 4.23309 3.00493 4.16780 3.59064
3.10392 3.32390 4.17920 3.29014 3.72924 3.42991 3.42118 1.32616 1.91464 3.10928
5.58890 4.35270 148 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
131 2.67579 5.08486 2.23936 2.31120 4.41131 3.36717 3.59815 3.86701
1.87336 3.37634 4.15705 2.85162 3.23771 2.71846 2.50489 2.64496 2.91032 3.47145
5.52830 4.15033 149 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
132 2.74928 4.33772 3.77022 3.21659 2.76784 3.72972 3.73047 2.81034
3.08105 2.44844 2.93599 3.50889 4.09464 2.86730 3.35124 3.00321 2.97780 2.62097
3.26940 1.87300 150 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
133 2.50678 4.38589 3.29084 2.76381 3.69713 3.38207 3.80528 2.69232
2.72769 2.74801 3.62662 2.82365 3.85080 3.06040 3.11393 2.01338 2.48850 2.46781
5.09617 3.83707 151 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
134 2.49533 5.39227 1.51489 1.70195 4.70218 3.24989 3.74391 4.18282
2.71006 3.70710 4.53879 2.72149 3.83890 2.90065 3.28002 2.78565 3.15621 3.76799
5.88297 4.40554 152 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
135 2.97307 5.54957 1.50577 1.39709 4.83553 3.23796 3.78637 4.35667
2.80824 3.85643 4.71221 2.70112 3.86230 2.95346 3.40678 2.85301 3.26249 3.92831
6.00550 4.49928 153 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
136 2.72718 4.93439 2.61804 1.49335 4.33894 3.30646 3.76751 3.67401
2.59271 3.33255 4.20236 2.90985 3.85192 2.93759 3.02961 2.74013 2.20277 3.33154
5.58398 4.22854 154 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
137 3.22367 4.54297 4.81042 4.29477 3.28052 4.51488 4.91059 1.22931
4.12691 1.39564 3.11095 4.54183 4.76195 4.35034 4.28848 3.89419 3.46866 1.87895
5.31062 4.13865 155 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
138 2.95523 5.42503 1.11559 2.15164 4.74517 3.22157 3.82919 4.32308
2.88202 3.85279 4.72738 2.31205 3.86871 3.01344 3.47406 2.85854 3.27048 3.89231
5.96726 4.46584 156 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
139 2.92771 4.38160 4.18777 3.68403 2.87871 3.98849 4.07589 1.46781
3.52094 2.10957 3.30013 3.89757 4.34430 3.78857 3.71880 3.32039 3.17069 2.23072
4.56709 2.22863 157 i - - -
2.68620 4.42227 2.77522 2.73125 3.46356 2.40515 3.72402 3.29356 2.67743
2.69357 4.24692 2.90349 2.73742 3.18148 2.89803 2.37889 2.77522 2.98520 4.58479
3.61505
0.19054 1.80294 4.74744 0.29772 1.35678 0.48576 0.95510
140 2.51237 4.54662 2.93829 2.66324 4.19713 3.18523 3.90862 3.58273
2.75896 3.27756 4.14122 1.93962 3.80600 3.11971 3.14115 2.61616 1.72805 3.18967
5.50879 4.19718 159 t - - -
```

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
141 2.85659 4.85399 2.80347 2.70562 4.24217 3.29164 4.05411 3.98803
2.97206 3.61820 4.57439 0.91375 3.95207 3.32914 3.33018 2.91922 3.24472 3.59467
5.53072 4.18110 160 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
142 1.74377 4.34722 3.35148 2.91046 3.85123 3.25637 3.95818 3.10284
2.86728 2.50196 3.78844 3.25438 2.27364 3.21773 3.21967 2.62493 2.81345 2.80777
5.27163 4.01558 161 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
143 2.71443 5.02081 2.10019 1.81887 4.29437 3.33197 3.68423 3.65345
2.54608 3.29538 4.12984 2.83915 3.82448 2.83713 3.04401 2.69984 2.96863 2.45579
5.53823 4.15145 162 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
144 1.46953 4.17388 3.45867 3.17721 4.28612 2.95868 4.24142 3.64480
3.22453 3.38528 4.23217 3.32417 3.70914 3.51944 3.52939 1.41567 2.72535 3.12671
5.64613 4.42637 163 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
145 3.17986 4.48584 4.85345 4.31787 3.34930 4.52242 4.95098 1.30809
4.19457 1.45288 3.14773 4.55657 4.76297 4.38907 4.35894 3.88514 3.42256 1.63986
5.36621 4.22596 164 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
146 2.19206 4.59706 3.02321 2.20462 3.80326 3.42131 3.70135 3.18863
2.56375 2.86094 3.72247 3.03836 3.84729 2.91152 2.98299 2.69095 2.57574 2.91188
5.15688 2.78594 165 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
147 2.69121 4.23437 4.01198 3.47838 2.18721 3.73202 4.14203 2.34175
3.38228 2.17261 3.27746 3.72889 4.15431 3.63869 3.62204 3.05574 2.24998 1.86799
4.86438 3.59027 166 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
148 2.16327 4.28973 4.14987 3.60035 3.34509 3.91632 4.31761 1.67864
3.48868 2.05829 2.44722 3.87788 4.28802 3.75666 3.72777 3.23203 3.05623 2.01968
5.05166 3.86753 167 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
149 2.84215 5.15423 2.83333 2.44047 4.51411 3.45204 3.63120 3.94343
1.57939 3.43137 4.25384 2.23716 3.89609 2.44386 2.50563 2.81167 3.06268 3.57620
5.54106 4.23133 168 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
150 2.54657 4.64700 2.96230 2.55541 4.15005 3.27663 3.75875 3.56240
2.54084 3.18018 4.01361 3.01635 3.80318 2.23570 2.93984 1.92622 2.29936 3.19360
5.41403 4.10554 169 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
151 3.33002 4.74841 4.43394 4.07687 3.19997 4.17458 4.68490 2.41486
3.84312 0.70779 3.17954 4.33748 4.58523 4.17477 3.99325 3.76683 3.61819 2.49136
5.13215 3.88991 170 l - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
152 3.21898 4.53838 4.84094 4.28138 3.18699 4.51286 4.85609 1.40100
4.14479 1.30535 2.53239 4.52874 4.72118 4.29228 4.28259 3.85938 3.44731 2.01558
5.22354 4.13017 171 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
153 2.05284 4.78631 2.04263 2.39189 4.38722 2.40812 3.78019 3.83554
2.67243 3.41777 4.22614 2.89540 3.77689 2.94298 3.16245 2.30432 2.90471 3.40274
5.62409 4.25782 172 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
154 3.09089 5.22592 2.56202 0.82634 4.59241 3.37774 3.98099 4.07700
2.88130 3.67069 4.64056 3.02951 3.99035 3.19510 3.30408 3.05927 3.39713 3.74605
5.73522 4.46059 173 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
155 2.92986 4.43291 4.33452 4.00469 3.66577 3.87938 4.78135 2.05459
3.87481 2.32779 3.60998 4.16937 4.43309 4.22468 4.07226 3.39436 3.28877 0.85226
5.47522 4.21531 174 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
156 2.56402 4.38424 4.45298 3.92171 3.37648 4.18157 4.61136 1.40775
3.78913 1.59308 3.22495 4.17963 4.51375 4.05199 3.99938 3.52396 3.23303 1.86041
5.22598 4.04809 175 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
157 2.76966 5.13236 1.68545 2.02405 4.28443 3.31730 3.68465 3.83835
2.58028 3.39775 4.22770 2.80315 3.83157 2.84843 3.09274 2.72962 3.02446 3.47856
5.54601 2.82533 176 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
158 2.56402 4.38424 4.45298 3.92171 3.37648 4.18157 4.61136 1.40775
3.78913 1.59308 3.22495 4.17963 4.51375 4.05199 3.99938 3.52396 3.23303 1.86041
5.22598 4.04809 177 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
159 3.45825 4.81603 4.44812 4.19374 0.79153 4.10787 3.95340 2.96558
4.09750 2.30148 3.67455 4.19402 4.56467 4.22394 4.17942 3.71886 3.76029 2.96711
4.16127 2.51081 178 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
160 2.69267 4.54144 3.24044 2.91365 3.32451 1.59390 3.86712 3.33411
2.93967 2.97617 3.92164 3.29072 3.95793 3.28437 3.27656 2.83383 3.02119 3.05035
4.83161 2.16869 179 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
161 2.76715 5.21558 1.86580 2.22803 4.45801 3.31594 2.69552 3.98934
2.48954 3.49902 4.30256 2.78913 3.82030 2.18010 2.98255 2.71057 3.01778 3.59171
5.63324 4.20144 180 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
162 2.05529 4.28649 3.31109 2.90912 4.18794 3.05621 4.01997 3.58661
2.93119 3.25570 4.08039 3.20093 2.34739 3.24611 3.30463 1.71515 2.33928 3.12139
5.51242 4.26388 181 s - - -

-continued

```
2.68593 4.42234 2.77529 2.73132 3.46290 2.40496 3.72503 3.29363 2.67716
2.69364 4.24699 2.90356 2.73749 3.18155 2.89810 2.37896 2.77529 2.98527 4.58486
3.61512
0.19054 1.80294 4.74744 1.14246 0.38424 0.48576 0.95510
163 2.64436 4.74751 2.95172 2.59249 4.28010 3.30937 3.77237 3.70607
1.89804 3.30537 4.15267 3.04417 3.85072 2.94725 2.77513 1.59951 2.95732 3.32804
5.48107 4.18238 186 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
164 2.86169 5.12724 3.02635 2.29350 4.49470 3.51639 3.61130 3.89662
2.08523 3.37892 4.20738 3.01438 3.92179 1.95758 1.81265 2.84235 3.06492 3.54592
5.48524 4.21303 187 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
165 2.92039 4.98831 3.24387 2.72304 4.00298 3.57684 1.80210 3.74629
2.14586 3.25720 4.14395 3.15911 3.99296 2.85717 1.86055 2.94659 3.13341 3.44200
5.21564 3.86174 188 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
166 3.16649 4.52728 4.63396 4.13742 1.55523 4.29617 4.32301 1.73842
4.00286 1.76408 3.11947 4.27581 4.58882 4.13968 4.13035 3.65327 3.40793 2.23962
4.62924 3.16052 189 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
167 2.71616 4.54379 3.33734 2.89839 3.35881 3.52119 1.88099 3.03052
2.73076 2.72740 3.72287 3.29273 3.99214 3.17166 3.04330 2.87211 2.99426 2.11386
4.86847 3.42750 190 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
168 3.22367 4.54297 4.81042 4.29477 3.28052 4.51488 4.91059 1.22931
4.12691 1.39564 3.11095 4.54183 4.76195 4.35034 4.28848 3.89419 3.46866 1.87895
5.31062 4.13865 191 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
169 2.86527 4.62317 3.57011 3.49011 4.62505 0.52816 4.59887 4.26391
3.69199 3.89823 4.87687 3.73474 4.01908 4.00427 3.90917 3.04194 3.35840 3.76278
5.67765 4.73288 192 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
170 2.86527 4.62317 3.57011 3.49011 4.62505 0.52816 4.59887 4.26391
3.69199 3.89823 4.87687 3.73474 4.01908 4.00427 3.90917 3.04194 3.35840 3.76278
5.67765 4.73288 193 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
171 3.15998 5.30397 0.72157 2.44238 4.70300 3.33206 4.07440 4.32728
3.18878 3.90937 4.89317 3.00552 3.99587 3.31546 3.72392 3.10675 3.50263 3.95099
5.84132 4.55374 194 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
172 3.09089 5.22592 2.56202 0.82634 4.59241 3.37774 3.98099 4.07700
2.88130 3.67069 4.64056 3.02951 3.99035 3.19510 3.30408 3.05927 3.39713 3.74605
5.73522 4.46059 195 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
173 3.03706 4.46123 4.46014 3.98106 1.57167 4.10443 4.24942 2.28280
3.85931 1.91458 3.22087 4.12421 4.47266 4.03641 4.01751 3.47073 3.30403 1.73003
4.62332 3.14202 196 f - - -
```

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
174 2.32225 4.32069 3.13729 2.87421 4.35136 1.65657 4.08217 3.79969
3.01777 3.44336 4.26128 3.17370 2.25259 3.31182 3.38967 2.14062 2.77627 3.26797
5.65409 4.39735 197 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
175 2.77356 4.55240 3.36005 3.02883 3.03128 2.19986 3.81466 3.28169
3.02848 2.90846 3.88407 3.37503 4.02902 3.36419 3.34043 2.92590 3.08810 3.02523
4.58745 1.50614 198 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
176 1.95337 4.19969 3.34800 3.07948 4.36705 2.35937 4.20484 3.79149
3.18170 3.46901 4.28439 3.26868 3.69495 3.46172 3.51355 1.24981 2.72315 3.22225
5.69329 4.47112 199 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
177 2.39774 4.20251 3.60629 3.18490 3.80064 2.23296 4.12488 2.85980
3.14287 2.80777 3.74384 3.41498 3.85700 3.45238 3.44611 2.62720 2.36371 1.66673
5.26621 4.04642 200 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
178 2.38790 5.01217 2.16371 1.84521 4.31095 3.32870 3.65438 3.71322
2.49136 3.30979 4.12031 2.83572 3.80369 2.79616 2.98853 2.65926 2.92717 2.85244
5.52656 4.13944 201 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
179 2.61109 4.80868 2.83140 2.42367 4.14867 3.33387 2.63708 3.60488
2.46727 3.19337 4.01193 2.36100 3.80714 2.83564 2.90423 2.19422 2.59690 3.24945
5.39695 4.04967 202 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
180 2.81732 5.09001 2.58061 2.36617 4.38635 3.33443 3.73003 3.93915
2.47400 3.47372 4.32793 1.64051 3.87553 2.12574 2.86476 2.79602 3.09304 3.56473
5.58156 4.19469 203 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
181 2.65819 4.65095 3.05975 2.68725 3.79892 3.36853 1.84754 3.44029
2.57169 3.07100 3.97226 3.12206 3.89114 3.03336 2.90858 2.75178 2.16790 3.13088
5.17761 3.79287 204 h - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
182 2.96406 5.52572 1.67512 1.28150 4.81416 3.24219 3.78335 4.33080
2.79447 3.83502 4.68921 2.70807 3.86182 2.94974 3.38467 2.84856 3.25200 3.90619
5.98418 4.48605 205 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
183 3.45825 4.81603 4.44812 4.19374 0.79153 4.10787 3.95340 2.96558
4.09750 2.30148 3.67455 4.19402 4.56467 4.22394 4.17942 3.71886 3.76029 2.96711
4.16127 2.51081 206 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
184 3.15114 4.53079 4.54737 4.17094 3.48096 4.22724 4.87288 0.90672
4.00200 2.03850 3.39535 4.39520 4.64605 4.33611 4.18143 3.73942 3.44853 1.86187
5.40162 4.15144 207 i - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
185 2.29359 4.57411 3.23618 2.72238 4.07343 3.33651 3.77690 3.40764
2.45363 3.07074 3.93300 3.13396 3.84538 2.96550 1.96761 2.66852 2.04261 3.07564
5.33763 4.07790 208 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
186 3.63652 4.88388 4.59704 4.28042 1.43903 4.38085 3.47632 3.33528
4.12987 2.66923 3.93490 4.06005 4.69349 4.11295 4.17606 3.75032 3.85988 3.25834
3.62050 1.04097 209 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
187 2.17639 4.26574 4.04726 3.51142 3.41588 3.78284 4.27057 2.20297
3.40765 2.18515 2.39451 3.78341 4.20778 3.68936 3.66373 3.11174 3.00081 1.61474
5.07651 3.88099 210 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
188 2.85659 4.85399 2.80347 2.70562 4.24217 3.29164 4.05411 3.98803
2.97206 3.61820 4.57439 0.91375 3.95207 3.32914 3.33018 2.91922 3.24472 3.59467
5.53072 4.18110 211 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
189 2.66941 5.00923 2.47300 2.32302 4.31106 3.35985 3.62270 3.75120
2.19826 3.29945 4.09839 2.86151 3.80561 2.23981 2.83829 2.65411 2.21029 3.38199
5.48709 4.11773 212 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
190 3.27661 4.60563 4.81638 4.28979 3.17506 4.53343 4.88108 1.60763
4.11630 1.03186 2.99695 4.54933 4.75580 4.30643 4.26407 3.90698 3.51388 2.04894
5.23833 4.09917 213 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
191 1.63294 4.41666 3.04918 2.73549 4.24684 3.09761 3.95513 3.66617
2.85127 3.31811 4.14383 2.29638 3.74809 3.16486 3.24963 1.95333 2.79798 3.20877
5.55041 4.26583 214 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
192 2.42661 5.01947 2.53569 1.98436 4.31175 3.35699 3.59114 3.76608
2.17969 3.29982 4.08000 2.84213 3.78084 2.51070 2.84308 2.60825 2.86464 3.38286
5.47827 3.40544 215 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
193 2.73220 4.34615 3.90677 3.46424 1.63890 3.64664 4.03956 2.62607
3.37613 2.27422 3.42454 3.68477 4.14040 3.64678 3.61607 3.02242 2.16275 2.48775
4.66374 3.20637 216 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
194 2.16825 4.34510 4.19396 3.65621 3.35689 3.97994 4.39486 1.79160
3.53820 1.55186 3.23332 3.94174 4.34864 3.81543 3.78020 3.30539 3.12015 2.00109
5.11793 3.93073 217 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
195 2.79107 5.18477 2.71691 2.14080 4.52818 3.40467 3.62058 3.96898
1.73192 3.45474 4.25667 2.34029 3.85501 2.42487 2.63243 2.74760 3.01738 3.58213
5.57965 4.23023 218 k - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
196 2.17351 4.91848 2.82525 2.38430 4.24494 3.37072 3.63096 3.67443
2.18425 3.23659 4.04258 2.63554 3.81110 2.28399 2.79466 2.43337 2.89157 3.31531
5.43364 4.08866 219 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
197 2.73064 4.86893 2.99005 2.58925 4.35918 3.38261 3.72140 3.77606
1.45572 3.34226 4.18943 3.04768 3.88536 2.88118 2.59856 2.08548 3.01111 3.40813
5.48642 4.20070 220 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
198 2.56290 4.62791 2.74963 2.60888 4.43158 1.46710 3.99297 3.95890
2.92107 3.57347 4.42130 2.00642 3.80821 3.21235 3.32962 2.64710 2.97621 3.47103
5.69418 4.37504 221 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
199 2.73189 4.38668 3.61904 3.07898 3.11938 3.68134 3.81351 2.76901
2.55667 1.72266 3.41540 3.43335 4.05792 3.26008 3.12675 2.97024 2.96137 2.59805
4.66904 2.43252 222 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
200 2.65108 4.74259 3.04709 2.29681 3.98555 3.45784 3.65624 2.67551
1.89518 2.98080 3.83352 3.01835 3.85857 2.82707 2.76275 2.71055 2.60859 3.02589
5.25791 3.96166 223 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
201 2.38113 4.31424 3.32791 2.99399 4.12869 3.10910 4.08577 3.43979
2.98866 3.17399 4.06943 3.27264 2.27484 3.34184 3.31817 2.54702 1.45834 3.04225
5.49054 4.25327 224 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
202 2.98916 5.10962 3.32022 2.74098 4.48074 3.61552 3.64222 3.89779
1.98743 3.35988 4.23864 3.16576 4.01180 2.07330 1.39674 2.99326 3.17981 3.58157
5.43508 4.22036 225 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
203 3.09044 4.44185 4.68618 4.13199 3.26701 4.35354 4.73982 1.51154
4.00631 1.73823 1.99577 4.37110 4.62020 4.19557 4.17179 3.69350 3.32913 1.76431
5.21204 4.08646 226 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
204 3.60096 4.91925 4.33214 4.07762 2.83833 3.90754 4.10001 3.63349
3.79776 3.00100 4.25985 4.19643 4.43850 4.17747 3.89848 3.80310 3.90961 3.52799
0.62664 2.83283 227 W - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
205 2.85659 4.85399 2.80347 2.70562 4.24217 3.29164 4.05411 3.98803
2.97206 3.61820 4.57439 0.91375 3.95207 3.32914 3.33018 2.91922 3.24472 3.59467
5.53072 4.18110 228 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
206 3.15998 5.30397 0.72157 2.44238 4.70300 3.33206 4.07440 4.32728
3.18878 3.90937 4.89317 3.00552 3.99587 3.31546 3.72392 3.10675 3.50263 3.95099
5.84132 4.55374 229 d - - -

2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
207 2.28767 4.25336 3.22565 3.03895 4.41562 1.37205 4.22746 3.89341
3.21589 3.56086 4.38699 3.25727 3.71863 3.49420 3.54255 1.71487 2.78132 3.30636
5.73165 4.49652 230 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
208 3.25623 4.57823 4.82697 4.30148 3.21152 4.53230 4.89679 1.44812
4.13378 1.15209 3.03278 4.55421 4.75989 4.32875 4.28350 3.90611 3.49523 1.98079
5.26405 4.11904 231 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
209 2.80010 4.33166 4.12940 3.66116 3.55045 3.84603 4.46252 1.34018
3.52807 2.25174 3.43779 3.91340 4.31270 3.85909 3.77462 3.22431 2.22474 1.92066
5.27920 4.06016 232 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
210 2.79829 4.93956 3.01406 2.59905 4.38362 3.43304 3.72082 3.79421
1.40715 3.34475 4.20267 3.06716 2.45331 2.87825 2.57747 2.82418 3.05809 3.44407
5.48224 4.21630 233 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
211 2.14795 5.03770 2.52238 1.85139 4.41195 3.28995 3.71268 3.84816
2.56224 3.42164 4.24450 2.05658 3.82237 2.86803 3.04128 2.70563 3.00132 3.46734
5.62053 4.23176 234 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
212 2.44376 4.49494 2.95928 2.65452 4.24938 2.20366 3.90473 3.66924
2.78324 3.30955 4.13709 2.29943 3.76449 3.10457 3.19217 2.54902 1.89843 3.23177
5.53976 4.24332 235 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
213 3.11698 4.44078 4.79517 4.23551 2.67649 4.40366 4.73857 1.47037
4.12062 1.44738 3.03832 4.44024 4.64572 4.25671 4.24830 3.74254 3.34840 1.77847
5.13226 3.97767 236 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
214 2.68834 5.15778 2.35823 2.07116 4.46480 3.32522 3.03255 3.94105
2.41427 3.44528 4.22121 2.54463 3.78861 2.21954 2.91428 2.41944 2.93063 3.53111
5.60196 4.18680 237 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
215 2.78137 5.18786 2.63785 2.12327 4.51511 3.37631 3.63283 3.96515
2.12021 3.46170 4.26394 2.22167 3.84352 2.04027 2.72768 2.73503 3.01511 3.57673
5.60021 4.23159 238 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
216 3.29986 4.65272 4.75365 4.23684 3.12824 4.50328 4.83093 1.87890
4.03958 0.89447 2.96781 4.50797 4.73645 4.25041 4.19306 3.88386 3.53958 2.16159
5.19499 4.03863 239 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
217 2.89919 5.34935 1.71617 2.17213 4.67656 3.23525 3.79474 4.23262
2.79260 3.76123 4.61425 1.50751 3.85502 2.96887 3.35665 2.81751 3.20239 3.80806
5.88804 4.40854 240 n - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
218 2.80413 4.99658 3.13747 2.58273 4.37486 3.50907 3.62429 3.76811
1.81527 3.28795 4.12050 3.05219 2.40061 2.76252 1.94630 2.81408 3.01946 3.42826
5.42318 4.16153 241 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
219 2.78727 5.25825 2.11249 1.98930 4.57502 3.27529 3.69467 4.06071
2.59247 3.57583 4.38220 2.01326 3.81702 2.83915 3.12919 2.10157 3.05347 3.64961
5.74702 4.30348 242 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
220 3.06362 4.40738 4.70321 4.15807 2.25304 4.31291 4.61746 1.40759
4.03918 1.78965 3.10819 4.34583 4.59211 4.19971 4.17936 3.65397 3.30298 1.78011
5.03341 3.78118 243 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
221 2.74310 5.10413 2.57119 1.79870 4.42891 3.33094 3.66692 3.88451
2.44904 3.41973 4.23166 2.83556 3.82732 2.22809 2.90068 2.13381 2.99672 3.50373
5.59369 4.20923 244 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
222 3.11590 4.45267 4.76412 4.28578 3.51743 4.40926 4.99791 1.04667
4.15057 2.00332 3.33678 4.50531 4.74212 4.42536 4.34502 3.81003 3.39025 1.52516
5.50474 4.29626 245 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
223 2.66285 4.37534 3.71357 3.25967 3.54783 3.54839 4.15639 2.55844
3.10913 1.83168 3.50335 3.56378 4.07135 3.49067 3.39233 2.92788 1.65978 2.40085
5.17034 3.92022 246 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
224 3.47415 4.90106 4.06661 3.82674 2.31411 4.01031 3.69985 3.46280
3.67999 2.87675 4.12240 3.91595 4.48161 3.94901 3.83146 3.59477 3.76213 3.34085
3.96297 0.74537 247 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
225 3.60096 4.91925 4.33214 4.07762 2.83833 3.90754 4.10001 3.63349
3.79776 3.00100 4.25985 4.19643 4.43850 4.17747 3.89848 3.80310 3.90961 3.52799
0.62664 2.83283 248 W - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.19054 4.02509 1.86030 0.61958 0.77255 0.48576 0.95510
226 2.31190 4.23221 3.20093 3.01641 4.06999 2.96221 4.12644 3.59174
3.08975 3.31246 4.23908 3.24220 3.70049 3.43956 3.37598 1.10062 2.79156 3.12823
5.44298 4.15348 249 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
227 3.23798 4.72953 3.82891 3.55712 2.29361 3.82278 3.61560 3.24807
3.41482 2.70363 3.92376 3.71568 4.29677 3.72237 3.59982 3.37530 3.52463 3.11833
3.93713 0.97636 250 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
228 2.98282 5.11011 0.92716 2.33101 4.48628 3.20589 3.92549 4.07302
3.00841 3.68247 4.66044 2.88705 3.85823 3.16463 3.52377 2.94589 3.32126 3.71287
5.65612 4.36023 251 d - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
229 2.65708 4.43313 3.32956 3.22817 4.37057 0.73893 4.34882 3.96866
3.40858 3.62358 4.59928 3.49387 3.82406 3.73324 3.64531 2.82881 3.13782 3.49820
5.46738 4.47226 252 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
230 2.83473 5.25837 1.37516 2.10126 4.57628 3.15435 3.73554 4.13385
2.75360 3.68191 4.54871 2.21985 3.78459 2.91774 3.31984 2.75590 3.14441 3.71856
5.80743 4.32822 253 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
231 1.87653 4.19185 3.40469 2.94377 3.81375 3.13129 3.95270 3.00747
2.90476 2.83368 3.73463 3.23401 2.87014 3.22707 3.24995 2.50645 2.33265 2.33069
5.22956 3.99695 254 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
232 2.87575 4.86127 2.89877 2.65342 4.02899 3.36186 3.81166 3.65879
2.47464 3.16177 4.18981 3.11309 3.91524 1.24532 2.75894 2.92378 3.17273 3.38886
5.30213 3.99546 255 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
233 2.41899 5.21973 1.80670 1.92196 4.52691 3.20434 3.65972 4.00235
2.59039 3.53493 4.35784 2.34466 3.76804 2.81406 3.13577 2.69270 3.03520 3.60188
5.71875 4.27077 256 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.40460 1.10034
234 2.81580 5.10307 2.79216 2.16513 4.47096 3.42522 3.64987 3.88379
1.46686 3.40247 4.22936 2.93968 3.88555 2.78962 2.57994 2.49116 3.04799 3.52196
5.54016 4.22559 257 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
235 2.83358 5.20058 2.53761 2.09198 4.51162 3.35379 3.68148 3.97571
2.40863 3.49193 4.32040 2.48310 3.86434 1.64646 2.81525 2.78610 3.08153 3.59969
5.63746 4.26133 258 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
236 2.43482 5.16048 2.04732 1.84642 4.49572 3.28349 3.68297 3.96379
2.56062 3.49693 4.29959 2.78033 3.80735 2.82537 3.08519 2.11200 3.00356 3.56137
5.67864 4.25482 259 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
237 2.34706 4.45402 3.19665 2.42774 3.69805 3.43232 3.75883 2.49411
2.66416 2.74040 3.61797 3.13325 3.86377 3.00067 3.06327 2.46650 2.29246 2.74007
5.08842 3.82155 260 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
238 2.24371 4.63974 3.17377 2.62187 3.85290 3.48107 3.68434 3.22312
2.41011 2.30770 3.73727 3.08964 3.88042 2.39579 2.48289 2.73901 2.87752 2.95645
5.16854 3.89489 261 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
239 2.63695 4.87264 2.88253 1.96285 4.12306 3.39891 3.61882 3.56319
2.36872 3.14390 3.95830 2.92286 3.81479 2.76660 2.52556 2.20831 2.87080 3.22744
5.35052 3.37891 262 e - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
240 2.85358 4.99403 3.08886 2.63719 4.37776 3.48290 3.68537 3.85142
2.16243 3.37009 4.22735 2.21122 3.94249 2.84227 1.48771 2.87143 3.09524 3.50308
5.44726 4.17392 263 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
241 2.75465 4.78117 3.22906 2.78590 4.35488 2.17295 3.81911 3.80189
2.36225 3.36434 4.22896 3.19546 3.92329 2.99973 1.40706 2.82785 3.05972 3.42919
5.46478 4.24602 264 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
242 2.20101 5.05804 2.47317 1.98804 4.36317 3.35363 3.60088 3.81801
2.20618 3.34357 4.12538 2.83753 3.78990 2.72407 2.57485 2.62833 2.89281 3.42934
5.51398 4.12789 265 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
243 2.75348 4.39430 3.70171 3.14573 3.36241 3.75526 4.01294 1.80133
2.98311 2.13442 2.82860 3.52809 4.11819 2.47948 3.28188 3.03460 2.98709 2.39123
4.98230 3.76796 266 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
244 2.61364 4.69998 3.12146 2.65979 4.27617 2.72110 3.75212 3.69618
2.36249 3.27491 4.10869 3.08671 3.84610 2.91961 1.61994 2.31938 2.92260 3.31091
5.44651 4.17600 267 r - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
245 2.45733 4.23093 4.00985 3.44521 3.32408 3.81725 4.16947 2.23469
3.34821 1.79842 2.76896 3.73818 4.18660 3.61374 3.60131 3.11208 2.62154 1.80191
4.94904 3.75739 268 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
246 2.76092 5.14264 1.70565 2.22245 4.56863 3.23368 3.75263 4.06575
2.68811 3.60327 4.42311 2.44221 3.81705 2.91194 3.22493 1.89100 3.06175 3.63884
5.77454 4.33594 269 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
247 3.11349 4.48621 4.63246 4.07039 3.17950 4.33632 4.67836 2.08695
3.93732 1.29228 2.22825 4.32892 4.59200 4.11854 4.10432 3.66807 3.34622 1.67574
5.14291 4.03188 270 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
248 2.71971 4.81987 2.85700 2.56299 4.22841 3.33437 3.80271 3.71370
2.53336 3.28043 4.16984 3.03870 1.75864 2.11513 2.88890 2.76818 3.02510 3.36563
5.47091 4.15744 271 p - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
249 2.97289 5.54922 1.50860 1.39490 4.83522 3.23803 3.78628 4.35630
2.80796 3.85609 4.71182 2.70120 3.86227 2.95335 3.40637 2.85290 3.26228 3.92797
6.00516 4.49906 272 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
250 3.32508 4.67165 4.72729 4.22925 1.99281 4.44057 4.42007 2.34080
4.08403 0.99220 2.97759 4.39966 4.67805 4.18892 4.19822 3.80743 3.55414 2.46146
4.67349 3.24070 273 l - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
251 2.75073 4.43475 3.55181 2.34149 3.46655 3.72841 3.99695 2.05397
2.94925 1.80947 3.37599 3.45472 4.10290 3.30123 3.28386 3.01000 2.98637 2.33408
5.06057 3.82578 274 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
252 1.88494 4.88238 2.61903 1.57478 4.33632 3.28033 3.79591 3.66483
2.65101 3.33863 4.20937 2.91965 3.84486 2.97237 3.09640 2.72567 3.00924 3.31495
5.59647 4.24410 275 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518
4.58477 3.61503
0.02689 4.02509 4.74744 0.61958 0.77255 0.48576 0.95510
253 2.82293 5.14889 2.73180 2.39082 4.48956 3.41412 3.64604 3.93246
1.88521 3.43481 4.25714 1.88069 3.87925 2.42818 2.61224 2.79021 3.05405 3.56270
5.56070 4.22736 276 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
254 2.86527 4.62317 3.57011 3.49011 4.62505 0.52816 4.59887 4.26391
3.69199 3.89823 4.87687 3.73474 4.01908 4.00427 3.90917 3.04194 3.35840 3.76278
5.67765 4.73288 277 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
255 3.32075 4.67106 4.65248 4.18787 1.42808 4.36915 4.17707 2.44930
4.03693 1.35663 3.11212 4.29060 4.64318 4.14491 4.14864 3.74047 3.55563 2.53074
4.41270 2.86475 278 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
256 2.24759 4.60593 3.04042 2.58380 4.12442 3.27735 3.75496 3.51675
2.11361 3.14698 3.97472 3.03517 3.79537 2.92994 2.93036 1.90830 2.50489 3.14958
5.38891 4.09154 279 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
257 2.92986 4.43291 4.33452 4.00469 3.66577 3.87938 4.78135 2.05459
3.87481 2.32779 3.60998 4.16937 4.43309 4.22468 4.07226 3.39436 3.28877 0.85226
5.47522 4.21531 280 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
258 3.07555 4.54456 4.17165 3.68951 2.63692 4.05019 3.94163 2.61906
3.49418 1.25994 3.29193 3.89312 4.39198 3.76636 3.68862 3.39142 3.31141 2.59153
4.34766 2.02939 281 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
259 2.85659 4.85399 2.80347 2.70562 4.24217 3.29164 4.05411 3.98803
2.97206 3.61820 4.57439 0.91375 3.95207 3.32914 3.33018 2.91922 3.24472 3.59467
5.53072 4.18110 282 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
260 3.47415 4.90106 4.06661 3.82674 2.31411 4.01031 3.69985 3.46280
3.67999 2.87675 4.12240 3.91595 4.48161 3.94901 3.83146 3.59477 3.76213 3.34085
3.96297 0.74537 283 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
261 2.85659 4.85399 2.80347 2.70562 4.24217 3.29164 4.05411 3.98803
2.97206 3.61820 4.57439 0.91375 3.95207 3.32914 3.33018 2.91922 3.24472 3.59467
5.53072 4.18110 284 n - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
262 1.43858 4.17262 3.46197 3.17982 4.28413 2.95862 4.24230 3.64182
3.22630 3.38304 4.23010 3.32547 3.70912 3.52089 3.53067 1.44573 2.72482 3.12450
5.64474 4.42553 285 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
263 3.47415 4.90106 4.06661 3.82674 2.31411 4.01031 3.69985 3.46280
3.67999 2.87675 4.12240 3.91595 4.48161 3.94901 3.83146 3.59477 3.76213 3.34085
3.96297 0.74537 286 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
264 2.74307 4.51705 3.42036 3.04746 2.87779 3.52330 3.74578 3.20288
3.00035 2.82798 3.81047 3.37158 4.03361 3.33906 3.30723 2.08907 3.05136 2.95530
4.45959 1.58668 287 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
265 3.33002 4.74841 4.43394 4.07687 3.19997 4.17458 4.68490 2.41486
3.84312 0.70779 3.17954 4.33748 4.58523 4.17477 3.99325 3.76683 3.61819 2.49136
5.13215 3.88991 288 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
266 3.47415 4.90106 4.06661 3.82674 2.31411 4.01031 3.69985 3.46280
3.67999 2.87675 4.12240 3.91595 4.48161 3.94901 3.83146 3.59477 3.76213 3.34085
3.96297 0.74537 289 y - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
267 3.06590 4.44659 4.57685 4.04403 1.61299 4.22908 4.39647 1.95419
3.92037 1.77072 3.09615 4.22291 4.52802 4.07839 4.06953 3.56593 3.30701 1.93196
4.78360 3.40738 290 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
268 2.60870 4.27440 3.61511 3.08337 3.46566 3.58777 3.96543 2.51818
2.99375 2.01440 3.42185 2.95296 4.01275 3.32065 3.30807 2.88412 2.53476 1.85585
4.97454 3.74232 291 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
269 2.96585 4.69526 3.58992 3.45271 4.43091 3.37425 4.51572 4.01796
3.52354 3.62729 4.68520 3.74295 0.58713 3.90765 3.74983 3.13863 3.41988 3.64553
5.57332 4.55440 292 P - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.19054 4.02509 1.86030 0.61958 0.77255 0.48576 0.95510
270 2.89331 5.05333 2.98954 2.55821 4.40661 3.47941 3.59759 3.81675
1.40054 3.30995 4.18773 3.01921 3.91542 2.33069 2.27380 2.88761 3.10173 3.49586
5.41357 4.16617 293 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
271 2.33815 4.83772 2.63892 2.08725 4.18880 2.83748 3.63933 3.61624
2.45851 3.20259 4.02467 2.83958 3.76436 2.48516 2.91281 2.36814 2.87531 3.26022
5.42481 4.07350 294 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
272 2.72453 5.16074 2.05455 1.93695 4.48138 2.74002 3.64595 3.95845
2.55403 3.48728 4.30034 2.39737 3.76070 2.79550 3.08997 2.34261 2.99410 3.55704
5.67109 4.23618 295 e - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
273 2.03246 4.29147 3.29315 2.78127 3.57563 3.31601 3.77695 2.98354
2.72297 2.67806 3.55939 3.16812 3.11459 3.06317 3.08341 2.37611 2.74277 2.70919
3.55740 3.72364 296 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
274 2.39983 4.44256 2.86269 2.57916 4.16160 2.56227 3.83532 3.57218
2.70942 3.22526 4.06283 2.22335 3.70868 3.04080 3.10904 2.50457 2.04754 3.15068
5.45869 4.16143 297 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
275 2.71118 4.24977 3.93892 3.40057 2.74462 3.77463 4.14039 1.86116
3.30717 2.06302 3.21694 3.70036 4.16399 3.58284 3.57194 3.08586 2.26934 2.07541
4.90669 3.65253 298 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
276 2.47273 4.49077 2.96554 2.58865 3.92862 3.20661 3.02877 3.40567
2.57809 3.04785 3.90219 3.01874 3.75850 2.96736 2.95498 1.83384 2.46325 3.05340
5.25968 3.94115 299 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
277 2.66096 4.78608 2.90902 2.45376 3.67156 3.41435 2.66487 3.43737
2.37202 3.02249 3.87755 2.64078 3.83076 2.50558 2.76268 2.69511 2.89080 3.13519
5.03827 3.04247 300 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.40460 1.10034
278 2.35280 5.08499 1.66136 2.24355 4.52064 3.24305 3.73444 3.99270
2.64603 3.53844 4.35045 2.44678 3.80721 2.88826 3.17351 2.32812 3.01748 3.57307
5.72351 4.30230 301 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
279 1.97030 4.21121 3.41504 3.03831 4.22733 2.50950 4.11541 3.63140
3.06682 3.30897 4.12984 3.25922 3.70518 3.36238 3.41696 1.65407 1.93366 3.12889
5.56294 4.33605 302 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
280 2.43503 5.04431 2.55485 2.33252 4.36675 3.37932 3.58876 3.81549
2.02126 3.33246 4.11340 2.57572 3.79834 2.70850 2.25513 2.63424 2.88877 3.42730
5.49043 4.12191 303 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
281 3.42223 4.78022 4.33714 3.94373 1.08833 4.22279 2.73056 3.32322
3.80837 2.74126 3.90317 3.89995 4.55033 3.90484 3.94359 3.55599 3.64354 3.18795
3.67790 1.74048 304 f - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
282 1.25768 4.17189 3.58631 3.26102 4.14671 3.02964 4.25932 3.27851
3.24025 3.15892 4.07464 3.39470 3.75976 3.55430 3.52728 2.47938 1.90838 2.88161
5.56334 4.35799 305 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
283 2.08170 4.57084 3.05405 2.62529 4.05159 3.29052 3.78750 3.40497
2.58532 3.06929 3.92758 3.06775 3.81579 2.25806 2.97215 2.62917 2.05152 3.06777
5.35578 4.06730 306 t - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
284 2.83175 5.14730 2.89501 1.71566 4.50964 3.47051 3.61557 3.92131
1.97022 3.40835 4.22614 2.96037 3.89450 2.74439 2.02273 2.80291 3.04473 3.55675
5.52226 4.22157 307 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
285 3.15998 5.30397 0.72157 2.44238 4.70300 3.33206 4.07440 4.32728
3.18878 3.90937 4.89317 3.00552 3.99587 3.31546 3.72392 3.10675 3.50263 3.95099
5.84132 4.55374 308 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
286 3.10465 4.41921 4.81466 4.32149 3.58133 4.45215 5.03748 1.30485
4.20927 2.08345 3.38653 4.53823 4.76727 4.47513 4.40756 3.84267 3.37231 1.15212
5.55075 4.34415 309 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
287 2.86282 4.34353 4.18270 3.63707 3.34634 3.98519 4.37187 1.77850
3.50843 1.57442 3.22490 3.92839 4.34363 3.79253 3.75031 3.30414 2.29534 2.01067
5.09916 3.91247 310 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
288 2.81017 5.21863 2.59352 1.87222 4.55344 3.36881 3.64927 4.00429
1.78795 3.49979 4.30902 2.27355 3.85315 2.78354 2.74442 2.75861 3.04813 3.61433
5.63373 4.26239 311 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
289 2.78345 5.07319 2.82941 2.42917 4.40388 3.42570 3.63635 3.85576
2.24103 3.36935 4.19039 1.95019 3.87310 2.16956 2.32851 2.76665 3.01448 3.49249
5.49894 4.17188 312 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
290 2.96493 4.42175 4.24644 3.72871 2.75501 3.97278 3.99940 1.90908
3.49686 2.07632 3.28935 3.90362 4.33545 3.77977 3.67133 3.32195 3.20919 2.44765
1.84148 2.93628 313 w - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
291 2.77068 5.21507 1.63809 2.20979 4.53543 3.28893 3.68499 4.00817
2.30622 3.53236 4.33841 2.45292 3.81734 2.82784 3.06700 2.71389 2.65575 3.60510
5.70473 4.27646 314 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
292 3.07555 4.54456 4.17165 3.68951 2.63692 4.05019 3.94163 2.61906
3.49418 1.25994 3.29193 3.89312 4.39198 3.76636 3.68862 3.39142 3.31141 2.59153
4.34766 2.02939 315 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
293 2.46723 4.30593 3.41146 2.94189 3.71832 2.03027 3.93625 2.99694
2.88166 2.73796 2.49579 3.28313 3.85679 3.22461 3.22167 2.65944 2.42962 2.72427
5.15318 3.91282 316 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
294 2.70431 4.42044 3.55159 2.98113 3.55074 3.68133 3.92481 2.27836
2.08770 2.24339 3.45925 3.39572 4.05388 3.20959 3.13430 2.94496 2.93779 1.99785
5.06664 3.82890 317 v - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
295 3.60096 4.91925 4.33214 4.07762 2.83833 3.90754 4.10001 3.63349
3.79776 3.00100 4.25985 4.19643 4.43850 4.17747 3.89848 3.80310 3.90961 3.52799
0.62664 2.83283 318 W - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
296 1.98570 4.97518 1.41558 2.32162 4.50250 3.21472 3.84670 3.88113
2.81882 3.54191 4.41029 2.85524 3.83484 3.02864 3.33839 2.73358 3.07083 3.48636
5.76413 4.36173 319 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
297 2.69267 4.54144 3.24044 2.91365 3.32451 1.59390 3.86112 3.33411
2.93967 2.97617 3.92164 3.29072 3.95793 3.28437 3.27656 2.83383 3.02119 3.05035
4.83161 2.16869 320 g - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
298 2.21146 5.00527 2.91460 2.22523 4.32023 3.42770 3.59528 3.74451
2.08955 3.27456 4.07496 2.92605 3.83286 2.27647 2.39487 2.68562 2.91731 3.38359
5.43862 4.10770 321 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
299 2.81830 4.78567 3.00119 2.68472 3.15135 3.49788 3.68581 3.46076
2.73029 3.04468 3.99274 1.69978 3.98400 3.09700 3.10366 2.87953 3.08823 3.18893
4.68571 2.21104 322 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
300 2.64885 4.94211 2.79848 2.36681 4.26955 3.36475 3.62791 3.70427
2.20331 3.25986 4.06190 2.32020 3.80721 2.50811 2.80560 2.21848 2.60129 3.33904
5.45181 4.09937 323 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
301 2.77130 5.11841 2.81513 2.20210 4.46166 3.42626 3.61280 3.89013
1.72485 3.39017 4.19532 2.91415 3.85823 2.21692 2.58496 2.47751 2.99421 3.51624
5.52419 4.19306 324 k - - -
2.68634 4.42241 2.77499 2.73139 3.46224 2.40529 3.72510 3.29308 2.67757
2.69371 4.24706 2.90363 2.73755 3.18162 2.89817 2.37878 2.77535 2.98534 4.58493
3.61349
0.19054 1.80294 4.74744 1.59375 0.22710 0.48576 0.95510
302 2.81830 4.78567 3.00119 2.68472 3.15135 3.49788 3.68581 3.46076
2.73029 3.04468 3.99274 1.69978 3.98400 3.09700 3.10366 2.87953 3.08823 3.18893
4.68571 2.21104 332 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
303 2.45078 4.83585 3.10014 2.52017 4.10118 3.47518 3.13718 3.07078
1.79435 3.08529 3.91462 3.01122 3.85880 2.76648 2.38592 2.71453 2.89794 3.18724
5.29651 4.00273 333 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
304 2.72071 4.38562 3.63683 3.10081 3.47607 3.70767 4.01238 2.20337
2.96292 2.31855 3.40113 3.48887 4.09819 2.46818 3.27800 2.99681 2.96723 1.69539
5.05050 3.81401 334 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
305 2.67950 4.88566 3.02495 2.29925 4.16327 3.45629 3.60778 3.56642
2.09891 3.13823 3.95856 2.97731 3.84695 2.32151 2.38190 2.69992 2.89944 2.52691
5.34041 4.03408 335 k - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
306 2.91402 5.39319 1.52296 2.15501 4.71409 3.23200 3.79389 4.27088
2.80268 3.79105 4.64407 1.67576 3.85525 2.96681 3.37850 2.82350 3.21615 3.84170
5.91979 4.42986 336 d - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
307 2.56890 4.50622 3.31100 2.87118 4.03458 3.30972 3.88971 3.35763
2.58003 3.05022 3.96233 3.23240 3.87462 3.11323 2.40892 2.70623 1.44002 3.03785
5.34723 4.09854 337 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
308 2.63362 5.03424 2.51857 2.29662 4.33547 3.35630 2.76825 3.79303
2.20584 3.31957 4.09719 2.84091 3.17158 2.50318 2.82936 2.38046 2.86908 3.40417
5.49087 4.10493 338 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
309 2.82659 5.20800 2.57242 2.08730 4.53914 3.36521 3.66607 3.98701
1.92933 3.49486 4.31462 1.83994 3.86208 2.80711 2.76495 2.77788 3.06869 3.60584
5.63596 4.26808 339 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
310 3.11414 4.43068 4.81561 4.32476 3.55929 4.45387 5.03709 1.14792
4.20760 2.04996 3.36501 4.54217 4.76839 4.47155 4.40283 3.84667 3.38230 1.32751
5.53992 4.33715 340 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
311 2.40396 4.35929 3.48101 2.91497 3.49471 3.59476 3.84852 2.28339
2.26694 2.45846 2.65064 3.32377 3.97669 3.15196 3.11428 2.85415 2.86442 2.48102
4.96886 3.73712 341 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
312 2.86527 4.62317 3.57011 3.49011 4.62505 0.52816 4.59887 4.26391
3.69199 3.89823 4.87687 3.73474 4.01908 4.00427 3.90917 3.04194 3.35840 3.76278
5.67765 4.73288 342 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
313 1.69752 4.18345 3.43150 3.16346 4.30119 2.95892 4.24125 3.66483
3.21931 3.40398 4.25258 3.31758 3.71103 3.51749 3.52451 1.23544 2.73257 3.14227
5.65899 4.43456 343 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
314 1.48834 4.17464 3.45665 3.17575 4.28735 2.95870 4.24102 3.64656
3.22362 3.38669 4.23351 3.32345 3.70917 3.51872 3.52871 1.39816 2.72573 3.12803
5.64702 4.42693 344 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
315 3.33002 4.74841 4.43394 4.07687 3.19997 4.17458 4.68490 2.41486
3.84312 0.70779 3.17954 4.33748 4.58523 4.17477 3.99325 3.76683 3.61819 2.49136
5.13215 3.88991 345 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
316 2.06584 4.19822 3.57712 3.15818 3.90798 3.14557 4.12723 3.04807
3.12205 2.93589 3.84949 3.37347 3.80465 3.43083 3.43658 1.60722 2.76076 1.98844
5.34623 4.12095 346 s - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
317 3.13957 4.48635 4.69093 4.17921 2.14551 4.33740 4.52133 1.31504
4.05073 1.76020 3.11148 4.35084 4.62044 4.20491 4.18599 3.69575 3.38191 2.05584
4.87047 3.49872 347 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
318 3.60096 4.91925 4.33214 4.07762 2.83833 3.90754 4.10001 3.63349
3.79776 3.00100 4.25985 4.19643 4.43850 4.17747 3.89848 3.80310 3.90961 3.52799
0.62664 2.83283 348 W - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
319 2.86527 4.62317 3.57011 3.49011 4.62505 0.52816 4.59887 4.26391
3.69199 3.89823 4.87687 3.73474 4.01908 4.00427 3.90917 3.04194 3.35840 3.76278
5.67765 4.73288 349 G - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
320 3.09089 5.22592 2.56202 0.82634 4.59241 3.37774 3.98099 4.07700
2.88130 3.67069 4.64056 3.02951 3.99035 3.19510 3.30408 3.05927 3.39713 3.74605
5.73522 4.46059 350 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
321 2.67457 5.07040 2.51288 2.32096 4.37867 3.37742 2.46681 3.83562
2.12444 3.34985 4.13318 2.59039 3.80325 2.71544 2.51562 2.64684 2.90571 3.44794
5.50375 4.13004 351 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
322 1.14955 4.15975 3.49222 3.22294 4.26745 2.95714 4.26847 3.60294
3.26518 3.36558 4.22220 3.34742 3.71321 3.55904 3.55623 1.83278 2.72661 3.09693
5.63978 4.42521 352 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
323 2.64228 4.88139 2.68741 2.38349 4.35033 2.21629 3.71811 3.79531
2.25822 3.36108 4.17488 2.21099 3.80719 2.87328 2.95866 2.38528 2.93469 3.40017
5.55484 4.19996 353 n - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
324 2.06373 4.76793 2.03727 2.40851 4.36490 3.20037 3.79444 3.79559
2.69130 3.40145 4.21915 2.90775 3.78264 2.96287 3.17508 1.88061 2.91020 3.37323
5.61541 4.25254 354 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
325 3.31291 4.68989 4.70501 4.16903 3.06956 4.47757 4.76869 2.21596
3.95514 0.85086 2.45756 4.45720 4.69951 4.16625 4.10977 3.84449 3.54474 2.34334
5.14329 4.01962 355 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
326 2.68556 4.91318 2.92743 2.46064 4.27560 3.40303 3.64009 3.69681
2.10413 3.25042 4.06639 2.64979 3.84250 2.78308 2.37643 1.87701 2.92907 3.34132
5.42809 4.11261 356 s - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
327 2.73384 5.16697 2.26038 2.05842 4.47205 3.30905 3.65623 3.94222
2.49309 3.46512 4.26233 2.79002 3.80787 2.19583 2.99662 2.01165 2.98632 3.54556
5.63826 4.22328 357 s - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
328 2.47304 5.20505 2.25958 1.72883 4.51131 3.31587 3.63621 3.98735
2.23621 3.49082 4.27593 2.78353 3.80166 2.49647 2.95232 2.67314 2.97505 3.57793
5.64854 4.22756 358 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
329 2.31309 4.23782 3.42672 2.99267 4.01638 2.16856 4.03209 3.37031
2.98113 3.08706 3.93683 3.25944 3.74798 3.29195 3.33356 2.14881 1.87650 2.54167
5.38693 4.15279 359 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
330 3.22367 4.54297 4.81042 4.29477 3.28052 4.51488 4.91059 1.22931
4.12691 1.39564 3.11095 4.54183 4.76195 4.35034 4.28848 3.89419 3.46866 1.87895
5.31062 4.13865 360 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
331 2.73070 4.83158 2.95882 2.31091 4.00995 3.46767 3.68062 3.40112
2.37768 2.31986 3.89168 3.01979 3.89268 1.95665 2.73773 2.77602 2.96076 3.13183
5.29737 3.98938 361 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
332 2.91182 5.20068 2.89705 2.24903 4.57907 3.49904 3.63025 3.97818
1.36116 3.45021 4.28561 2.98825 3.93283 2.45099 2.40200 2.87724 3.11802 3.62284
5.54679 4.26966 362 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
333 2.41393 4.72714 2.94864 2.46805 3.93736 3.40528 3.65291 3.37964
2.46157 3.00100 3.83688 2.68148 3.82558 2.31785 2.89170 2.46055 2.85036 3.07334
5.23863 2.87824 363 q - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
334 2.61198 4.75416 2.76739 1.96203 4.19843 3.28646 3.75307 3.58268
2.58481 3.22154 4.06081 2.95032 3.81628 2.92853 3.01852 2.38680 1.89746 3.22765
5.46722 4.13649 364 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
335 2.19974 4.95289 2.98222 2.52036 4.32341 3.44754 3.65065 3.71385
1.59024 3.26670 4.10407 3.00641 3.88570 2.50656 2.54360 2.77309 2.99388 3.37404
5.43905 4.15062 365 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
336 2.63930 4.90473 2.64813 2.15091 4.31824 2.82213 3.70014 3.76303
2.54055 3.33295 4.14327 2.55980 2.31973 2.85291 3.01742 2.37161 2.92138 3.37746
5.54014 4.17172 366 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
337 3.33002 4.74841 4.43394 4.07687 3.19997 4.17458 4.68490 2.41486
3.84312 0.70779 3.17954 4.33748 4.58523 4.17477 3.99325 3.76683 3.61819 2.49136
5.13215 3.88991 367 l - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
338 3.27661 4.60563 4.81638 4.28979 3.17506 4.53343 4.88108 1.60763
4.11630 1.03186 2.99695 4.54933 4.75580 4.30643 4.26407 3.90698 3.51388 2.04894
5.23833 4.09917 368 l - - -

-continued 2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
339 2.72589 5.08508 2.78918 2.01263 4.41068 3.40328 3.60798 3.84476
1.96810 3.35893 4.15722 2.89084 3.83403 2.20531 2.66343 2.70000 2.60210 3.46923
5.51047 4.16207 369 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
340 1.55374 4.43261 3.01620 2.72155 4.24969 3.10364 3.95467 3.66488
2.85125 3.32280 4.15289 2.15851 3.75481 3.16599 3.24839 2.20449 2.81204 3.21299
5.55493 4.26670 370 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
341 3.01710 4.36412 4.67085 4.12132 2.29109 4.27203 4.60455 1.63727
4.00480 1.85684 3.14379 4.30821 4.56211 4.17766 4.15036 3.60918 3.25731 1.48378
5.05634 3.82126 371 v - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
342 3.22367 4.54297 4.81042 4.29477 3.28052 4.51488 4.91059 1.22931
4.12691 1.39564 3.11095 4.54183 4.76195 4.35034 4.28848 3.89419 3.46866 1.87895
5.31062 4.13865 372 i - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
343 2.63538 4.83548 2.97849 2.44469 4.05169 2.65172 3.12938 3.50730
2.33651 3.09262 3.91198 2.95563 3.82485 2.36990 2.51828 2.66186 2.86262 3.18284
5.29063 3.27945 373 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.02689 4.02509 4.74744 0.61958 0.77255 0.48576 0.95510
344 2.87128 4.82370 3.35071 2.80664 3.94897 3.61266 3.74750 3.24928
1.45400 2.14061 3.87283 3.23468 4.01891 2.94093 2.52181 2.95948 3.09277 3.04076
5.25603 3.98953 374 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.19054 4.02509 1.86030 0.61958 0.77255 0.48576 0.95510
345 2.23775 4.15855 3.30025 3.00592 4.06012 2.96551 4.07132 3.35269
2.99940 3.13830 4.02753 3.22203 3.67752 3.34873 3.30253 2.02036 1.52718 2.93111
5.44319 4.20039 375 t - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
346 2.74399 4.99909 2.69002 2.35595 4.23084 3.35595 2.95780 3.74658
2.02829 3.28474 4.12100 2.05927 3.82464 2.76246 2.62644 2.73093 2.98086 3.40001
5.40330 4.04864 376 k - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
347 2.29867 4.61639 2.31944 2.44568 3.95273 2.83167 3.68936 2.78374
2.56224 2.98071 3.83580 2.94017 3.77569 2.87735 3.01242 2.60957 2.81529 2.96635
5.27868 3.96005 377 a - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.03160 3.86615 4.58850 0.61958 0.77255 0.63100 0.75941
348 2.64330 4.95659 2.26242 2.04359 4.27999 3.25698 3.63141 3.71459
2.48703 3.29015 4.10632 2.78289 2.72426 2.78273 2.98069 2.62871 2.52159 3.34724
5.50264 4.11839 378 e - - -
2.68618 4.42225 2.77519 2.73123 3.46354 2.40513 3.72494 3.29354 2.67741
2.69355 4.24690 2.90347 2.73739 3.18146 2.89801 2.37887 2.77519 2.98518 4.58477
3.61503
0.11129 3.86615 2.47241 0.61958 0.77255 0.63100 0.75941
349 2.71240 4.96152 2.57638 2.05512 4.31062 2.68638 3.61078 3.72641
1.89653 3.28651 4.12646 2.82370 3.78758 2.76814 2.68529 2.70076 2.96495 3.37534
5.46373 4.13251 379 k - - -

2.68621 4.42229 2.77523 2.73127 3.46357 2.40516 3.72422 3.29357 2.67744
2.69358 4.24693 2.90350 2.73743 3.18150 2.89804 2.37871 2.77523 2.98522 4.58480
3.61507
0.19020 1.75326 * 0.66005 0.72738 0.00000

---

The invention claimed is:

1. A composition comprising
   (a) one or more polypeptides having hexosaminidase activity, wherein the polypeptide
      (i) has at least 95% sequence identity to SEQ ID NO: 33 or 34,
      (ii) comprises one or more Glyco_hydro_20 catalytic domains, and
      (iii) comprises the conserved motif I [IV]P[ED][LVI]DXP[AN]H (SEQ ID NO 21), the conserved motif II NYN[AS]Y[SY]LY (SEQ ID NO 22) and/or the conserved motif III GXDE (SEQ ID NO 41); and
   (b) at least one cleaning ingredient selected from the group consisting of at least one builder, at least one surfactant, and at least one bleach component;
   wherein the composition is in the form of a liquid, gel, powder, granulate, paste, or spray composition.

2. The composition of claim 1, wherein the polypeptide has at least 96% sequence identity to SEQ ID NO: 33.

3. The composition of claim 1, wherein the polypeptide has at least 97% sequence identity to SEQ ID NO: 33.

4. The composition of claim 1, wherein the polypeptide has at least 98% sequence identity to SEQ ID NO: 33.

5. The composition of claim 1, wherein the polypeptide has at least 99% sequence identity to SEQ ID NO: 33.

6. The composition of claim 1, wherein the polypeptide comprises SEQ ID NO: 33.

7. The composition of claim 1, wherein the polypeptide is a fragment of SEQ ID NO: 33, wherein the fragment has hexosaminidase activity and at least 95% sequence identity to SEQ ID NO: 33.

8. The composition of claim 1, wherein the polypeptide has at least 96% sequence identity to SEQ ID NO: 34.

9. The composition of claim 1, wherein the polypeptide has at least 97% sequence identity to SEQ ID NO: 34.

10. The composition of claim 1, wherein the polypeptide has at least 98% sequence identity to SEQ ID NO: 34.

11. The composition of claim 1, wherein the polypeptide has at least 99% sequence identity to SEQ ID NO: 34.

12. The composition of claim 1, wherein the polypeptide comprises SEQ ID NO: 34.

13. The composition of claim 1, wherein the polypeptide is a fragment of SEQ ID NO: 34, wherein the fragment has hexosaminidase activity and at least 95% sequence identity to SEQ ID NO: 34.

14. The composition of claim 1, wherein the polypeptide has N-acetylglucosaminidase activity and/or β-N-acetylglucosamininidase activity.

15. The composition of claim 1, wherein the polypeptide comprises one or more of the motifs ARAYYPV (SEQ ID NO 42), AWNDGID (SEQ ID NO 43), DDQNVGI (SEQ ID NO 44) or DPRIH (SEQ ID NO 45).

16. The composition of claim 1, wherein the composition is a laundry composition or dish wash composition.

17. The composition of claim 1, which comprises at least one builder in an amount from about 1 wt. % to about 65 wt. %, and wherein the builder is selected from the group consisting of phosphates, sodium citrate builders, sodium carbonate, sodium silicate, sodium and zeolites.

18. The composition of claim 1, which comprises from about 1 wt. % to about 40 wt. % of at least one bleach component, wherein the bleach component is a percarbonate and/or a bleach catalyst.

19. The composition of claim 1, which comprises from about 2 wt. % to about 60 wt. % of at least one surfactant, wherein the surfactant is anionic, nonionic or cationic.

20. A method for laundering a textile, comprising:
 (a) exposing the textile to a wash liquor comprising a composition of claim 1; and
 (b) completing at least one wash cycle.

* * * * *